United States Patent
Abouabdellah et al.

(10) Patent No.: US 8,716,289 B2
(45) Date of Patent: May 6, 2014

(54) CARBAMATE DERIVATIVES OF ALKYL-HETEROCYCLES, PREPARATION THEREOF AND THERAPEUTIC USE THEREOF

(75) Inventors: Ahmed Abouabdellah, Paris (FR); Nathalie Chereze, Paris (FR); Aude Fayol, Paris (FR); Mourad Saady, Paris (FR); Julien Vache, Paris (FR); Corinne Veronique, Paris (FR); Philippe Yaiche, Paris (FR)

(73) Assignee: Sanofi, Paris (FR)

( * ) Notice: Subject to any disclaimer, the term of this patent is extended or adjusted under 35 U.S.C. 154(b) by 132 days.

(21) Appl. No.: 13/129,235

(22) PCT Filed: Nov. 13, 2009

(86) PCT No.: PCT/FR2009/052179
§ 371 (c)(1),
(2), (4) Date: Oct. 5, 2011

(87) PCT Pub. No.: WO2010/055267
PCT Pub. Date: May 20, 2010

(65) Prior Publication Data
US 2012/0015950 A1    Jan. 19, 2012

(30) Foreign Application Priority Data
Nov. 14, 2008 (FR) ...................... 08 06371

(51) Int. Cl.
| | | |
|---|---|---|
| *A61K 31/47* | (2006.01) | |
| *A61K 31/497* | (2006.01) | |
| *A61K 31/498* | (2006.01) | |
| *A61K 31/501* | (2006.01) | |
| *A61K 31/502* | (2006.01) | |
| *A61K 31/506* | (2006.01) | |

(52) U.S. Cl.
USPC . 514/248; 514/249; 514/252.01; 514/255.05; 514/275; 514/314; 544/237; 544/238; 544/242; 544/336; 544/353; 546/162

(58) Field of Classification Search
CPC .. C07D 401/12; C07D 403/12; C07D 413/12; C07D 417/12
USPC .......... 544/237, 238, 242, 336, 353; 546/162, 546/268.1
See application file for complete search history.

(56) References Cited

FOREIGN PATENT DOCUMENTS

| | | |
|---|---|---|
| EP | 1 780 210 A1 | 5/2007 |
| WO | WO 2004/033422 A2 | 4/2004 |
| WO | WO 2004/099176 A1 | 11/2004 |
| WO | WO 2006/123244 A2 | 11/2006 |
| WO | WO 2010/010288 A2 | 1/2010 |

OTHER PUBLICATIONS

International Search Report dated Mar. 4, 2010.
International Preliminary Report on Patentability dated Jun. 7,2011 issued in PCT/FR2009/052179.
Costa Rican Opposition dated Oct. 5, 2012 received from related International Application No. PCT/FR2009/052179, together with an English-language translation.

*Primary Examiner* — Brian McDowell
(74) *Attorney, Agent, or Firm* — Scully, Scott, Murphy & Presser, P.C.

(57) ABSTRACT

Compound corresponding to general formula (I): in which $R_2$ is a hydrogen or fluorine atom or a hydroxyl, cyano, trifluoromethyl, $C_{1-6}$-alkyl, $C_{1-6}$-alkoxy or $NR_8R_9$ group; n is an integer equal to 1, 2 or 3 and m is an integer equal to 1 or 2; A is a covalent bond or a $C_{1-8}$-alkylene group; $R_1$ is a phenyl, pyridinyl, pyridazinyl, pyrimidinyl, pyrazinyl, triazinyl, naphthyl, quinolinyl, isoquinolinyl, phthalazinyl, quinazolinyl, quinoxalinyl, cinnolinyl or naphthyridinyl group, this group being optionally substituted; $R_3$ is a hydrogen or fluorine atom, a $C_{1-6}$-alkyl group or a trifluoromethyl group; $R_4$ is a group selected from furanyl, pyrrolyl, thienyl, isothiazolyl, oxazolyl, isoxazolyl, pyrazolyl, oxadiazolyl, thiadiazolyl, imidazole, triazolyl, tetrazolyl, oxazolone, oxazolidinone, isoxazolone, isoxazolidinone, isothiazolone, isothiazolidinone, imidazolone, imidazolidinone, pyrazolone, pyrazolidinone, oxadiazolone, thiadiazolone and triazolone, this group being optionally substituted; in the form of a base or of an addition salt with an acid. Therapeutic use.

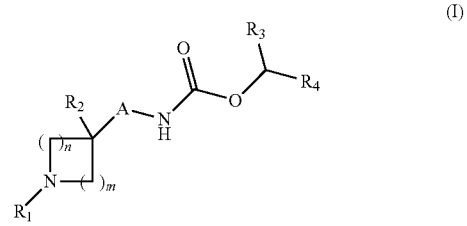

(I)

12 Claims, No Drawings

CARBAMATE DERIVATIVES OF ALKYL-HETEROCYCLES, PREPARATION THEREOF AND THERAPEUTIC USE THEREOF

The invention relates to carbamate derivatives of alkyl-heterocycles, to their preparation and to their therapeutic use There is still a need to find and develop products that inhibit the enzyme FAAH (Fatty Acid Amide Hydrolase). The compounds of the invention satisfy this aim. These compounds should have metabolic, pharmacokinetic and toxicological properties that allow their use as medicaments. Among these properties, mention may be made especially of the inhibitory effect on cytochromes P450 and more particularly on the isoenzyme CYP3A4.

Document WO 2004/099 176 describes compounds with inhibitory activity on the enzyme FAAH, containing a glycolamide carbamate group.

The compounds of the invention correspond to the general formula (I):

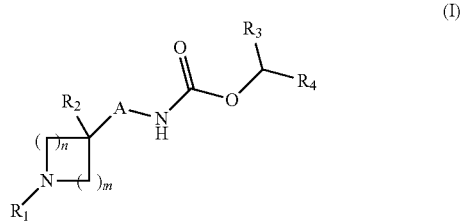

in which $R_2$ represents a hydrogen or fluorine atom or a hydroxyl, cyano, trifluoromethyl, $C_{1-6}$-alkyl, $C_{1-6}$-alkoxy or $NR_8R_9$ group;

n represents an integer equal to 1, 2 or 3 and m represents an integer equal to 1 or 2;

A represents a covalent bond or a group $C_{1-8}$-alkylene;

$R_1$ represents a group $R_5$ optionally substituted with one or more groups $R_6$ and/or $R_7$;

$R_5$ represents a group chosen from phenyl, pyridyl, pyridazinyl, pyrimidinyl, pyrazinyl, triazinyl, naphthyl, quinolinyl, isoquinolinyl, phthalazinyl, quinazolinyl, quinoxalinyl, cinnolinyl and naphthyridinyl;

$R_6$ represents a halogen atom or a cyano, —$CH_2CN$, nitro, hydroxyl, $C_{1-6}$alkyl, $C_{1-6}$-alkoxy, $C_{1-6}$-thioalkyl, $C_{1-6}$-haloalkyl, $C_{1-6}$-haloalkoxy, $C_{1-6}$-halothioalkyl, $C_{3-7}$-cycloalkyl, $C_{3-7}$-cycloalkyl-$C_{1-3}$-alkylene, $C_{3-7}$-cycloalkyl-$C_{1-3}$-alkylene-O—, $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $SO_2R_8$, $SO_2NR_8R_9$ or —O—($C_{1-3}$-alkylene)-O-group;

$R_7$ represents a group chosen from furyl, pyrrolyl, thienyl, oxazolyl, isoxazolyl, thiazolyl, isothiazolyl, imidazolyl, pyrazolyl, oxadiazolyl, thiadiazolyl, phenyl, pyridyl, pyridazinyl, pyrimidinyl, pyrazinyl, triazinyl, naphthyl, quinolinyl, isoquinolinyl, phthalazinyl, quinazolinyl, quinoxalinyl, cinnolinyl, naphthyridinyl, imidazopyrimidinyl, thienopyrimidinyl, benzofuryl, benzothienyl, benzimidazolyl, benzoxazolyl, benzisoxazolyl, benzothiazolyl, benzisothiazolyl, indolyl, isoindolyl, indazolyl, pyrrolopyridyl, furopyridyl, thienopyridyl, imidazopyridyl, pyrazolopyridyl, oxazolopyridyl, isoxazolopyridyl, thiazolopyridyl, phenyloxy, benzyloxy and pyrimidinoxy; or the group(s) $R_7$ possibly being substituted with one or more groups $R_6$ that may be identical to or different from each other;

$R_3$ represents a hydrogen or fluorine atom, a group $C_{1-6}$-alkyl or a trifluoromethyl group;

$R_4$ represents a group chosen from furyl, pyrrolyl, thienyl, isothiazolyl, oxazolyl, isoxazolyl, pyrazolyl, oxadiazolyl, thiadiazolyl, imidazolyl, triazolyl and tetrazolyl;

this group being optionally substituted with one or more substituents chosen from a halogen atom, a group $C_{1-6}$-alkyl, $C_{1-6}$-haloalkyl, $C_{3-7}$-cycloalkyl, $C_{3-7}$-cycloalkyl-$C_{1-3}$-alkylene, $C_{1-6}$-haloalkoxy, cyano, $NR_8R_9$, $NR_8COR_9$, $NR_8CO_2R_9$, $NR_8SO_2R_9$, $NR_8SO_2NR_8R_9$, $COR_E$, $CO_2R_8$, $CONR_8R_9$, $CON(R_8)$ ($C_{1-3}$-alkylene-$NR_{10}R_{11}$), $SO_2R_8$, $SO_2NR_8R_9$, —O—($C_{1-3}$-alkylene)-O—, phenyl, phenyloxy, benzyloxy, pyridyl, pyrazinyl, pyridazinyl, triazinyl or pyrimidinyl; the phenyl, phenyloxy, pyridyl, pyrazinyl, pyridazinyl, triazinyl and pyrimidinyl groups possibly being substituted with one or more substituents chosen from a halogen atom and a cyano, nitro, $C_{1-6}$-alkyl, $C_{1-6}$-alkoxy, $C_{1-6}$- thioalkyl, $C_{1-6}$-haloalkyl, $C_{1-6}$-haloalkoxy, $C_{1-6}$-halothioalkyl, $C_{3-7}$-cycloalkyl or $C_{3-7}$-cycloalkyl-$C_{1-3}$-alkylene group;

$R_8$, $R_9$, $R_{10}$ and $R_{11}$ represent, independently of each other, a hydrogen atom or a group $C_{1-8}$-alkyl, or form, with the atom(s) that bear(s) them, in the case of $NR_8R_9$, a ring chosen from azetidine, pyrrolidine, piperidine, morpholine, thiomorpholine, azepine, oxazepine and piperazine rings, this ring being optionally substituted with a group $C_{1-6}$-alkyl or benzyl;

in the case of $NR_8COR_9$, a lactam ring; in the case of $NR_8CO_2R_9$, a oxazolidinone, oxazinone or oxazepinone ring; in the case of $NR_8SO_2R_9$, a sultam ring; in the case of $NR_8SO_2NR_8R_9$, a thiazolidine dioxide or thiadiazinane dioxide ring.

Among the compounds of general formula (I), a first subgroup of compounds is formed from compounds for which $R_2$ represents a hydrogen or fluorine atom or a hydroxyl, $C_{1-6}$-alkyl or $NR_8R_9$ group. More particularly, $R_8$ and $R_9$ represent a group $C_{1-6}$-alkyl.

Among the compounds of general formula (I), a second subgroup of compounds is formed from compounds for which $R_2$ represents a hydrogen atom.

Among the compounds of general formula (I), a third subgroup of compounds is formed from compounds for which n represents an integer equal to 2 and m represents an integer equal to 2.

Among the compounds of general formula (I), a fourth subgroup of compounds is formed from compounds for which A represents a group $C_{1-8}$-alkylene, more particularly an ethylene, propylene or ethylene group.

Among the compounds of general formula (I), a fifth subgroup of compounds is formed from compounds for which A represents a covalent bond.

Among the compounds of general formula (I), a sixth subgroup of compounds is formed from compounds for which $R_1$ represents a group $R_5$ optionally substituted with one or more groups $R_6$ and/or $R_7$;

$R_5$ represents a phenyl, pyridyl, pyridazinyl, pyrimidinyl, pyrazinyl, quinolinyl, phthalazinyl or quinoxalinyl group;

$R_6$ represents a nitro, $C_{1-6}$-alkyl, $C_{1-6}$-alkoxy, $C_{1-6}$-haloalkyl, $C_{1-6}$-haloalkoxy or —O—($C_{1-3}$-alkylene)-O— group or a halogen atom, more particularly a chlorine or fluorine atom;

$R_7$ represents a phenyl group that may be substituted with one or more groups $R_6$ that may be identical to or different from each other.

Among the compounds of general formula (I), a seventh subgroup of compounds is formed from compounds for which $R_1$ represents a group $R_5$ optionally substituted with one or more groups $R_6$ and/or $R_7$;

$R_5$ represents a pyridyl, pyridazinyl, pyrimidinyl, pyrazinyl, quinolinyl, phthalazinyl or quinoxalinyl group;

$R_6$ represents a nitro, $C_{1-6}$-alkyl, $C_{1-6}$-alkoxy, $C_{1-6}$-haloalkyl, $C_{1-6}$-haloalkoxy or —O—($C_{1-3}$-alkylene)-O— group or a halogen atom, more particularly a chlorine or fluorine atom;

$R_7$ represents a phenyl group that may be substituted with one or more groups $R_6$ that may be identical to or different from each other.

Among the compounds of general formula (I), an eighth subgroup of compounds is formed from compounds for which $R_1$ represents a group $R_5$ optionally substituted with one or more groups $R_6$ and/or $R_7$;

$R_5$ represents a phenyl, pyridyl, pyrazinyl or quinolinyl group;

$R_6$ represents a halogen atom, more particularly a chlorine or fluorine atom;

$R_7$ represents a phenyl group that may be substituted with one or more groups $R_6$ that may be identical to or different from each other.

Among the compounds of general formula a ninth subgroup of compounds is formed from compounds for which $R_3$ represents a trifluoromethyl, a $C_{1-6}$-alkyl, more particularly an isobutyl, or a hydrogen atom.

Among the compounds of general formula (I), a tenth subgroup of compounds is formed from compounds for which $R_3$ represents a hydrogen atom.

Among the compounds of general formula (I), an eleventh subgroup of compounds is formed from compounds for which $R_4$ represents a group chosen from oxazolyl, isoxazolyl, furyl, imidazolyl, pyrazolyl, oxadiazolyl, thiadiazolyl and triazolyl groups;
this group optionally substituted with one or more substituents chosen from a group $C_{1-6}$-alkyl, more particularly methyl, ethyl, isopropyl or tert-butyl, $COOR_8$, $CON(R_8)(C_{1-3}$-alkylene-$NR_{10}R_{11}$), $CONR_8R_9$, phenyl; the phenyl group possibly being substituted with one or more substituents chosen from a halogen atom, more particularly a chlorine or fluorine atom, a group $C_{1-6}$-alkoxy, more particularly methoxy;

$R_8$ and $R_9$ represent, independently of each other, a hydrogen atom or a group more particularly a methyl or ethyl, or form, together with the atom that bears them, a piperazine ring, $R_{10}$ and $R_{11}$ represent, independently of each other, a hydrogen atom or a group $C_{1-6}$-alkyl.

Among the compounds of general formula (I), a twelfth subgroup of compounds is formed from compounds for which $R_4$ represents a group chosen from oxazolyl, isoxazolyl, pyrazolyl, oxadiazolyl, thiadiazolyl, imidazolyl, triazolyl and tetrazolyl;
this group optionally substituted with one or more substituents chosen from a group $C_{1-6}$-alkyl, more particularly methyl, ethyl, isopropyl or tert-butyl, $COOR_8$, $CON(R_8)(C_{1-3}$-alkylene-$NR_{10}R_{11}$), $CONR_8R_9$ or phenyl; the phenyl group possibly being substituted with one or more substituents chosen from a halogen atom, more particularly a chlorine or fluorine atom, or a group $C_{1-6}$-alkoxy, more particularly methoxy;

$R_8$ and $R_9$ represent, independently of each other, a hydrogen atom or a group $C_{1-6}$-alkyl, more particularly a methyl or ethyl, or form, together with the atom that bears them, a piperazine ring, $R_{10}$ and $R_{11}$ represent, independently of each other, a hydrogen atom or a group $C_{1-6}$-alkyl.

Among the compounds of general formula (I), a thirteenth subgroup of compounds is formed from compounds for which $R_4$ represents a group chosen from an oxazolyl, isoxazolyl, pyrazolyl, oxadiazolyl, thiadiazolyl or triazolyl; this group optionally substituted with one or more substituents chosen from a group $C_{1-6}$-alkyl, more particularly methyl, ethyl, isopropyl or tert-butyl, $CONR_8R_9$, phenyl; the phenyl group possibly being substituted with one or more substituents chosen from a halogen atom, more particularly a chlorine or fluorine atom, and a group $C_{1-6}$-alkoxy, more particularly methoxy;

$R_8$ and $R_9$ represent, independently of each other, a hydrogen atom or a group $C_{1-6}$-alkyl, more particularly a methyl.

Among the compounds of general formula (I), a fourteenth subgroup of compounds is formed from compounds for which $R_4$ represents a 3-carbamoylisoxazol-5-yl group.

Among the compounds of general formula (I), a fifteenth subgroup of compounds is formed from compounds for which $R_4$ represents a 2-methyl-2H-[1,2,4]triazol-3-yl group.

Among the compounds of general formula (I), a sixteenth subgroup of compounds is formed from compounds for which $R_4$ represents a 3-(4-chlorophenyl)[1,2,4]oxadiazol-5-yl group.

Among the compounds of general formula (I), a seventeenth subgroup of compounds is formed from compounds for which $R_4$ represents a 3-(4-chlorophenyl)isoxazol-5-yl group.

Among the compounds of general formula (I), an eighteenth subgroup of compounds is formed from compounds for which $R_4$ represents a 3-ethyl[1,2,4]oxadiazol-5-yl group.

Among the compounds of general formula (I), a nineteenth subgroup of compounds is formed from compounds for which $R_4$ represents a 5-methyl-3-phenylisoxazol-4-yl group.

Among the compounds of general formula (I), a twentieth subgroup of compounds is formed from compounds for which $R_4$ represents a 3-isopropyl[1,2,4]oxadiazol-5-yl group.

Among the compounds of general formula (I), a twenty-first subgroup of compounds is formed from compounds for which $R_4$ represents a 1-methyl-1H-pyrazol-3-yl group.

Among the compounds of general formula (I), a twenty-second subgroup of compounds is formed from compounds for which $R_4$ represents a [1,2,3]thiadiazol-4-yl group.

Among the compounds of general formula (I), a twenty-third subgroup of compounds is formed from compounds for which $R_4$ represents a 5-tert-butyl[1,3,4]thiadiazol-2-yl group.

Among the compounds of general formula (I), a twenty-fourth subgroup of compounds is formed from compounds for which $R_4$ represents a 5-isopropyl[1,2,4]oxadiazol-3-yl group.

Among the compounds of general formula (I), a twenty-fifth subgroup of compounds is formed from compounds for which $R_4$ represents a 5-(4-fluorophenyl)[1,3,4]oxadiazol-2-yl group.

Among the compounds of general formula (I), a twenty-sixth subgroup of compounds is formed from compounds for which $R_4$ represents a 5-(4-chlorophenyl)[1,3,4]oxadiazol-2-yl group.

Among the compounds of general formula (I), a twenty-seventh subgroup of compounds is formed from compounds for which $R_4$ represents a 5-(4-methoxyphenyl)[1,3,4]oxadiazol-2-yl group.

Among the compounds of general formula (I), a twenty-eighth subgroup of compounds is formed from compounds for which $R_4$ represents a 3-(4-fluorophenyl)[1,2,4]oxadiazol-5-yl group.

Among the compounds of general formula (I), a twenty-ninth subgroup of compounds is formed from compounds for which $R_4$ represents a 3-(3-fluorophenyl)[1,2,4]oxadiazol-5-yl group.

Among the compounds of general formula (I), a thirtieth subgroup of compounds is formed from compounds for which $R_4$ represents a 5-(4-chlorophenyl)[1,2,4]thiadiazol-3-yl group.

Among the compounds of general formula (I), a thirty-first subgroup of compounds is formed from compounds for which $R_4$ represents a 3-methylcarbamoylisoxazol-5-yl group.

Among the compounds of general formula (I), a thirty-second subgroup of compounds is formed from compounds for which $R_4$ represents a 4-carbamoyloxazol-2-yl group.

Among the compounds of general formula (I), a thirty-third subgroup of compounds is formed from compounds for which $R_4$ represents a 3-dimethylcarbamoylisoxazol-5-yl group.

Among the compounds of general formula (I), a thirty-fourth subgroup of compounds is formed from compounds for which $R_1$ represents a group $R_5$ optionally substituted with one or more groups $R_6$ and/or $R_7$;
  $R_5$ represents a phenyl, pyridyl, pyrazinyl or quinolinyl group; $R_6$ represents a halogen atom, more particularly a chlorine or fluorine atom;
  $R_7$ represents a phenyl group that may be substituted with one or more groups $R_6$ that may be identical to or different from each other.
$R_2$ and $R_3$ represent a hydrogen atom; $R_4$ represents a 3-carbamoylisoxazol-5-yl group; n represents an integer equal to 2 and m represents an integer equal to 2;
A represents an alkylene group.

Among the compounds of general formula (I), a thirty-fifth subgroup of compounds is formed from compounds for which $R_1$ represents a group $R_5$ optionally substituted with one or more groups $R_6$ and/or $R_7$;
  $R_5$ represents a pyridyl, pyridazinyl, pyrimidinyl, pyrazinyl, quinolinyl, phthalazinyl or quinoxalinyl group;
  $R_6$ represents a nitro, $C_{1-6}$-alkyl, $C_{1-6}$-alkoxy, $C_{1-6}$-haloalkyl, $C_{1-6}$-haloalkoxy or —O—($C_{1-3}$-alkylene)-O— group or a halogen atom, more particularly a chlorine or fluorine atom;
  $R_7$ represents a phenyl group that may be substituted with one or more groups $R_6$ that may be identical to or different from each other;
$R_2$ and $R_3$ represent a hydrogen atom;
$R_4$ represents a group chosen from furyl, pyrrolyl, thienyl, isothiazolyl, oxazolyl, isoxazolyl, pyrazolyl, oxadiazolyl, thiadiazolyl, imidazolyl, triazolyl and tetrazolyl optionally substituted with $CONR_8R_9$ in which $R_8$ and $R_9$ represent, independently of each other, a hydrogen atom or a group $C_{1-6}$-alkyl;
n represents an integer equal to 2 and m represents an integer equal to 2; A represents an alkylene group.

Among the compounds of general formula (I), a thirty-sixth subgroup of compounds is formed by the compounds of general formula (I) in which, simultaneously, $R_1$ and/or $R_2$ and/or $R_3$ and/or $R_4$ and/or n and/or m and/or A are as defined in the above groups.

Among the compounds of general formula (I), the following compounds may be mentioned (IUPAC nomenclature generated by the AutoNom software):
1. 3-carbamoylisoxazol-5-ylmethyl 2-[1-(6-chloroquinolin-2-yl)piperidin-4-yl]ethylcarbamate
2. 2-methyl-2H-[1,2,4]triazol-3-ylmethyl 2-[1-(6-chloroquinolin-2-yl)piperidin-4-yl]ethylcarbamate
3. 3-(4-chlorophenyl)isoxazol-5-ylmethyl 2-[1-(6-chloroquinolin-2-yl)piperidin-4-yl]ethylcarbamate
4. 3-(4-chlorophenyl)[1,2,4]oxadiazol-5-ylmethyl 2-[1-(6-chloroquinolin-2-yl)piperidin-4-yl]ethylcarbamate
5. 3-ethyl[1,2,4]oxadiazol-5-ylmethyl 2-[5'-(4-fluorophenyl)-3,4,5,6-tetrahydro-2H-[1,2']bipyridinyl-4-yl]-ethylcarbamate
6. 5-methyl-3-phenylisoxazol-4-ylmethyl 2-[1-(6-chloroquinolin-2-yl)piperidin-4-yl]ethylcarbamate
7. 3-isopropyl[1,2,4]oxadiazol-5-ylmethyl 2-[5'-(4-fluorophenyl)-3,4,5,6-tetrahydro-2H-[1,2']bipyridinyl-4-yl]-ethylcarbamate
8. 1-methyl-1H-pyrazol-3-ylmethyl 2-[5'-(4-fluorophenyl)-3,4,5,6-tetrahydro-2H-[1,2']bipyridinyl-4-yl]ethylcarbamate
9. [1,2,3]thiadiazol-4-ylmethyl 2-[5'-(4-fluorophenyl)-3,4,5,6-tetrahydro-2H-[1,2']bipyridinyl-4-yl]ethylcarbamate
10. 5-tert-butyl[1,3,4]thiadiazol-2-ylmethyl 2-[5'-(4-fluorophenyl)-3,4,5,6-tetrahydro-2H-[1,2']bipyridinyl-4-yl]-ethylcarbamate
11. 5-isopropyl[1,2,4]oxadiazol-3-ylmethyl 2-[5'-(4-fluorophenyl)-3,4,5,6-tetrahydro-2H-[1,2']bipyridinyl-4-yl]-ethylcarbamate
12. 5-(4-fluorophenyl)[1,3,4]oxadiazol-2-ylmethyl 2-[1-(6-chloroquinolin-2-yl)piperidin-4-yl]ethylcarbamate
13. 5-(4-chlorophenyl)[1,3,4]oxadiazol-2-ylmethyl 2-[1-(6-chloroquinolin-2-yl)piperidin-4-yl]ethylcarbamate
14. 5-(4-methoxyphenyl)[1,3,4]oxadiazol-2-ylmethyl 2-[1-(6-chloroquinolin-2-yl)piperidin-4-yl]ethylcarbamate
15. 3-(4-fluorophenyl)[1,2,4]oxadiazol-5-ylmethyl 2-[1-(6-chloroquinolin-2-yl)piperidin-4-yl]ethylcarbamate
16. 3-(3-fluorophenyl)[1,2,4]oxadiazol-5-ylmethyl 2-[1-(6-chloroquinolin-2-yl)piperidin-4-yl]ethylcarbamate
17. 5-(4-chlorophenyl)[1,2,4]thiadiazol-3-ylmethyl 2-[1-(6-chloroquinolin-2-yl)piperidin-4-yl]ethylcarbamate
18. [1,2,3]thiadiazol-4-ylmethyl 2-[1-(6-chloroquinolin-2-yl)piperidin-4-yl]ethylcarbamate
19. 3-carbamoylisoxazol-5-ylmethyl 2-[5'-(4-fluorophenyl)-3,4,5,6-tetrahydro-2H-[1,2']bipyridinyl-4-yl]ethylcarbamate
20. 3-methylcarbamoylisoxazol-5-ylmethyl 2-[1-(6-chloroquinolin-2-yl)piperidin-4-yl]ethylcarbamate
21. 4-carbamoyloxazol-2-ylmethyl 2-[5'-(4-fluorophenyl)-3,4,5,6-tetrahydro-2H-[1,2']bipyridinyl-4-yl]ethylcarbamate
22. 3-methylcarbamoylisoxazol-5-ylmethyl 2-[6'-(4-fluorophenyl)-3,4,5,6-tetrahydro-2H-[1,2']bipyridinyl-4-yl]-ethylcarbamate
23. 3-carbamoylisoxazol-5-ylmethyl 2-[1-(6-fluoroquinolin-2-yl)piperidin-4-yl]ethylcarbamate
24. 3-carbamoylisoxazol-5-ylmethyl 2-[6'-(4-fluorophenyl)-3,4,5,6-tetrahydro-2H-[1,2']bipyridinyl-4-yl]ethylcarbamate
25. 3-methylcarbamoylisoxazol-5-ylmethyl 2-[1-(6-fluoroquinolin-2-yl)piperidin-4-yl]ethylcarbamate 26. 3-methylcarbamoylisoxazol-5-ylmethyl 2-[5'-(4-fluorophenyl)-3,4,5,6-tetrahydro-2H-[1,2']bipyridinyl-4-yl]-ethylcarbamate
27. 3-dimethylcarbamoylisoxazol-5-ylmethyl 2-[6'-(4-fluorophenyl)-3,4,5,6-tetrahydro-2H-[1,2']bipyridinyl-4-yl]-ethylcarbamate
28. 3-carbamoylisoxazol-5-ylmethyl 2-[5'-(3-fluorophenyl)-3,4,5,6-tetrahydro-2H-[1,2']bipyridinyl-4-yl]ethylcarbamate
29. 3-methylcarbamoylisoxazol-5-ylmethyl 2-[1-(4'-fluorobiphenyl-4-yl)piperidin-4-yl]ethylcarbamate
30. 3-dimethylcarbamoylisoxazol-5-ylmethyl 2-[5'-(4-fluorophenyl)-3,4,5,6-tetrahydro-2H-[1,2']bipyridinyl-4-yl]-ethylcarbamate
31. 3-dimethylcarbamoylisoxazol-5-ylmethyl 2-[1-(6-chloroquinolin-2-yl)piperidin-4-yl]ethylcarbamate
32. 3-methylcarbamoylisoxazol-5-ylmethyl 2-{1-[6-(4-fluorophenyl)pyrazin-2-yl]piperidin-4-yl}ethylcarbamate
33. 3-carbamoylisoxazol-5-ylmethyl (2-{1-[6-(4-fluorophenyl)-pyrazin-2-yl]piperidin-4-yl]ethylcarbamate
34. 3-dimethylcarbamoylisoxazol-5-ylmethyl (2-{1-[6-(4-fluorophenyl)pyrazin-2-yl]piperidin-4-yl]ethylcarbamate
35. 3-methylcarbamoylisoxazol-5-ylmethyl (2-{1-[5-(4-fluoro-phenyl)pyrimidin-2-yl]piperidin-4-yl]ethylcarbamate
36. 3-dimethylcarbamoylisoxazol-5-ylmethyl (2-{1-[5-(4-fluorophenyl)pyrimidin-2-yl]piperidin-4-yl]ethylcarbamate
37. 3-methylcarbamoylisoxazol-5-ylmethyl {2-[1-(4-trifluoromethylpyrimidin-2-yl)piperidin-4-yl]ethylcarbamate
38. 3-carbamoylisoxazol-5-ylmethyl {2-[1-(4-trifluoromethylpyrimidin-2-yl)piperidin-4-yl]ethylcarbamate
39. 3-carbamoylisoxazol-5-ylmethyl (2-{1-[5-(4-fluorophenyl)-pyrimidin-2-yl]piperidin-4-yl]ethylcarbamate
40. 3-dimethylcarbamoylisoxazol-5-ylmethyl {2-[1-(4-trifluoromethylpyrimidin-2-yl)piperidin-4-yl]ethylcarbamate
41. 3-carbamoylisoxazol-5-ylmethyl (2-{1-[6-(4-fluorophenyl)-pyridazin-3-yl]piperidin-4-yl]ethylcarbamate
42. 3-(2-dimethylaminoethylcarbamoyl)isoxazol-5-ylmethyl {2-[5'-(4-fluorophenyl)-3,4,5,6-tetrahydro-2H-[1,2']bipyridinyl-4-yl]ethylcarbamate
43. 3-carbamoylisoxazol-5-ylmethyl [2-(5'-isobutyl-3,4,5,6-tetrahydro-2H-[1,2']bipyridinyl-4-yl]ethylcarbamate
44. 3-carbamoylisoxazol-5-ylmethyl [2-[5'-(2,2-dimethylpropyl)-3,4,5,6-tetrahydro-2H-[1,2']bipyridinyl-4-yl]-ethylcarbamate
45. 3-carbamoylisoxazol-5-ylmethyl [2-(5'-m-tolyl-3,4,5,6-tetrahydro-2H-[1,2']bipyridinyl-4-yl]ethylcarbamate
46. 3-(4-methylpiperazine-1-carbonyl)isoxazol-5-ylmethyl {2-[5'-(4-fluorophenyl)-3,4,5,6-tetrahydro-2H-[1,2']bipyridinyl-4-yl]ethylcarbamate
47. 3-carbamoylisoxazol-5-ylmethyl {2-[5'-(3-trifluoromethoxyphenyl)-3,4,5,6-tetrahydro-2H-[1,2']bipyridinyl-4-yl]-ethylcarbamate
48. 3-carbamoylisoxazol-5-ylmethyl {2-[5'-(3-chlorophenyl)-3,4,5,6-tetrahydro-2H-[1,2']bipyridinyl-4-yl]ethyl-carbamate
49. 3-carbamoylisoxazol-5-ylmethyl {2-[5'-(3-fluoro-5-methoxyphenyl)-3,4,5,6-tetrahydro-2H-[1,2']bipyridinyl-4-yl]-ethylcarbamate
50. 3-carbamoylisoxazol-5-ylmethyl [2-(5'-benzo[1.3]dioxol-5-yl-3,4,5,6-tetrahydro-2H-[1,2']bipyridinyl-4-yl]ethylcarbamate
51. ethyl 5-[4-fluoro-1-(4-trifluoromethylpyrimidin-2-yl)-piperidin-4-ylmethylcarbamoyloxymethyl]isoxazole-3-carboxylate
52. 1-methyl-1H-pyrazol-3-ylmethyl {3-[1-(4-trifluoromethylpyrimidin-2-yl)piperidin-4-yl]propylcarbamate
53. 5-{2-[1-(6-chloroquinolin-2-yl)piperidin-4-yl]ethylcarbamoyloxymethyl}isoxazole-3-carboxylic acid
54. 5-isopropyl[1,2,4]oxadiazol-3-ylmethyl [1-6-chloroquinoxalin-2-yl)piperidin-4-yl]methylcarbamate
55. 5-isopropyl[1,2,4]oxadiazol-3-ylmethyl [1-(4-trifluoromethylpyrimidin-2-yl)piperidin-4-yl]methylcarbamate
56. ethyl 5-[1-(6-chloroquinolin-2-yl)-4-fluoropiperidin-4-ylmethylcarbamoyloxymethyl]isoxazole-3-carboxylate
57. 3-methylcarbamoylisoxazol-5-ylmethyl [4-fluoro-1-(4-trifluoromethylpyrimidin-2-yl)piperidin-4-yl]methylcarbamate
58. 5-isopropyl[1,2,4]oxadiazol-3-ylmethyl [1-(4-nitro-2-trifluoromethylphenyl)piperidin-4-yl]methylcarbamate
59. 5-isopropyl[1,2,4]oxadiazol-3-ylmethyl [1-(4-chlorophthalazin-1-yl)piperidin-4-yl]methylcarbamate
60. 3-methylcarbamoylisoxazol-5-ylmethyl {2-[3-dimethylamino-1-(4-trifluoromethylpyrimidin-2-yl)azetidin-3-yl]ethylcarbamate
61. 3-methylcarbamoylisoxazol-5-ylmethyl {2-[4-ethyl-1-(4-trifluoromethylpyrimidin-2-yl)piperidin-4-yl]ethylcarbamate
62. 3-methylcarbamoylisoxazol-5-ylmethyl {2-[4-hydroxy-1-(4-trifluoromethylpyrimidin-2-yl)piperidin-4-yl]ethyl-carbamate
63. 2,2,2-trifluoro-1-(1-methyl-1H-imidazol-2-yl)ethyl {2-[1-(4-chlorophthalazin-1-yl)-3-dimethylaminoazetidin-3-yl]ethyl}-carbamate
64. 3-methylcarbamoylisoxazol-5-ylmethyl {2-[1-(6-chloroquinoxalin-2-yl)-4-ethylpiperidin-4-yl]ethylcarbamate
65. 3-methylcarbamoylisoxazol-5-ylmethyl {2-[1-(6-chloroquinoxalin-2-yl)-4-isobutylpiperidin-4-yl]ethylcarbamate
66. 3-methylcarbamoylisoxazol-5-ylmethyl {2-[4-isobutyl-1-(4-nitro-2-trifluoromethylphenyl)piperidin-4-yl]ethyl}carbamate
67. 5-isopropyl[1,2,4]oxadiazol-3-ylmethyl (1-isoquinolin-1-ylpiperidin-4-ylmethyl)carbamate
68. 3-carbamoylisoxazol-5-ylmethyl (2-{1-[5-(4-fluorophenyl)-pyrazin-2-yl]piperidin-4-yl}ethyl)carbamate
69. 3-methylcarbamoylisoxazol-5-ylmethyl (2-{1-[5-(4-fluorophenyl)pyrazin-2-yl]piperidin-4-yl}ethyl)carbamate
70. 3-methylcarbamoylisoxazol-5-ylmethyl [1-(4-trifluoromethylpyrimidin-2-yl)piperidin-4-yl]carbamate
71. ethyl 5-{2-[1-(6-chloroquinolin-2-yl)piperidin-4-yl]-ethylcarbamoyloxymethyl}isoxazole-3-carboxylate
72. 3-methylcarbamoylisoxazol-5-ylmethyl {2-[4-methyl-1-(4-trifluoromethylpyrimidin-2-yl)piperidin-4-yl]ethyl}carbamate
73. 2,2,2-trifluoro-1-(1-methyl-1H-imidazol-2-yl)ethyl {2-[1-(6-chloroquinolin-2-yl)piperidin-4-yl]ethyl}carbamate
74. 3-carbamoylisoxazol-5-ylmethyl (±)[1-(4-trifluoromethylpyrimidin-2-yl)azepan-4-yl]carbamate
75. 3-methylcarbamoylisoxazol-5-ylmethyl [1-(4-chlorophthalazin-1-yl)piperidin-4-yl]carbamate
76. 3-methylcarbamoylisoxazol-5-ylmethyl [1-(4-nitro-2-trifluoromethylphenyl)piperidin-4-yl]carbamate
77. 3-methylcarbamoylisoxazol-5-ylmethyl [1-(6-chloroquinoxalin-2-yl)piperidin-4-yl]carbamate
78. 3-methylcarbamoylisoxazol-5-ylmethyl {2-[1-(6-chloroquinoxalin-2-yl)-4-methylpiperidin-4-yl]ethyl}carbamate
79. 3-methylcarbamoylisoxazol-5-ylmethyl (±)[1-(4-chlorophthalazin-1-yl)pyrrolidin-3-ylmethyl]carbamate
80. 1-furan-3-yl-3-methylbutyl {2-[1-(6-chloroquinolin-2-yl)-piperidin-4-yl]ethyl}carbamate 81. 1-furan-3-yl-3-methylbutyl {2-[6'-(4-fluorophenyl)-3,4, 5,6-tetrahydro-2H-[1,2']bipyridinyl-4-yl]ethyl}carbamate
82. 3-carbamoylisoxazol-5-ylmethyl {2-[1-(4-trifluoromethylpyrimidin-2-yl)azetidin-3-yl]ethyl}carbamate
83. 3-methylcarbamoylisoxazol-5-ylmethyl {2-[1-(4-trifluoromethylpyrimidin-2-yl)azetidin-3-yl]ethyl}carbamate
84. 3-methylcarbamoylisoxazol-5-ylmethyl (−)[1-(4-chloropyrimidin-2-yl)pyrrolidin-3-ylmethyl]carbamate
85. 3-methylcarbamoylisoxazol-5-ylmethyl (+)[1-(4-chloropyrimidin-2-yl)pyrrolidin-3-ylmethyl]carbamate in the form of base or of an acid-addition salt.

The compounds of general formula (I) may comprise one or more asymmetric carbons. They may exist in the form of enantiomers or diastereoisomers. The compounds of general formula (I) may also exist in the form of cis (Z) or trans (E) stereoisomers. These stereoisomers, enantiomers and diastereoisomers, and also mixtures thereof, including racemic mixtures, form part of the invention.

The compounds of formula (I) may exist in the form of bases or of acid-addition salts. Such addition salts form part of the invention.

These salts are advantageously prepared with pharmaceutically acceptable acids, but the salts of other acids that are useful, for example, for purifying or isolating the compounds of formula (I) also form part of the invention.

In the context of the invention, the following definitions apply:

$C_{t-z}$ in which t and z may take values from 1 to 8, a carbon chain possibly containing from t to z carbon atoms, for example $C_{1-3}$ is a carbon chain that may contain from 1 to 3 carbon atoms;

alkyl, a linear or branched, saturated aliphatic group; for example, a $C_{1-6}$-alkyl group represents a linear or branched carbon chain of 1 to 6 carbon atoms, more particularly a methyl, ethyl, propyl, isopropyl, butyl, isobutyl, tert-butyl, pentyl or hexyl;

alkylene, a linear or branched, saturated divalent alkyl group, for example a $C_{1-3}$-alkylene group represents a linear or branched divalent carbon chain of 1 to 3 carbon atoms, more particularly a methylene, ethylene, 1-methylethylene or propylene;

cycloalkyl, a cyclic alkyl group, for example a $C_{3-7}$-cycloalkyl group represents a cyclic carbon-based group of 3 to 7 carbon atoms, more particularly a cyclopropyl, cyclobutyl, cyclopentyl, cyclohexyl or cycloheptyl;

alkoxy, a group —O-alkyl containing a linear or branched, saturated aliphatic chain;

thioalkyl, a group —S-alkyl containing a linear or branched, saturated aliphatic chain;

haloalkyl, an alkyl group in which one or more hydrogen atoms have been replaced with a halogen atom;

haloalkoxy, an alkoxy group in which one or more hydrogen atoms have been replaced with a halogen atom;

halothioalkyl, a thioalkyl group in which one or more hydrogen atoms have been replaced with a halogen atom;

halogen atom, a fluorine, a chlorine, a bromine or an iodine.

The compounds of the invention may be prepared according to various methods, illustrated by the schemes that follow.

Thus, a first method (scheme 1) consists in reacting an amine of general formula (II), in which A, $R_1$, $R_2$, m and n are as defined in the general formula (I) defined above, with a carbonate of general formula (III) in which Z represents a hydrogen atom or a nitro group, and $R_3$ and $R_4$ are as defined in the general formula (I) defined above, in the presence of a base such as triethylamine, pyridine, N,N-dimethylaminopyridine or diisopropylethylamine in a solvent such as toluene or 1,2-dichloroethane, at a temperature between room temperature and the reflux temperature of the solvent.

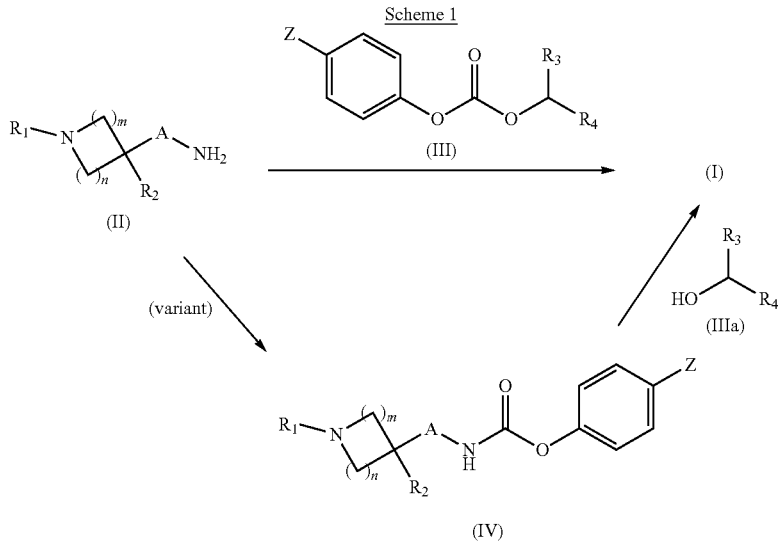

One variant for obtaining the compounds of general formula (I) (scheme 1) consists in reacting an amine of general formula (II), as defined above, with phenyl or 4-nitrophenyl chloroformate, in the presence of a base such as triethylamine or diisopropylethylamine, in a solvent such as dichloromethane or tetrahydrofuran, at a temperature between 0° C. and room temperature, to give the carbamate derivative of general formula (IV), in which A, $R_1$, $R_2$, m and n are as defined in the general formula (I) defined above, and Z represents a hydrogen atom or a nitro group. The carbamate derivative of general formula (IV) thus obtained is then converted into a compound of general formula (I), via the action of an alcohol of general formula HOCHR$_3$R$_4$ (IIIa), as defined above, in the presence of a base such as triethylamine, pyridine, N,N-dimethylaminopyridine or diisopropylethylamine, in a solvent such as toluene or dichloroethane, at a temperature between room temperature and the reflux temperature of the solvent.

A second method (scheme 2) allows production of compounds of general formula (I), in which $R_1$ represents a group $R_5$ substituted especially with a group $R_6$ of the type $C_{1-6}$-alkyl, $C_{3-7}$-cycloalkyl or $C_{3-7}$-cycloalkyl-$C_{1-3}$-alkylene, or with a group $R_7$ as defined in the general formula (I) defined above.

bonate of general formula (III) as defined above, under the conditions described for scheme 1 above, to give the carbamate derivative of general formula (IVb), in which A, $R_2$, $R_5$, m, N, $U_2$ and Z are as defined above. The compound of general formula (IVb) thus obtained is then converted into a carbamate derivative of general formula (Ia), via the action of an alcohol of general formula $HOCHR_3R_4$ (IIIa), as defined above, in the presence of a base such as triethylamine, pyridine, N,N-dimethylaminopyridine or N,N-diisopropylethy- Scheme 2

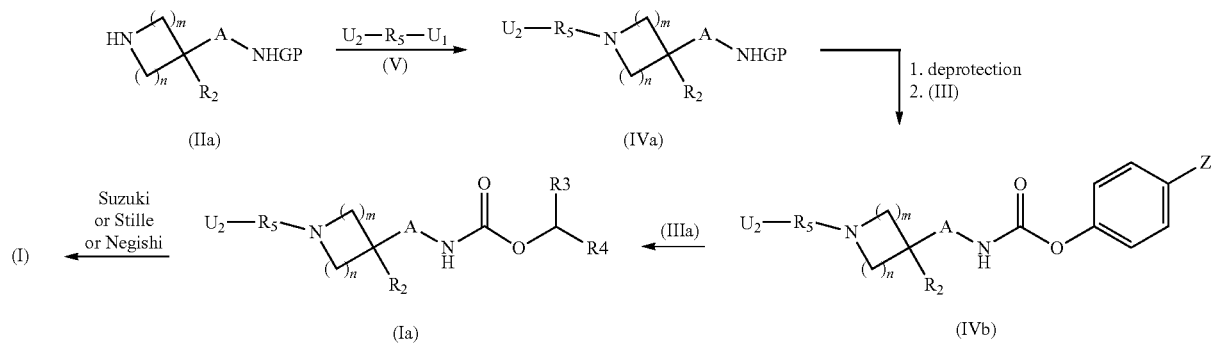

Thus, the first step consists in reacting an amine of general formula (IIa), in which A, $R_2$, m and n are as defined in the general formula (I) defined above, and PG represents a protecting group such as a Boc (tert-butyloxycarbonyl), a CBz (benzyloxycarbonyl), a benzyl or a benzhydryl, with a derivative of general formula (V), in which $R_5$ is as defined above, $U_1$ represents a halogen atom or an O-triflate group and $U_2$ represents a chlorine, bromine or iodine atom or an O-triflate group, using aromatic or heteroaromatic nucleophilic substitution or Buchwald N-arylation or N-heteroarylation reactions, for example by means of a palladium or copper catalyst, to obtain the intermediate of general formula (IVa), in which A, $R_2$, $R_5$, m, n, $U_2$ and PG are as defined above. The compound (IVa) thus obtained is used, in a first stage, in a deprotection reaction, for example in the presence of trifluoroacetic acid or of a solution of hydrogen chloride (5N) in isopropanol or dioxane, followed by a condensation reaction with a carlamine, in a solvent such as toluene or dichloroethane, at a temperature between room temperature and the reflux temperature of the solvent. The final step consists in performing a coupling reaction catalysed with a transition metal such as palladium(0), on the intermediate of general formula (Ia), in which A, $R_2$, $R_3$, $R_4$, $R_5$, m, n and $U_2$ are as defined above, $U_2$ being in the position in which it is desired to introduce the group $R_6$ or $R_7$:

either via a reaction of Suzuki type, for example using an alkyl, cycloalkyl, aryl or heteroaryl boronic acid, or according to a reaction of Stille type, for example using an aryl or heteroaryl trialkylstannous derivative, or via a reaction of Negishi type, for example using an alkyl, cycloalkyl, aryl or heteroaryl halide zincate derivative.

Scheme 3

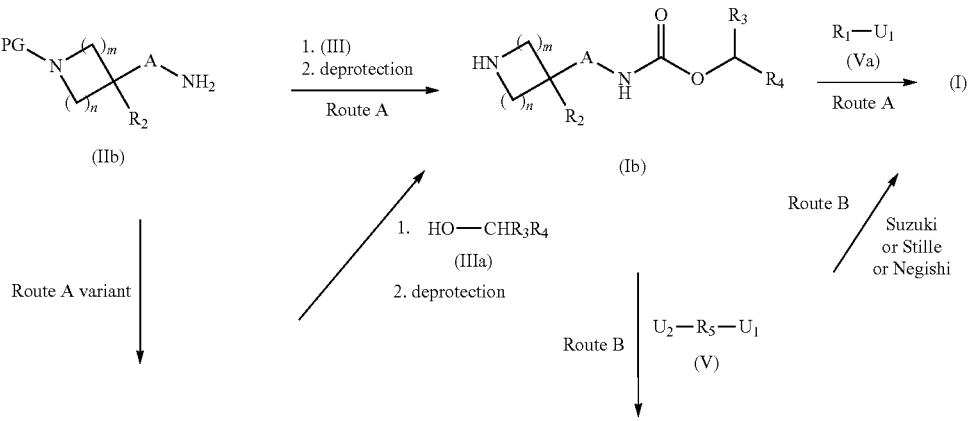

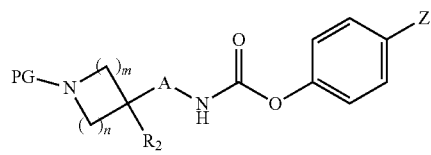

(IVc)

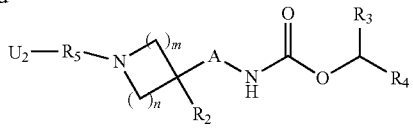

(Ia)

Route B variant

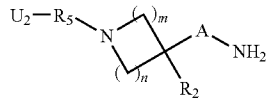

(IIb)

A third method (scheme 3) consists in reacting, in a first stage, an amine of general formula (IIb) in which A, $R_2$, m and n are as defined in the general formula (I) defined above, and PG is as defined above, with a carbonate of general formula (III) as defined above, under the conditions described above for the reaction of the amine of general formula (II) with the carbonate of general formula (III), followed by a deprotection reaction, for example in the presence of a solution of hydrogen chloride (5N) in isopropanol or dioxane, to obtain the intermediate of general formula (Ia), in which A, $R_2$, $R_3$, $R_4$, m and n are as defined in the general formula (I).

One variant for obtaining the intermediates of general formula (Ib) (scheme 3, route A variant) consists in reacting an amine of general formula (IIa), as defined above, with phenyl or 4-nitrophenyl chloroformate, under the conditions described above when the compound of formula (II) reacts with the compound of formula (IV) (scheme 1, variant), to give the carbamate derivative of general formula (IVc), in which A, $R_2$, m and n are as defined in the general formula (I) defined above, and PG and Z are as defined above. The carbamate derivative of general formula (IVc) thus obtained is then converted into a compound of general formula (Ia), via the action of an alcohol of general formula HOCHR$_3$R$_4$ (IIIa), under the conditions described above when the compound of formula (IV) reacts with the compound of formula (IIIa) (scheme 1, variant).

The compound of general formula (I) is then obtained by reaction of the compound of general formula (Ib) with a derivative of general formula (Va), in which $R_1$ and $U_1$ are as defined in the general formula (I), using aromatic or heteroaromatic nucleophilic substitution reaction conditions, for example by means of a base such as triethylamine, diisopropylethylamine, pyridine or N,N-dimethylaminopyridine in a solvent such as dichloromethane, dichloroethane, acetonitrile, N,N-dimethylformamide, dioxane or tetrahydrofuran, at a temperature between 0° C. and the reflux temperature of the solvent. This conversion may also be performed using the Buchwald N-arylation or N-heteroarylation conditions, for example by means of a palladium or copper catalyst.

According to scheme 3, route B, the compounds of general formula (I), in which $R_1$ represents a group $R_5$ substituted especially with a group $R_6$ of the type $C_{1-6}$-alkyl, $C_{3-7}$-cycloalkyl or $C_{3-7}$-cycloalkyl-$C_{1-3}$-alkylene, or with a group $R_7$ as defined in the general formula (I) defined above, may also be prepared according to a coupling reaction, catalysed with a transition metal, for example palladium(0), performed on the compound of general formula (Ia), in which A, $R_2$, $R_3$, $R_4$, $R_5$, m, n, o and p are as defined in the general formula (I) and $U_2$ represents a chlorine, bromine or iodine atom or a triflate group, $U_2$ being in the position in which it is desired to introduce the group $R_6$ or $R_7$ (scheme 3, route B) according to the reaction conditions used for converting the compound of formula (Ia) into a compound of formula (I) (see scheme 2).

The intermediate of general formula (Ia) as defined above is first obtained by reacting an amine of general formula (Ib) as defined above with a derivative of general formula (Vb) in which $R_5$, $U_1$ and $U_2$ are as defined above under the conditions described above in scheme 2 when the compound of formula (IIa) reacts with the compound of formula (V) to give the compound of formula (IVa).

One variant for obtaining the intermediates of general formula (Ia) (scheme 3, route B variant) consists in reacting, in a first stage, an amine of general formula (IIb), in which A, $R_5$, $R_2$, m and n are as defined in the general formula (I) defined above, and $U_2$ is as defined above, with a carbonate of general formula (III) as defined above, under the conditions described above for the reaction of the amine of general formula (II) with the carbonate of general formula (III), to give the intermediate of general formula (Ia), in which A, $R_5$, $R_2$, $R_3$, $R_4$, m and n are as defined in the general formula (I), and $U_2$ is as defined above.

Another subject of the present invention relates to the intermediates of formula (Ib) below:

3-methylcarbamoylisoxazol-5-ylmethyl pyrrolidin-3-ylmethylcarbamate hydrochloride m.p. (° C.): 187-189, LC-MS: M+H=283

$^1$H NMR (DMSO) δ (ppm): 8.70 (bs, 1H); 8.00 (m, 2H); 6.80 (m, 1H); 5.25 (s, 2H); 3.60 (m, 1H); 3.45 (m, 1H); 3.30 (m, 1H); 3.10 (m, 1H); 2.90 (m, 2H); 2.80 (s, 3H); 2.50 (m, 1H); 2.05 (m, 1H) ; 1.70 (m, 1H)

3-methylcarbamoylisoxazol-5-ylmethyl [2-(4-methylpiperidin-4-yl) ethyl]carbamate m.p. (° C.): 188-190, LC-MS: M+H=361

$^1$H NMR (DMSO) δ (ppm): 8.70 (broad s, 1H); 8.50 (broad s, 1H); 7.45 (broad s, 1H); 6.80 (s, 1H); 5.20 (s, 2H); 3.00 (m, 6H); 2.75 (d, 3H); 1.60-1.40 (m, 6H); 0.95 (m, 3H)

3-methylcarbamoylisoxazol-5-ylmethyl [2-(4-isobutylpiperidin-4-yl)ethyl]carbamate

LC-MS: M+H=367

$^1$H NMR (DMSO) δ (ppm): 8.70 (broad s, 1H); 8.50 (broad s, 1H); 7.40 (m, 1H); 6.80 (s, 1H); 5.20 (s, 2H); 3.00 (m, 6H); 2.75 (d, 3H); 1.70 (m, 1H); 1.50 (m, 6H); 1.30 (m, 2H); 0.90 (d, 6H)

3-methylcarbamoylisoxazol-5-ylmethyl [2-(4-ethylpiperidin-4-yl)ethyl]carbamate hydrochloride m.p. (° C.): 222-224, LC-MS: M+H=339

¹H NMR (DMSO) δ (ppm): 8.70 (broad s, 2H); 7.40 (t, 1H); 6.80 (s, 1H); 5.20 (s, 2H); 2.95 (m, 6H); 2.75 (d, 3H); 1.55 (q, 2H); 1.45 (t, 2H); 1.35 (m, 4H); 0.80 (t, 3H).

3-methylcarbamoylisoxazol-5-ylmethyl piperidin-4-ylcarbamate

LC-MS: M+H=283

¹H NMR (DMSO) δ (ppm): 8.80 (bs, 1H); 8.70 (m, 1H); 7.75 (m, 1H); 6.80 (s, 1H); 5.25 (s, 2H); 3.65 (m, 1H); 3.25 (m, 2H); 3.00 (m, 2H); 2.80 (d, 3H); 1.95 (m, 2H); 1.70 (m, 2H).

5-isopropyl[1,2,4]oxadiazol-3-ylmethyl piperidin-4-ylmethylcarbamate

LC-MS: M+H=282

¹H NMR (DMSO) δ (ppm): 7.25 (bt, 1H); 4.90 (s, 2H); 2.80 (m, 2H); 2.70 (m, 2H); 2.30 (m, 2H); 1.40 (m, 2H); 1.30 (m, 1H); 1.10 (d, 6H); 0.85 (m, 2H).

2,2,2-trifluoro-1-(1-methyl-1H-imidazol-2-yl)ethyl [2-(3-dimethylaminoazetidin-3-yl)ethyl]carbamate hydrochloride ¹H NMR (DMSO) δ (ppm): 12.50 (broad s, 1H); 10.00 (broad s, 1H); 9.20 (broad s, 1H); 8.30(t, 1H); 7.60 (s, 1H); 7.30 (s, 1H); 6.80 (m, 1H); 4.50 (m, 2H); 4.10 (m, 2H); 3.90 (s, 3H); 3.40 (m, 2H); 2.70 (s, 6H); 2.15 (m, 2H)

3-methylcarbamoylisoxazol-5-ylmethyl [2-(3-dimethylaminoazetidin-3-yl)ethyl]carbamate hydrochloride m.p. (° C.): 210-212° C.

¹H NMR (DMSO) δ (ppm): 12.50 (broad s, 1H); 9.80 (broad s, 1H); 9.20 (broad s, 1H); 8.80 (broad s, 1H); 7.80 (broad s, 1H); 6.80 (s, 1H); 5.20 (s, 2H); 4.50 (m, 2H); 4.10 (m, 2H); 3.40 (m, 2H); 2.80 (s, 3H); 2.55 (s, 6H); 2.10 (t, 2H)

ethyl 5-(4-fluoropiperidin-4-ylmethylcarbamoyloxymethyl)-isoxazole-3-carboxylate trifluoroacetate 1-methyl-1H-pyrazol-3-ylmethyl (3-piperidin-4-ylpropyl)-carbamate

LC-MS: M+H=281

¹H NMR (DMSO) δ (ppm): 9.10 (bs, 1H); 8.85 (bs, 1H); 7.65 (s, 1H); 7.15 (bs, 1H); 6.20 (s, 1H); 4.90 (s, 2H); 3.80 (s, 3H); 3.20 (m, 2H); 3.00 (m, 2H); 2.80 (m, 2H); 1.80 (m, 2H); 1.50-1.20 (m, 6H).

3-carbamoylisoxazol-5-ylmethyl azepan-4-ylcarbamate.

Another subject of the present invention relates to the intermediates of formula (II) below:

[1-(4-trifluoromethylpyrimidin-2-yl)pyrrolidin-3-yl]-methylamine 4-(2-aminoethyl)-1-(4-trifluoromethylpyrimidin-2-yl)-piperidin-4-ol ¹H NMR (CDCl₃) δ (ppm): 8.40 (d, 1H); 6.60 (d, 1H); 4.50 (m, 2H); 3.50-3.20 (m, 2H); 3.20 (m, 2H); 2.90-2.60 (broad s, 2H); 1.70 (m, 2H); 1.50-1.30 (m, 4H).

2-[5'-(3-fluorophenyl)-3,4,5,6-tetrahydro-2H-[1,2']bipyridinyl-4-yl]ethylamine

2-[1-(4'-fluorobiphenyl-4-yl)piperidin-4-yl]ethylamine

LC-MS: M+H=299

¹H NMR (DMSO) δ (ppm): 7.60 (m, 2H); 7.50 (d, 2H); 7.25 (m, 2H); 7.00 (d, 2H); 3.75 (m, 2H); 2.85 (m, 2H); 2.75 (m, 2H); 1.70 (m, 2H); 1.50 (m, 1H); 1.35 (m, 2H); 1.25 (m, 2H)

2-(5'-isobutyl-3,4,5,6-tetrahydro-2H-[1,2']bipyridinyl-4-yl)ethylamine

LC-MS: M+H=262

¹H NMR (CDCl₃) δ (ppm): 8.00 (m, 1H); 7.30 (m, 1H); 6.65 (d, 1H); 4.25 (m, 2H); 2.80 (m, 4H); 2.35 (m, 2H); 1.80 (m, 3H); 1.60 (m, 1H); 1.45 (m, 2H); 1.30 (m, 4H); 0.90 (d, 6H)

2-{1-[6-(4-fluorophenyl)pyridazin-3-yl]piperidin-4-yl}ethylamine

2-[5'-(2,2-dimethylpropyl)-3,4,5,6-tetrahydro-2H-[1,2']bipyridinyl-4-yl]ethylamine 2-[1-(4-trifluoromethylpyrimidin-2-yl)piperidin-4-yl]-ethylamine 2-{1-[6-(4-fluorophenyl)pyrazin-2-yl]piperidin-4-yl}ethylamine 2-{1-[5-(4-fluorophenyl)pyrimidin-2-yl]piperidin-4-yl}ethylamine 2-[1-(4-trifluoromethylpyrimidin-2-yl)azetidin-3-yl]-ethylamine

LC-MS: M+H=247

¹H NMR (CDCl₃) δ (ppm): 8.50 (d, 1H); 6.80 (d, 1H); 4.30 (m, 2H); 3.90 (m, 2H); 2.85 (m, 1H); 2.75 (m, 2H); 1.85 (m, 2H); 1.30 (bs, 2H).

Another subject of the present invention relates to the intermediates of formula (IIa) below:

tert-butyl 4-(2-aminoethyl)-4-ethylpiperidine-1-carboxylate tert-butyl 4-(2-aminoethyl)-4-isobutylpiperidine-1-carboxylate tert-butyl 3-(2-aminoethyl)-3-dimethylaminoazetidine-1-carboxylate Another subject of the present invention relates to the intermediates of formula (IV) below:

nitrophenyl {2-[5'-(4-fluorophenyl)-3,4,5,6-tetrahydro-2H-[1,2']bipyridinyl-4-yl]ethyl}carbamate 4-nitrophenyl {2-[5'-(3-fluorophenyl)-3,4,5,6-tetrahydro-2H-[1,2']bipyridinyl-4-yl]ethyl}carbamate 4-nitrophenyl [2-(5'-bromo-3,4,5,6-tetrahydro-2H-[1,2']bipyridinyl-4-yl)ethyl]carbamate 4-nitrophenyl {2-[1-(4-trifluoromethylpyrimidin-2-yl)-piperidin-4-yl]ethyl}carbamate 4-nitrophenyl (2-{1-[6-(4-fluorophenyl)pyrazin-2-yl]-piperidin-4-yl}ethyl)carbamate 4-nitrophenyl (2-{1-[5-(4-fluorophenyl)pyrimidin-2-yl]-piperidin-4-yl}ethyl)carbamate 4-nitrophenyl [2-(5'-bromo-3,4,5,6-tetrahydro-2H-[1,2']bipyridinyl-4-yl)ethylcarbamate.

The other compounds of general formulae (II), (IIa), (III), (IIIa) and (V) and also the other reagents are commercially available or described in the literature, or may be prepared according to methods that are described therein or that are known to those skilled in the art.

In particular, the carbonate of general formula (III) may be prepared according to any method described in the literature, for example by reacting an alcohol of general formula HOCHR₃R₄ (IIIa), in which R₃ and R₄ are as defined in the general formula (I) as defined above, with phenyl or 4-nitrophenyl chloroformate, in the presence of a base such as triethylamine, N-methylmorpholine or diisopropylethylamine, in a solvent such as dichloromethane or tetrahydrofuran, at a temperature between 0° C. and room temperature.

The examples that follow illustrate the preparation of a number of compounds of the invention. These examples are not limiting, and serve merely to illustrate the invention. The microanalyses and the IR, NMR and/or LC-MS (liquid chromatography coupled to mass spectroscopy) spectra confirm the structures and the purities of the compounds obtained.

Method A: UPLC/TOF—Gradient 3 min—H₂O/ACN/TFA TO: 98% A—T1.6 to T2.1 min: 100% B—T2.5 to T3 min: 98% A route A: H₂O+0.05% TFA; route B: ACN +0.035% TFA flow rate: 1.0 mL/min-T°=40° C.—Injection 2 μL Acquity BEH C18 (50×2.1 mm; 1.7 μm) column; 220 nm.

Method B: HPLC/ZQ—Gradient 10 min—CH₃COONH₄ 5 mM/ACN T0: 100% A—T5.5 to T7 min: 100% B—T7.1 to T10 min: 100% A a route A: CH₃COONH₄+3% ACN; route B: ACN flow rate: 0.8 mL/min–T°=40° C.—Injection 5 μL Kromasil C18 (50×2.1 mm; 3.5 μm) column; 220 nm.

m.p. (° C.) represents the melting point in degrees Celsius.

The numbers given in parentheses in the example titles correspond to those of the first column of the table hereinbelow.

The IUPAC (International Union of Pure and Applied Chemistry) nomenclature was used to name the compounds in the examples below.

EXAMPLE 1 (COMPOUND 9)

[1,2,3]Thiadiazol-4-ylmethyl 2-[5'-(4-fluorophenyl)-3,4,5,6-tetrahydro-2H-[1,2']bipyridinyl-4-yl]ethylcarbamate

1.1. 2-(5'-Bromo-3,4,5,6-tetrahydro-2H-[1,2']bipyridinyl-4-yl)ethanol 11.00 g (46.43 mmol) of 2,5-dibromopyridine, 6.00 g (46.43 mmol) of piperidin-4-ylethanol and 6.74 g (48.76 mmol) of potassium carbonate in 8 mL of DMSO are placed in an autoclave. The mixture is then heated at 160° C. for 20 hours. The reaction mixture is allowed to cool to room temperature and then taken up in ethyl acetate and water. The aqueous phase is separated out and extracted twice with ethyl acetate, and the combined organic phases are washed with saturated aqueous sodium chloride solution and dried over sodium sulfate, and the filtrate is concentrated under reduced pressure.

11.00 g of product are thus obtained in the form of an oil, which is used in the next step without further purification.

1.2. 2-[5'-(4-Fluorophenyl)-3,4,5,6-tetrahydro-2H-[1,2']bipyridinyl-4-yl]ethanol Under an inert atmosphere, 3.60 g (12.62 mmol) of 2-(5'-bromo-3,4,5,6-tetrahydro-2H-[1,2']bipyridinyl-4-yl)ethanol, prepared in step 1.1., 3.53 g (25.25 mmol) of 4-fluorophenylboronic acid, 5.23 g (37.87 mmol) of potassium carbonate and 4.88 g (15.15 mmol) of tetrabutylammonium bromide in suspension are introduced into 20 mL of water. 0.142 g (0.63 mmol) of Pd(OAc)$_2$ is then added. The reaction mixture is refluxed for 24 hours.

The mixture is allowed to cool to room temperature, the salts are separated out by filtration on Celite, the filtrate is then taken up in ethyl acetate, the aqueous phase is separated out and extracted twice with ethyl acetate, and the combined organic phases are washed with saturated aqueous sodium chloride solution and dried over sodium sulfate. After evaporating off the solvent, the residue obtained is purified by chromatography on silica gel, eluting with a 50/50 mixture of ethyl acetate and cyclohexane.

1.6 g of product are thus obtained in the form of a white powder.

m.p. (° C.)=118-120° C.

1.3. 2-{2-[5'-(4-Fluorophenyl)-3,4,5,6-tetrahydro-2H-[1,2']bipyridinyl-4-yl]ethyl}isoindole-1,3-dione To a solution of 2.00 g (6.66 mmol) of 2-[5'-(4-fluorophenyl)-3,4,5,6-tetrahydro-2H-[1,2]bipyridinyl-4-yl]ethanol, prepared in step 1.2., 2.096 g (7.99 mmol) of triphenylphosphine and 1.077 g (7.32 mmol) of phthalimide in 40 mL of tetrahydrofuran, cooled to about −2° C., is added dropwise under an inert atmosphere a solution of 1.61 g (7.99 mmol) of diisopropyl azodicarboxylate (DIAD) in 4 mL of tetrahydrofuran, while maintaining the temperature of the reaction medium between −2° C. and 0° C. Stirring is continued at 0° C. for 1 hour, and then at room temperature for 12 hours. The mixture is concentrated under reduced pressure, and the residue is taken up in dichloromethane and water. The aqueous phase is separated out and then extracted twice with dichloromethane. The organic phases are combined and washed successively with aqueous hydrochloric acid solution (1N), and then with saturated aqueous sodium hydrogen carbonate solution and saturated aqueous sodium chloride solution. The organic phase is dried over sodium sulfate and the filtrate is concentrated under reduced pressure. The residue thus obtained is purified by chromatography on silica gel, eluting with a 20/80 mixture of ethyl acetate and cyclohexane.

2.1 g of the expected product are thus obtained in the form of a white powder.

m.p. (° C.)=180-182° C.

1.4. 2-[5'-(4-Fluorophenyl)-3,4,5,6-tetrahydro-2H-[1,2']bipyridinyl-4-yl]ethylamine To a solution of 1.3 g (3.03 mmol) of 2-{2-[5'-(4-fluorophenyl)-3,4,5,6-tetrahydro-2H-[1,2']bipyridinyl-4-yl]ethyl}-isoindole-1,3-dione, prepared in step 1.3. in 30 mL of ethanol is added slowly at room temperature 0.485 g (15.13 mmol) of hydrazine monohydrate. The reaction mixture is then refluxed for 3 hours.

The mixture is allowed to cool to room temperature, the insoluble material is separated out by filtration and the filtrate is concentrated under reduced pressure. The residue is taken up in 20 mL of ether and stirred at room temperature for one hour. The insoluble material is again separated out and the filtrate is concentrated under reduced pressure. 0.70 g of the expected product is thus obtained in the form of a white powder.

m.p. (° C.)=88-94° C.

$^1$H NMR (CDCl$_3$) δ (ppm): 8.3 (d, 1H); 7.55 (dd, 1H); 7.35 (m, 2H); 7.05 (d, 1H); 7.1 (d, 1H); 6.65 (d, 1H); 4.25 (broad d, 2H); 3.0-2.8 (m, 4H); 1.8 (m, 2H); 1.6-1.1 (m, 5H).

1.5. 4-Nitrophenyl 2-[5'-(4-fluorophenyl)-3,4,5,6-tetrahydro-2H-[1,2']bipyridinyl-4-yl]ethylcarbamate To a solution of 5 g (16.7 mmol) of 2-[5'-(4-fluorophenyl)-3,4,5,6-tetrahydro-2H-[1,2']bipyridinyl-4-yl]ethylamine, prepared in step 1.4., 4.32 g (33.40 mmol) of N,N-diisopropylethylamine and 0.10 g (0.84 mmol) of N,N-dimethylaminopyridine in 50 mL of dichloromethane, cooled to about 0° C., are added portionwise 3.7 g (18.37 mmol) of 4-nitrophenyl chloroformate. Stirring is continued at 0° C. for 1 hour and then at room temperature for 2 hours.

Water is added to the reaction medium, the aqueous phase is separated out and extracted several times with dichloromethane, and the combined organic phases are washed with saturated aqueous sodium chloride solution and dried over sodium sulfate, and the filtrate is concentrated under reduced pressure.

4.6 g of product are thus obtained in the form of an amorphous beige-coloured solid, which is used in the next step without further purification.

LC-MS: M+H=465

$^1$H NMR (DMSO) δ (ppm): 8.40 (s, 1H); 8.30 (d, 2H); 8.10 (bt, 1H); 7.80 (m, 1H); 7.70 (m, 2H); 7.45 (d, 2H); 7.25 (m, 2H); 6.90 (d, 1H); 4.35 (m, 2H); 3.20 (m, 2H); 2.80 (m, 2H); 1.80 (m, 2H); 1.65 (m, 1H); 1.50 (m, 2H); 1.20 (m, 2H).

1.6. [1,2,3]Thiadiazol-4-ylmethyl 2-[5'-(4-fluorophenyl)-3,4,5,6-tetrahydro-2H-[1,2']bipyridinyl-4-yl]ethylcarbamate A solution of 0.50 g (0.50 mmol) of 4-nitrophenyl 2-[5'-(4-fluorophenyl)-3,4,5,6-tetrahydro-2H-[1,2']bipyridinyl-4-yl]-ethylcarbamate, prepared in step 1.5., 0.128 g (0.99 mmol) of N,N-diisopropylethylamine, 0.030 g (0.25 mmol) of N,N-dimethylaminopyridine and 0.079 g (0.5 mmol) of [1,2,3]thiadiazol-4-ylmethanol (Acta Pharmaceutica Suecica (1973), 10(4), 285-96) in 5 mL of 1,2-dichloroethane is heated in a reactor tube at 80° C. for 12 hours.

The mixture is allowed to cool to room temperature. The residue is taken up in dichloromethane and aqueous 1N sodium hydroxide solution, the aqueous phase is separated out and extracted twice with dichloromethane, the combined organic phases are washed successively with aqueous 1N sodium hydroxide solution and then with saturated aqueous sodium chloride solution, and dried over sodium sulfate. After evaporating off the solvent, the residue obtained is purified by chromatography on silica gel, eluting with a 99/1/0.1 mixture of dichloromethane, methanol and 28% aqueous ammonia. 0.23 g of pure product is thus obtained in the form of a white powder.

m.p. (° C.): 139-141° C.; LC-MS: M+H=442
$^1$H NMR (DMSO) δ (ppm): 9.15 (s, 1H); 8.4 (s, 1H); 7.8 (d, 1H); 7.7 (dd, 2H); 7.40 (broad t, 1H); 7.25 (t, 2H); 6.90 (d, 1H); 5.5 (s, 2H); 4.35 (broad d, 2H); 3.1 (m, 2H); 2.85 (broad t, 2H); 1.75 (broad d, 2H); 1.55 (m, 1H); 1.4 (m, 2H); 1.15 (m, 2H).

EXAMPLE 2 (COMPOUND 5)

3-Ethyl[1,2,4]oxadiazol-5-ylmethyl 2-[5'-(4-fluorophenyl)-3,4,5,6-tetrahydro-2H-[1,2']bipyridinyl-4-yl]ethylcarbamate The process is performed according to the procedure described in Example 1 (step 1.6.). Starting with 0.23 g (0.5 mmol) of 4-nitrophenyl 2-[5'-(4-fluorophenyl)-3,4,5,6-tetrahydro-2H-[1,2']bipyridinyl-4-yl]ethylcarbamate, described in Example 1 (step 1.5.), 0.128 g (0.99 mmol) of N,N-diisopropylethylamine, 0.030 g (0.25 mmol) of N,N-dimethylaminopyridine and 0.067 g (0.50 mmol) of 3-ethyl[1,2,4]oxadiazol-5-ylmethanol, and after chromatography on silica gel, eluting with a 99/1/0.1 mixture of dichloromethane, methanol and 28% aqueous ammonia, 0.138 g of pure product is obtained in the form of a white powder.

m.p. (° C.): 110-112° C., LC-MS: M+H=454
$^1$H NMR (DMSO) δ (ppm): 8.40 (s, 1H); 7.8 (d, 1H); 7.7 (dd, 2H); 7.65 (broad t, 1H); 7.30 (t, 2H); 6.90 (d, 1H); 5.30 (s, 2H); 4.35 (broad d, 2H); 3.1 (m, 2H); 2.85 (broad t, 2H); 2.75 (q, 2H); 1.75 (broad d, 2H); 1.60 (m, 1H); 1.45 (m, 2H); 1.25 (t, 3H); 1.15 (m, 2H).

EXAMPLE 3 (COMPOUND 26)

3-Methylcarbamoylisoxazol-5-ylmethyl 2-[5'-(4-fluorophenyl)-3,4,5,6-tetrahydro-2H-[1,2']bipyridinyl-4-yl]ethylcarbamate The process is performed according to the procedure described in Example 1 (step 1.6.). Starting with 0.20 g (0.43 mmol) of 4-nitrophenyl 2-[5'-(4-fluorophenyl)-3,4,5,6-tetrahydro-2H-[1,2']bipyridinyl-4-yl]ethylcarbamate, described in Example 1 (step 1.5.), 0.122 g (0.95 mmol) of N,N-diisopropylethylamine, 0.026 g (0.22 mmol) of N,N-dimethylaminopyridine and 0.074 g (0.47 mmol) of 3-methylcarbamoylisoxazol-5-ylmethanol, and after chromatography on silica gel, eluting with a 98/2/0.2 mixture of dichloromethane, methanol and 28% aqueous ammonia, 0.170 g of pure product is obtained in the form of a white powder.

m.p. (° C.): 191-193° C., LC-MS: M+H=482
$^1$H NMR (DMSO) δ (ppm): 8.7 (broad s, 1H); 8,40 (s, 1H); 7.85 (d, 1H); 7.65 (dd, 2H); 7.45 (broad t, 1H); 7.30 (t, 2H); 6.90 (d, 1H); 6.8 (s, 1H); 5.20 (s, 2H); 4.35 (broad d, 2H); 3.10 (m, 2H); 2.80 (m, 5H); 1.75 (broad d, 2H); 1.60 (m, 1H); 1.40 (m, 2H); 1.15 (m, 2H).

EXAMPLE 4 (COMPOUND 19)

3-Carbamoylisoxazol-5-ylmethyl 2-[5'-(4-fluorophenyl)-3,4,5,6-tetrahydro-2H-[1,2']bipyridinyl-4-yl]ethylcarbamate A solution of 0.25 g (0.54 mmol) of 4-nitrophenyl 2-[5'-(4-fluorophenyl)-3,4,5,6-tetrahydro-2H-[1,2']bipyridinyl-4-yl]-ethylcarbamate, prepared in step 1.5., 0.139 g (1.08 mmol) of N,N-diisopropylethylamine, 0.033 g (0.27 mmol) of N,N-dimethylaminopyridine and 0.084 g (0.59 mmol) of 3-carbamoylisoxazol-5-ylmethanol in 5 mL of 1,2-dichloroethane is heated in a sealed tube at 90° C. for 12 hours.

The mixture is allowed to cool to room temperature. The precipitate formed in the reaction medium is filtered through a sinter funnel and then rinsed thoroughly with ether and water. The solid is then dried under vacuum at about 80° C. overnight.

0.202 g of pure product is thus obtained in the form of a white powder.

m.p. (° C.): 202-204° C., LC-MS: M+H=468
$^1$H NMR (DMSO) δ (ppm): 8.45 (s, 1H); 8.15 (broad s, 1H); 7.85 (m, 2H); 7.70 (dd, 2H); 7.45 (broad t, 1H); 7.30 (t, 2H); 6.90 (d, 1H); 6.8 (s, 1H); 5.20 (s, 2H); 4.40 (broad d, 2H); 3.10 (m, 2H); 2.85 (broad t, 2H); 1.80 (broad d, 2H); 1.60 (m, 1H); 1.40 (m, 2H); 1.15 (m, 2H).

EXAMPLE 5 (COMPOUND 21)

4-Carbamoyloxazol-2-ylmethyl 2-[5'-(4-fluorophenyl)-3,4,5,6-tetrahydro-2H-[1,2']bipyridinyl-4-yl]ethylcarbamate 5.1. Methyl 2-acetoxymethyloxazole-4-carboxylate To a solution of 1.2 g (4.20 mmol) of methyl 2-bromomethyloxazole-4-carboxylate (US 2005/215 577) in 42 mL of acetonitrile is added at room temperature 0.453 g (4.62 mmol) of potassium acetate and stirring is then continued at room temperature for 12 hours.

After concentrating under reduced pressure, the residue is taken up in dichloromethane and water. The aqueous phase is separated out and then extracted twice with dichloromethane. The organic phases are combined and washed with saturated aqueous sodium chloride solution. The organic phase is dried over sodium sulfate and the filtrate is concentrated under reduced pressure.

1.1 g of the expected product are thus obtained in the form of an oil, which is used in the next step without further purification.

5.2. 4-Carbamoyloxazol-2-ylmethanol 20 mL (352 mmol) of 28% aqueous ammonia are added to a round-bottomed flask containing 0.60 g (3.01 mmol) of methyl 2-acetoxymethyloxazole-4-carboxylate, prepared in step 5.1., and the reaction medium is then stirred at room temperature for 24 hours.

After concentrating under reduced pressure, the residue obtained is purified by chromatography on silica gel, eluting with a 90/10/0.1 mixture of dichloromethane, methanol and 28% aqueous ammonia.

0.230 g of pure product is thus obtained in the form of a white powder.

m.p. (° C.): 148-150° C.

5.3. 4-Carbamoyloxazol-2-ylmethyl 2-[5'-(4-fluorophenyl)-3,4,5,6-tetrahydro-2H-[1,2']bipyridinyl-4-yl]ethylcarbamate The process is performed according to the procedure described in Example 4. Starting with 0.25 g (0.54 mmol) of 4-nitrophenyl 2-[5'-(4-fluorophenyl)-3,4,5,6-tetrahydro-2H-[1,2']bipyridinyl-4-yl]ethylcarbamate, described in Example 1 (step 1.5.), 0.139 g (1.08 mmol) of N,N-diisopropylethylamine, 0.033 g (0.27 mmol) of N,N-dimethylaminopyridine and 0.084 g (0.59 mmol) of 4-carbamoyloxazol-2-ylmethanol, prepared in step 5.2., 0.162 g of pure product is obtained in the form of a white powder.

m.p. (° C.): 206-208° C., LC-MS: M+H=468

$^1$H NMR (DMSO) δ (ppm): 8.60 (s, 1H); 8.40 (s, 1H); 7.80 (dd, 1H); 7.65 (m, 3H); 7.45 (m, 2H); 7.25 (t, 2H); 6.85 (d, 1H); 5.10 (s, 2H); 4.30 (broad d, 2H); 3.10 (m, 2H); 2.75 (broad t, 2H); 1.75 (broad d, 2H); 1.55 (m, 1H); 1.35 (m, 2H); 1.10 (m, 2H).

EXAMPLE 6 (COMPOUND 1)

3-Carbamoylisoxazol-5-ylmethyl 2-[1-(6-chloroquinolin-2-yl)-piperidin-4-yl]ethylcarbamate

6.1. 2-[1-(6-Chloroquinolin-2-yl)piperidin-4-yl]ethyl methanesulfonate

To a solution of 4.00 g (13.76 mmol) of 2-[1-(6-chloroquinolin-2-yl)piperidin-4-yl]ethanol (WO 2004/099 176), 3.55 g (27.51 mmol) of N,N-diisopropylethylamine and 0.84 g (6.88 mmol) of N,N-dimethylaminopyridine in 30 mL of dichloromethane, cooled to about 0° C., is added dropwise, under an inert atmosphere, a solution of 2.36 g (20.63 mmol) of methyl chloride in 3 mL of dichloromethane. Stirring is continued at 0° C. for two hours and then at room temperature for one hour.

Water is added to the reaction medium, the aqueous phase is separated out and extracted several times with dichloromethane, and the combined organic phases are washed with saturated aqueous sodium chloride solution and dried over sodium sulfate, and the filtrate is concentrated under reduced pressure.

5.1 g of product are thus obtained in the form of an oil, which is used in the next step without further purification.

6.2. 2-[4-(2-Azidoethyl)piperidin-1-yl]-6-chloroquinoline

A solution of 5 g (13.55 mmol) of 2-[1-(6-chloroquinolin-2-yl)piperidin-4-yl]ethyl methanesulfonate, prepared in step 6.1., and 1.76 g (27.11 mmol) of sodium azide in 30 mL of N,N-dimethylformamide is refluxed for 4 hours, under an inert atmosphere.

The mixture is allowed to cool to room temperature and then concentrated under reduced pressure. The residue is taken up in dichloromethane and water, the aqueous phase is separated out and extracted twice with dichloromethane, and the combined organic phases are washed with saturated aqueous sodium chloride solution and dried over sodium sulfate. After evaporating off the solvent, 3.8 g of product are obtained in the form of an oil, which is used in the next step without further purification.

6.3. 2-[1-(6-Chloroquinolin-2-yl)piperidin-4-yl]ethylamine

To a solution of 3.50 g (11.08 mmol) of 2-[4-(2-azidoethyl)-piperidin-1-yl]-6-chloroquinoline, obtained in step 6.2., in 100 mL of THF/water (1/1), are added portionwise, at room temperature, 4.36 g (16.62 mmol) of triphenylphosphine. Stirring is continued at room temperature for 10 hours. The mixture is concentrated under reduced pressure. Ethyl acetate is added, the aqueous phase is separated out and extracted three times with ethyl acetate, the combined organic phases are washed with saturated aqueous sodium chloride solution and dried over sodium sulfate, and the filtrate is concentrated under reduced pressure. After chromatography on silica gel, eluting with a 90/10/1 mixture of dichloromethane, methanol and 28% aqueous ammonia, 1.77 g of pure product are obtained in the form of an oil that crystallizes at room temperature.

m.p. (° C.): 68-70° C.

$^1$H NMR (CDCl$_3$) δ (ppm): 7.70 (d, 1H); 7.50 (m, 2H); 7.35 (m, 1H); 6.95 (d, 1H); 4.45 (broad d, 2H); 2.90 (broad td, 2H); 2.70 (t, 2H); 1.70 (m, 2H); 1.60-1.10 (m, 5H).

6.4. 4-Nitrophenyl 2-[1-(6-chloroquinolin-2-yl)piperidin-4-yl]ethylcarbamate The process is performed according to the method described in Example 1 (step 1.5.). Starting with 5.00 g (17.25 mmol) of 2-[1-(6-chloroquinolin-2-yl)piperidin-4-yl]ethylamine, prepared in step 6.3., 3.825 g (18.98 mmol) of 4-nitrophenyl chloroformate, 4.46 g (34.51 mmol) of N,N-diisopropylethylamine and 0.105 p (0.86 mmol) of N,N-dimethylaminopyridine, and after triturating from a mixture of diisopropyl ether and hexane, 7.8 g of pure product are obtained in the form of a white powder.

m.p. (° C.): 80-84° C.

6.5. 3-Carbamoylisoxazol-5-ylmethyl 2-[1-(6-chloroquinolin-2-yl)piperidin-4-yl]ethylcarbamate The process is performed according to the procedure described in Example 4. Starting with 0.50 g (1.10 mmol) of 4-nitrophenyl 2-[1-(6-chloroquinolin-2-yl)piperidin-4-yl]-ethylcarbamate, obtained in step 6.4., 0.284 g (2.2 mmol) of N,N-diisopropylethylamine, 0.067 g (0.55 mmol) of N,N-dimethylaminopyridine and 0.156 g (1.1 mmol) of 3-carbamoylisoxazol-5-ylmethanol, 0.250 g of pure product is obtained in the form of a white powder.

m.p. (° C.): 220-222° C.; LC-MS: M+H=468

$^1$H NMR (DMSO) δ (ppm): 8.15 (broad s, 1H); 8.0 (d, 1H); 7.85 (broad s, 1H); 7.75 (d, 1H); 7.50 (q, 2H); 7.45 (broad t, 1H); 7.30 (d, 1H); 6.80 (s, 1H); 5.20 (s, 2H); 4.50 (broad d, 2H); 3.10 (m, 2H); 2.90 (broad t, 2H); 1.80 (broad d, 2H); 1.60 (m, 1H); 1.40 (m, 2H); 1.15 (m, 2H).

EXAMPLE 7 (COMPOUND 20)

3-Methylcarbamoylisoxazol-5-ylmethyl 2-[1-(6-chloroquinolin-2-yl)piperidin-4-yl]ethylcarbamate

7.1. Ethyl 5-{2-[1-(6-chloroquinolin-2-yl)piperidin-4-yl-ethylcarbamoyloxymethyl}isoxazole-3-carboxylate The process is performed according to the procedure described in Example 1 (step 1.7.). Starting with 0.5 g (1.1 mmol) of 4-nitrophenyl 2-[1-(6-chloroquinolin-2-yl)piperidin-4-yl]-ethylcarbamate, described in Example 6 (step 6.4.), 0.311 g (2.2 mmol) of N,N-diisopropylethylamine, 0.067 g (0.55 mmol) of N,N-dimethylaminopyridine and 0.188 g (1.1 mmol) of ethyl 5-hydroxymethylisoxazole-3-carboxylate, and after chromatography on silica gel, eluting with a 98/2 mixture of dichloromethane and methanol, 0.4 g of pure product is obtained in the form of a white powder.

m.p. (° C.): 113-115° C.
$^1$H NMR (CDCl$_3$) δ (ppm): 7.70 (d, 1H); 7.50 (m, 1H); 7.45 (m, 1H); 7.35 (m, 1H); 6.90 (d, 1H); 6.65 (s, 1H); 5.20 (s, 2H); 4.70 (m, 2H); 4.50-4.30 (m, 5H); 3.20 (m, 2H); 2.90 (broad t, 2H); 1.80 (broad d, 2H); 1.60-1.20 (m, 6H).

7.2. 3-Methylcarbamoylisoxazol-5-ylmethyl 2-[1-(6-chloroquinolin-2-yl)piperidin-4-yl]ethylcarbamate To a solution of 0.17 g (0.35 mmol) of ethyl 5-{2-[1-(6-chloroquinolin-2-yl)piperidin-4-ylethylcarbamoyloxymethyl}-isoxazole-3-carboxylate, prepared in step 7.1., in 5 mL of a 5/1 mixture of methanol and dichloromethane is added at room temperature 1 mL (6.98 mmol) of a solution of methylamine (7M) in tetrahydrofuran. Stirring is continued at about 50° C. for 2 hours.

The mixture is allowed to cool to room temperature and then cooled in an ice bath. The precipitate thus formed is filtered off and then rinsed thoroughly with ether. After drying under vacuum at about 70° C., 0.12 g of pure product is obtained in the form of a white powder.

m.p. (° C.): 200-202° C., LC-MS: M+H=472
$^1$H NMR (DMSO) δ (ppm): 8.70 (broad s, 1H); 8.0 (d, 1H); 7.80 (s, 1H); 7.55 (q, 2H); 7.45 (broad t, 1H); 7.30 (d, 1H); 6.80 (s, 1H); 5.20 (s, 2H); 4.50 (broad d, 2H); 3.10 (m, 2H); 2.90 (broad t, 2H); 2.80 (d, 3H); 1.80 (broad d, 2H); 1.60 (m, 1H); 1.40 (m, 2H); 1.15 (m, 2H).

EXAMPLE 8 (COMPOUND 23)

3-Carbamoylisoxazol-5-ylmethyl 2-[1-(6-fluoroquinolin-2-yl)-piperidin-4-yl]ethylcarbamate

8.1. tert-Butyl 2-[1-(6-fluoroquinolin-2-yl)piperidin-4-yl]-ethylcarbamate 2.18 g (9.64 mmol) of 2-bromo-6-fluoroquinoline, 2.00 g (8.76 mmol) of Cert-butyl 2-piperidin-4-ylethylcarbamate, 2.08 g (26.28 mmol) of pyridine and 15 mL of acetonitrile are introduced into a sealed tube. The mixture is then heated at 80° C. for 12 hours.

The mixture is allowed to cool to room temperature and then cooled in an ice bath. The precipitate thus formed is filtered off and then rinsed thoroughly with ether. After drying under vacuum at about 50° C., 2.00 g of pure product are obtained in the form of a white powder.

m.p. (° C.): 127-129° C.

8.2. 2-[1-(6-Fluoroquinolin-2-yl)piperidin-4-yl]ethylamine hydrochloride

To a solution of 1.9 g (5.09 mmol) of Cert-butyl 2-[1-(6-fluoroquinolin-2-yl)piperidin-4-yl]ethylcarbamate, obtained in step 8.1., in 6 mL of dichloromethane, cooled in an ice/water bath, are added slowly 10 mL (40 mmol) of a 4N solution of hydrogen chloride in dioxane. Stirring is continued at room temperature for 2 hours.

After evaporating under reduced pressure, 0.9 g of product is obtained in hydrochloride form, which is used without further purification in step 8.4. below.

8.3. 3-Carbamoylisoxazol-5-ylmethyl 4-nitrophenylcarbonate

To a solution of 2.00 g (14.07 mmol) of 3-carbamoylisoxazol-5-ylmethanol, 1.71 mL (21.11 mmol) of pyridine and 0.172 g (1.41 mmol) of N,N-dimethylaminopyridine in 15 mL of dichloromethane, cooled to about 0° C., are added portionwise 2.84 g (14.07 mmol) of 4-nitrophenyl chloroformate. Stirring is continued at 0° C. for 1 hour and then at room temperature for 1 hour.

The precipitate thus formed is filtered off and then rinsed thoroughly with diisopropyl ether. After drying under vacuum at about 60° C., 3.12 g of product are obtained in the form of a white solid, which is used in the next step without further purification.

m.p. (° C.): 143-145° C.
$^1$H NMR (DMSO) δ (ppm): 8.40 (d, 2H); 8.25 (broad s, 1H); 7.90 (broad s, 1H); 7.65 (d, 2H); 7.0 (s, 1H); 5.50 (s, 2H).

8.4. 3-Carbamoylisoxazol-5-ylmethyl 2-[1-(6-fluoroquinolin-2-yl)piperidin-4-yl]ethylcarbamate The process is performed according to the procedure described in Example 1 in step 1.6. Starting with 0.30 g (0.87 mmol) of 2-[1-(6-fluoroquinolin-2-yl)piperidin-4-yl]ethylamine hydrochloride, obtained in step 8.2., 0.266 g (0.87 mmol) of 3-carbamoylisoxazol-5-ylmethyl 4-nitrophenylcarbonate, obtained in step 8.3., 0.367 g (2.6 mmol) of N,N-diisopropylethylamine and 0.053 g (0.43 mmol) of N,N-dimethylaminopyridine, 0.260 g of pure product is obtained in the form of a white powder.

m.p. (° C.): 200-202° C., LC-MS: M+H=442
$^1$H NMR (DMSO) δ (ppm): 8.15 (broad s, 1H); 8.05 (d, 1H); 7.80 (broad s, 1H); 7.55 (dd, 1H); 7.50 (dd, 1H); 7.40 (m, 2H); 7.30 (d, 1H); 6.75 (s, 1H); 5.20 (s, 2H); 4.50 (broad d, 2H); 3.10 (m, 2H); 2.90 (broad t, 2H); 1.75 (broad d, 2H); 1.60 (m, 1H); 1.40 (m, 2H); 1.15 (m, 2H).

EXAMPLE 9 (COMPOUND 25)

3-Methylcarbamoylisoxazol-5-ylmethyl 2-[1-(6-fluoroquinolin-2-yl)piperidin-4-yl]ethylcarbamate

9.1. 3-Methylcarbamoylisoxazol-5-ylmethyl 4-nitrophenylcarbonate

The process is performed according to the procedure described in Example 8 (step 8.3.). Starting with 2 g (12.81 mmol) of 3-methylcarbamoylisoxazol-5-ylmethanol, 2.58 g (12.81 mmol) of 4-nitrophenyl chloroformate, 1.52 g (19.21 mmol) of pyridine and 0.157 g (1.28 mmol) of N,N-dimethylaminopyridine, 2.6 g of pure product is obtained in the form of a white powder.

m.p. (° C.): 166-168° C.

$^1$H NMR (CDCl$_3$) δ (ppm): 8.40 (d, 2H); 7.50 (d, 2H); 7.0 (s, 1H); 6.90 (broad s, 1H); 5.50 (s, 2H); 3.10 (d, 3H).

9.2. 3-Methylcarbamoylisoxazol-5-ylmethyl 2-[1-(6-fluoro-quinolin-2-yl)piperidin-4-yl]ethylcarbamate The process is performed according to the procedure described in Example 1 (step 1.6.). Starting with 0.310 g (1.13 mmol) of 2-[1-(6-fluoroquinolin-2-yl)piperidin-4-yl]ethylamine, obtained in step 8.2., 0.383 g (1.19 mmol) of 3-methylcarbamoylisoxazol-5-ylmethyl 4-nitrophenylcarbonate, obtained in step 9.1. and 0.32 g (2.27 mmol) N,N-diisopropylethylamine, 0.33 g of pure product is obtained in the form of a white powder.

m.p. (° C.): 180-182° C., LC-MS: M+H=456

$^1$H NMR (DMSO) δ (ppm): 8.70 (broad s, 1H); 8.0 (d, 1H); 7.55 (dd, 1H); 7.50 (dd, 1H); 7.40 (m, 2H); 7.30 (d, 1H); 6.80 (s, 1H); 5.20 (s, 2H); 4.50 (broad d, 2H); 3.10 (m, 2H); 2.85 (broad t, 2H); 2.75 (d, 3H); 1.75 (broad d, 2H); 1.60 (m, 1H); 1.40 (m, 2H); 1.15 (m, 2H).

EXAMPLE 10 (COMPOUND 28)

3-Carbamoylisoxazol-5-ylmethyl 2-[5'-(3-fluorophenyl)-3,4,5,6-tetrahydro-2H-[1,2']bipyridinyl-4-yl]ethylcarbamate

10.1. tert-Butyl 2-(5'-bromo-3,4,5,6-tetrahydro-2H-[1,2']bipyridinyl-4-yl)ethylcarbamate 10.37 g (43.80 mmol) of 2,5-dibromopyridine, 10.00 g (43.80 mmol) of tert-butyl 2-piperidin-4-ylethylcarbamate and 6.05 g (43.80 mmol) of potassium carbonate are placed in an autoclave. The mixture is then heated at 130° C. for 12 hours. The reaction mixture is allowed to cool to room temperature and then taken up in chloroform and saturated aqueous sodium hydrogen carbonate solution. The aqueous phase is separated out and extracted twice with chloroform, and the combined organic phases are washed with saturated aqueous sodium chloride solution and dried over sodium sulfate, and the filtrate is concentrated under reduced pressure.

After chromatography on silica gel, eluting with a 95/5 mixture of dichloromethane and methanol, 6.9 g of pure product is obtained in the form of a white powder.

m.p. (° C.): 108-110° C.

10.2. 2-(5'-Bromo-3,4,5,6-tetrahydro-2H-[1,2']bipyridinyl-4-yl)ethylamine

To a solution of 6.90 g (17.95 mmol) of tert-butyl 2-(5'-bromo-3,4,5,6-tetrahydro-2H-[1,2']bipyridinyl-4-yl)ethylcarbamate, obtained in step 10.1., in 100 mL of dichloromethane, cooled in an ice/water bath, are added slowly 20.47 g (179.54 mmol) of trifluoroacetic acid. Stirring is continued at room temperature for 2 hours. The reaction mixture is poured into a mixture of ice-water and 28% aqueous ammonia. The phases are separated by settling, the aqueous phase is extracted twice with dichloromethane, and the combined organic phases are washed with saturated aqueous sodium chloride solution, dried over sodium sulfate and concentrated under reduced pressure.

4.9 g of product are obtained in the form of an oil, which is used in the next step without further purification.

10.3. 4-Nitrophenyl [2-(5'-bromo-3,4,5,6-tetrahydro-2H-[1,2']bipyridinyl-4-yl)ethylcarbamate The process is performed according to the method described in Example 1 (step 1.5.). Starting with 3.00 g (10.56 mmol) of 2-(5'-bromo-3,4,5,6-tetrahydro-2H-[1,2']bipyridinyl-4-yl)-ethylamine, prepared in step 10.2., 2.34 g (11.61 mmol) of 4-nitrophenyl chloroformate, 3.41 g (26.39 mmol) of N,N-diisopropylethylamine and 0.129 g (1.06 mmol) of N,N-dimethylaminopyridine, and after triturating in disopropylether, 3.27 g of product are obtained in the form of an amorphous solid.

10.4. 3-Carbamoylisoxazol-5-ylmethyl 2-(5'-bromo-3,4,5,6-tetrahydro-2H-[1,2']bipyridinyl-4-yl)ethylcarbamate The process is performed according to the procedure described in Example 4. Starting with 1.00 g (2.23 mmol) of 4-nitrophenyl [2-(5'-bromo-3,4,5,6-tetrahydro-2H-[1,2']bipyridinyl-4-yl)ethylcarbamate, obtained in step 10.3., 0.575 g (4.45 mmol) of N,N-diisopropylethylamine, 0.136 g (1.11 mmol) of N,N-dimethylaminopyridine and 0.381 g (2.67 mmol) of 5-hydroxymethylisoxazole-3-carboxamide, and after triturating with ethyl ether, 0.740 g of pure product is obtained in the form of a white powder.

m.p. (° C.): 164-166° C.

10.5. Carbamoylisoxazol-5-ylmethyl 2-[5'-(3-fluorophenyl)-3,4,5,6-tetrahydro-2H-[1,2']bipyridinyl-4-yl]ethylcarbamate 0.735 g (1.63 mmol) of 3-carbamoylisoxazol-5-ylmethyl 2-(5'-bromo-3,4,5,6-tetrahydro-2H-[1,2']bipyridinyl-4-yl) ethylcarbamate, obtained in step 10.4., 0.256 g (1.83 mmol) of 3-fluorophenylboronic acid and 1.493 g (4.58 mmol) of caesium carbonate suspended in 8 mL of a 9/1 mixture of tetrahydrofuran and water are placed under an inert atmosphere. 0.125 g (0.15 mmol) of PdCl$_2$dppf.CH$_2$Cl$_2$ is then added. The mixture is then heated at about 80° C. for 18 hours.

The mixture is allowed to cool to room temperature, the salts are separated out by filtration on Celite, the filtrate is then taken up in ethyl acetate and water, the aqueous phase is separated out and extracted twice with ethyl acetate, and the combined organic phases are washed with saturated aqueous sodium chloride solution and dried over sodium sulfate. After evaporating off the solvent, the brown gum obtained is triturated in diisopropyl ether. The green solid obtained is then filtered off and dried under vacuum at about 80° C. 0.651 g of product is obtained.

m.p. (° C.): 172-176° C., LC-MS: M+H=468

$^1$H NMR (DMSO) δ (ppm): 8.50 (s, 1H); 8.15 (broad s, 1H); 7.90 (dd, 1H); 7.80 (broad s, 1H); 7.70-7.40 (m, 4H); 7.15 (m, 1H); 6.90 (d, 1H); 6.80 (s, 1H); 5.20 (s, 2H); 4.35 (broad d, 2H); 3.10 (m, 2H); 2.85 (broad t, 2H); 1.80 (broad d, 2H); 1.60 (m, 1H); 1.40 (m, 2H); 1.15 (m, 2H).

EXAMPLE 11 (COMPOUND 53)

2-[1-(6-Chloroquinolin-2-yl)piperidin-4-yl]ethylcarbamoyloxymethyl}isoxazole-3-carboxylic acid

11.1. tert-Butyl {2-[1-(6-chloroquinolin-2-yl)piperidin-4-yl]-ethyl}carbamate 2.00 g (8.76 mmol) of tert-butyl 2-piperidin-4-ylethyl)-carbamate (commercial), 1.73 g (8.76 mmol) of 2,6-dichloroquinoline (commercial) and 1.27 g (36.79 mmol) of potassium carbonate in 11 mL of DMSO are introduced into a sealed tube. The mixture is then heated at 130° C. for 12 hours. The reaction mixture is allowed to cool to room temperature and then taken up in dichloromethane and water. The aqueous phase is separated out and extracted twice with dichloromethane, and the combined organic phases are washed with saturated aqueous ammonium chloride solution and dried over sodium sulfate, and the filtrate is concentrated under reduced pressure. After evaporating off the solvent, the residue obtained is purified by chromatography on silica gel, eluting with a 98/2/0.2 mixture of dichloromethane, methanol and 28% aqueous ammonia. 3.40 g of pure product are obtained in the form of a powder.

LC-MS: M+H=390 m.p. (° C.): 120-122° C.

$^1$H NMR (CDCl$_3$) δ (ppm): 7.80 (d, 1H); 7.65 (d, 1H); 7.60 (s, 1H); 7.40 (d, 1H); 7.00 (d, 1H); 4.50 (broad d, 3H); 3.25 (m, 2H); 2.90 (m, 2H); 1.90 (d, 2H); 1.65 (m, 1H); 1.45 (m, 11H); 1.25 (m, 2H).

11.2. 2-[1-(6-Chloroquinolin-2-yl)piperidin-4-yl]ethylamine

To a solution of 10.95 g (28.08 mmol) of tert-butyl {2-[1-(6-chloroquinolin-2-yl)piperidin-4-yl]ethyl}carbamate, obtained in step 11.1., in 10 mL of dioxane, cooled in an ice/water bath, are added slowly 28 mL (112.00 mmol) of a 4N solution of hydrogen chloride in dioxane. Stirring is continued at room temperature for 3 hours. After filtering through a sinter funnel, the product is obtained in hydrochloride form and is then basified by treatment with 35% sodium hydroxide. After extracting with dichloromethane and then drying over sodium sulfate and evaporating to dryness, 8.13 g of a white powder are obtained.

LC-MS: M+H=290 m.p. (° C.): 118-120° C.

$^1$H NMR (CDCl$_3$) δ (ppm): 7.80 (d, 1H); 7.65 (d, 1H); 7.60 (s, 1H); 7.45 (d, 1H); 7.00 (d, 1H); 4.50 (broad d, 2H); 3.00 (m, 2H); 2.80 (t, 2H); 1.85 (d, 2H); 1.65 (m, 1H); 1.50 (m, 2H); 1.30-1.10 (m, 4H).

11.3. Ethyl 5-{2-[1-(6-chloroquinolin-2-yl)piperidin-4-yl]-ethylcarbamoyloxymethyl}isoxazole-3-carboxylate To a solution of 3.54 g (20.70 mmol) of ethyl 5-hydroxymethylisoxazole-3-carboxylate (commercial), 7.88 mL (41.41 mmol) of N,N-diisopropylethylamine and 1.26 g (10.35 mmol) of N,N-dimethylaminopyridine in 120 mL of dichloromethane, cooled to 0° C., are added portionwise 4.17 g (20.70 mmol) of p-nitrophenyl chloroformate. The mixture is stirred at 10° C. for 2 hours and then evaporated to dryness. The residue obtained is taken up in 120 mL of 1,2-dichloroethane, followed by addition of 6.00 g (20.70 mmol) of 2-[1-(6-chloroquinolin-2-yl)piperidin-4-yl]ethylamine, obtained in step 11.2. and 5 mL (26.27 mmol) of N,N-diisopropylethylamine. The mixture is heated at 70° C. for 12 hours.

After cooling to room temperature, the insoluble material is filtered off and aqueous 1N sodium hydroxide solution is added to the filtrate. The product is then extracted with dichloromethane. The combined organic phases are washed successively with saturated aqueous ammonium chloride solution, and then with saturated aqueous sodium chloride solution. After drying the organic phases over sodium sulfate, the resulting solution is concentrated under reduced pressure. After purifying on a column of silica gel, eluting with a 98/2/0.2 mixture of dichloromethane, methanol and 28% aqueous ammonia, the product is triturated in diisopropyl ether to obtain 5.10 g of expected product in the form of a white solid.

m.p. (° C.): 113-115° C.

$^1$H NMR (CDCl$_3$) δ (ppm): 7.70 (d, 1H); 7.50 (m, 1H); 7.45 (m, 1H); 7.35 (m, 1H); 6.90 (d, 1H); 6.65 (s, 1H); 5.20 (s, 2H); 4.70 (m, 2H); 4.50-4.30 (m, 5H); 3.20 (m, 2H); 2.90 (broad t, 2H); 1.80 (broad d, 2H); 1.60-1.20 (m, 6H).

11.4. 5-{2-[1-(6-Chloroquinolin-2-yl)piperidin-4-yl]ethylcarbamoyloxymethyl}isoxazole-3-carboxylic acid To a solution of 1.00 g (2.05 mmol) of ethyl 5-{2-[1-(6-chloroquinolin-2-yl)piperidin-4-yl]ethylcarbamoyloxymethyl}-isoxazole-3-carboxylate, obtained in step 11.3., in 51 mL of ethanol are added 10.27 mL (10.27 mmol) of aqueous sodium hydroxide solution (1N). The mixture is stirred at room temperature for 2 hours. After evaporating to dryness, the residue is taken up in a minimum amount of water, followed by adding, at 0° C., aqueous 1N hydrochloric acid solution to pH 4-5. After separation of the phases by settling, the oil obtained is triturated in acetone to obtain 0.45 g of expected product in the form of a white solid.

m.p. (° C.): 180-182° C., LC-MS: M+H=459

$^1$H NMR (DMSO) δ (ppm): 8.40 (broad s, 1H); 8.00 (broad s, 2H); 7.85 (broad s, 1H); 7.75 (d, 1H); 7.55 (d, 1H); 6.85 (s, 1H); 5.20 (s, 2H); 4.50 (broad d, 2H); 3.55 (m, 2H); 3.10 (m, 2H); 1.90 (m, 2H); 1.70 (m, 1H); 1.40 (m, 2H); 1.25 (m, 2H).

EXAMPLE 12 (COMPOUND 60)

3-Methylcarbamoylisoxazol-5-ylmethyl {2-[3-dimethylamino-1-(4-trifluoromethylpyrimidin-2-yl)azetidin-3-yl]ethyl}carbamate

12.1. tert-butyl 3-cyanomethyl-3-dimethylaminoazetidine-1-carboxylate 1.20 g (6,18 mmol) of tert-butyl 3-cyanomethyleneazetidine-1-carboxylate (WO 2009/064 835) are dissolved in 15 mL of methanol in a sealed tube. 6.18 mL (12.36 mmol) of a solution of dimethylamine in methanol are added and the reaction medium is stirred at 80° C. for 3 hours.

The mixture is allowed to cool to room temperature and then evaporated to dryness. The residue obtained is chromatographed on a column of silica gel, eluting with a 97/3/0.3 mixture of dichloromethane, methanol and 28% aqueous ammonia to give 1.32 g of expected product in the form of an oil.

LC-MS: M+H=240

$^1$H NMR (DMSO) δ (ppm): 3.75 (m, 4H); 2.90 (s, 2H); 2.15 (s, 6H); 1.40 (s, 9H).

12.2. tert-Butyl 3-(2-aminoethyl)-3-dimethylaminoazetidine-1-carboxylate

To a solution of 1.30 g (5.43 mmol) of tert-butyl 3-cyanomethyl-3-dimethylaminoazetidine-1-carboxylate, obtained in the preceding step, in 27 mL of methanol are added 1.59 g (27.16 mmol) of Raney nickel. The reaction medium is placed in a Parr bomb under a hydrogen atmosphere (70 psi) at 50° C. for 6 hours. The resulting mixture is filtered through a Büchner funnel and the filtrate is then concentrated under reduced pressure. 1.28 g of expected product are thus obtained in the form of a colourless oil.

$^1$H NMR (CDCl$_3$) δ (ppm): 3.90 (d, 2H); 3.60 (d, 2H); 2.90 (m, 2H); 2.25 (s, 6H); 2.10 (m, 2H); 1.90 (m, 2H); 1.40 (s, 9H).

12.3. tert-Butyl 3-dimethylamino-3-[2-(3-methylcarbamoyl-isoxazol-5-ylmethoxycarbonylamino)ethyl]azetidine-1-carboxylate A solution containing 0.60 g (2.47 mmol) of tert-butyl 3-(2-aminoethyl)-3-dimethylaminoazetidine-1-carboxylate obtained in step 12.2., 0.87 g (2.71 mmol) of 3-(methylcarbamoyl)isoxazol-5-ylmethyl 4-nitrophenylcarbonate obtained in step 9.2., 860 µL (4.93 mmol) of N,N-diisopropylethylamine and 0.15 g (1.23 mmol) of N,N-dimethylaminopyridine in 12 mL of 1,2-dichloroethane is heated at 80° C. for 3 hours.

Water is added to the reaction medium, the aqueous phase is separated out and extracted several times with dichloromethane, and the combined organic phases are washed with aqueous sodium hydroxide solution (1N) and then with saturated aqueous ammonium chloride solution. The resulting solution is dried over sodium sulfate and the filtrate is concentrated under reduced pressure.

After evaporating off the solvent, the residue obtained is purified by chromatography on silica gel, eluting with a 97/3/0.3 mixture of dichloromethane, methanol and 28% aqueous ammonia to give 0.64 g of expected product in the form of a wax.

LC-MS: M+H=426

$^1$H NMR (DMSO) δ (ppm): 8.70 (broad s, 1H); 7.40 (broad s, 1H); 6.80 (s, 1H); 5.20 (s, 2H); 3.80 (m, 2H); 3.60 (m, 2H); 3.10 (m, 2H); 2.80 (s, 3H); 2.15 (s, 6H); 1.80 (m, 2H); 1.40 (s, 9H).

12.4. [2-(3-Dimethylaminoazetidin-3-yl)ethyl]carbamate 3-methylcarbamoylisoxazol-5-ylmethyl hydrochloride (2:1)

The process is performed according to the procedure described in Example 11 (step 11.2.). Starting with 0.58 g (1.36 mmol) of tert-butyl 3-dimethylamino-3-[2-(3-methylcarbamoylisoxazol-5-ylmethoxycarbonylamino)ethyl]azetidine-1-carboxylate, obtained in step 12.3., and 4 mL (16 mmol) of a 4N solution of hydrogen chloride in dioxane, and after triturating with ether, 1.27 g of expected product are obtained in the form of a white powder.

m.p. (° C.): 210-212° C.

$^1$H NMR (DMSO) δ (ppm): 12.50 (broad s, 1H); 9.80 (broad s, 1H); 9.20 (broad s, 1H); 8.80 (broad s, 1H); 7.80 (broad s, 1H); 6.80 (s, 1H); 5.20 (s, 2H); 4.50 (m, 2H); 4.10 (m, 2H); 3.40 (m, 2H); 2.80 (s, 3H); 2.55 (s, 6H); 2.10 (t, 2H).

12.5. 3-Methylcarbamoylisoxazol-5-ylmethyl {2-[3-dimethylamino-1-(4-trifluoromethylpyrimidin-2-yl)azetidin-3-yl]ethyl}-carbamate 0.40 g (1.00 mmol) of 3-methylcarbamoylisoxazol-5-ylmethyl) [2-(3-dimethylaminoazetidin-3-yl)ethyl]carbamate hydrochloride (2:1) prepared in the preceding step, 0.20 g (1.10 mmol) of 2-chloro-4-trifluoromethylpyrimidine and 700 µL (4.02 mmol) of N,N-diisopropylethylamine are dissolved in 5 mL of acetonitrile in a microwave reactor (Biotage Initiator™ 2.0 model). The reaction medium is subjected to microwave irradiation for 10 minutes at 130° C.

The mixture is allowed to cool to room temperature and water is then added to the reaction medium. The aqueous phase is separated out and extracted several times with dichloromethane, and the combined organic phases are washed with saturated aqueous ammonium chloride solution. The resulting solution is dried over sodium sulfate and the filtrate is concentrated under reduced pressure.

The residue obtained is purified by chromatography on silica gel, eluting with a 97/3/0.3 mixture of dichloromethane, methanol and 28% aqueous ammonia, and, after triturating in diisopropyl ether and filtering, 0.38 g of expected product is obtained in the form of a white powder.

m.p. (° C.): 154-156° C., LC-MS: M+H=472

$^1$H NMR (DMSO) δ (ppm): 8.70 (broad s, 2H); 7.45 (t, 1H); 7.10 (m, 1H); 6.80 (s, 1H); 5.20 (s, 2H); 4,10 (d, 2H); 3.80 (d, 2H); 3.10 (m, 2H); 2.80 (s, 3H); 2.20 (s, 6H); 1.90 (m, 2H).

EXAMPLE 13 (COMPOUND 63)

2,2,2-Trifluoro-1-(1-methyl-1H-imidazol-2-yl)ethyl {2-[1-(4-chlorophthalazin-1-yl)-3-dimethylaminoazetidin-3-yl]ethyl}-carbamate

13.1. tert-Butyl 3-dimethylamino-3-{2-[2,2,2-trifluoro-1-(1-methyl-1H-imidazol-2-yl)ethoxycarbonylamino]ethyl}azetidine-1-carboxylate To a solution of 0.60 g (2.47 mmol) of tert-butyl 3-(2-aminoethyl)-3-dimethylaminoazetidine-1-carboxylate, prepared in step 12.2., 0.95 g (7.40 mmol) of N,N-diisopropylethylamine and 0.06 g (0.49 mmol) of N,N-dimethylaminopyridine in 12 mL of 1,2-dichloroethane, cooled to about 0° C., is added portionwise 0.497 g (2.47 mmol) of 4-nitrophenyl chloroformate dissolved in 3 mL of 1,2-dichloroethane. Stirring is continued at room temperature for 1 hour. 0.488 g (2.71 mmol) of 2,2,2-trifluoro-1-(1-methyl-1H-imidazol-2-yl)ethanol (commercial) and 0.47 g (3.70 mmol) of N,N-diisopropylethylamine are then added. The mixture is heated at 80° C. for 12 hours.

After cooling to room temperature, water is added to the reaction medium, the aqueous phase is separated out and extracted several times with dichloromethane, and the combined organic phases are washed with aqueous sodium hydroxide solution (1N) and then with saturated aqueous ammonium chloride solution. The resulting solution is dried over sodium sulfate and the filtrate is concentrated under reduced pressure.

After purifying on a column of silica gel, eluting with a 97/3/0.3 mixture of dichloromethane, methanol and 28% aqueous ammonia, 0.71 g of expected product is obtained in the form of a wax.

LC-MS: M+H=450

$^1$H NMR (DMSO) δ (ppm): 7.85 (t, 1H); 7.25 (s, 1H); 7.00 (s, 1H); 6.45 (m, 1H); 3.75 (m, 5H); 3.50 (m, 2H); 3.10 (m, 2H); 2.15 (s, 6H); 1.85 (t, 2H); 1.40 (s, 9H).

13.2. 2,2,2-Trifluoro-1-(1-methyl-1H-imidazol-2-yl)ethyl [2-(3-dimethylaminoazetidin-3-yl)ethyl]carbamate hydrochloride (2:1)

The process is performed according to the procedure described in Example 11 (step 11.2.). Starting with 0.71 g (1.58 mmol) of tert-butyl 3-dimethylamino-3-{2-[2,2,2-trifluoro-1-(1-methyl-1H-imidazol-2-yl)ethoxycarbonylamino]ethyl}azetidine-1-carboxylate, obtained in step 13.1., and 3.90 mL (15.75 mmol) of a 4N solution of hydrogen chloride in dioxane, and after triturating with ether, 0.84 g of the expected product is obtained in the form of an amorphous solid.

¹H NMR (DMSO) δ (ppm): 12.50 (broad s, 1H); 10.00 (broad s, 1H); 9.20 (broad s, 1H); 8.30 (t, 1H); 7.60 (s, 1H); 7.30 (s, 1H); 6.80 (m, 1H); 4.50 (m, 2H); 4.10 (m, 2H); 3.90 (s, 3H); 3.40 (m, 2H); 2.70 (s, 6H); 2.15 (m, 2H).

13.3. 2,2,2-Trifluoro-1-(1-methyl-1H-imidazol-2-yl)ethyl {2-[1-(4-chlorophthalazin-1-yl)-3-dimethylaminoazetidin-3-yl]-ethyl}carbamate The process is performed according to the procedure described in Example 12 (step 12.5.). Starting with 0.50 g (1.09 mmol) of 2,2,2-trifluoro-1-(1-methyl-1H-imidazol-2-yl)ethyl [2-(3-dimethylaminoazetidin-3-yl)ethyl]carbamate hydrochloride (2:1) obtained in the preceding step 13.2., 0.26 g (1.31 mmol) of 1,4-dichlorophthalazine (commercial) and 0.70 g (5.45 mmol) of N,N-diisopropylethylamine in 5.45 mL of acetonitrile, 0.185 g of expected product is obtained in the form of a powder.

m.p. (° C.): 168-170° C., LC-MS: M+H=512,
¹H NMR (DMSO) δ (ppm): 8.20 (m, 2H); 8.05 (m, 1H); 7.90 (m, 1H); 7.80 (broad s, 1H); 7.20 (m, 1H); 6.90 (s, 1H); 6.40 (m, 1H); 4.40 (broad s, 2H); 4.20 (broad s, 2H); 3.70 (s, 3H); 3.20 (m, 2H); 2.30 (m, 6H); 1.95 (m, 2H).

EXAMPLE 14 (COMPOUND 56)

Ethyl 5-[1-(6-chloroquinolin-2-yl)-4-fluoropiperidin-4-ylmethylcarbamoyloxymethyl]isoxazole-3-carboxylate

14.1. Ethyl 5-(4-nitrophenoxycarbonyloxymethyl)isoxazole-3-carboxylate

The process is performed according to the procedure described in Example 8 (step 8.3.). Starting with 3.00 g (17.53 mmol) of ethyl 5-hydroxyethylisoxazole-3-carboxylate, 3.71 g (18.40 mmol) of 4-nitrophenyl chloroformate, 2.07 g (26.29 mmol) of pyridine and 0.214 g (1.75 mmol) of N,N-dimethylaminopyridine, 3.80 g of expected product are obtained in the form of a white powder.

m.p. (° C.): 85-87° C., LC-MS: M+H=337
¹H NMR (DMSO) δ (ppm): 8.40 (d, 2H); 7.60 (d, 2H); 7.10 (s, 1H); 5.55 (s, 2H); 4.40 (q, 2H); 1.40 (t, 3H).

14.2. tert-Butyl 4-[(3-ethoxycarbonylisoxazol-5-ylmethoxy-carbonylamino)methyl]-4-fluoropiperidine-1-carboxylate The process is performed according to the procedure described in Example 1 (step 1.6.). Starting with 0.70 g (3.01 mmol) of tert-butyl 4-aminomethyl-4-fluoropiperidine-1-carboxylate (commercial) and 1.11 g (3.31 mmol) of ethyl 5-(4-nitrophenoxycarbonyloxymethyl)isoxazole-3-carboxylate, obtained in step 14.1., 0.33 g of pure product is obtained in the form of an orange-coloured oil.

¹H NMR (DMSO) δ (ppm): 7.75 (broad t, 1H); 6.90 (s, 1H); 5.25 (s, 2H); 4.40 (q, 2H); 3.80 (m, 2H); 3.00 (m, 2H); 3.25 (m, 2H); 1.75-1.45 (m, 4H); 1.40 (s, 9H); 1.30 (t, 3H).

14.3. Ethyl 5-(4-fluoropiperidin-4-ylmethylcarbamoyloxymethyl)isoxazole-3-carboxylate trifluoroacetate To a solution of 0.90 g (2.10 mmol) of tert-butyl 4-[(3-ethoxycarbonylisoxazol-5-ylmethoxycarbonylamino)methyl]-4-fluoropiperidine-1-carboxylate, obtained in step 14.2., in 10 mL of dichloromethane, cooled in an ice/water bath, are added slowly 1.06 mL (12.57 mmol) of a trifluoroacetic acid solution. Stirring is continued at room temperature for 3 hours.

After evaporating under reduced pressure, 0.46 g of product is obtained in trifluoroacetate form, which is used without further purification in step 14,4. below.

14.4. Ethyl 5-[1-(6-chloroquinolin-2-yl)-4-fluoropiperidin-4-ylmethylcarbamoyloxymethyl]isoxazole-3-carboxylate 0.465 g (1.05 mmol) of ethyl 5-(4-fluoropiperidin-4-ylmethylcarbamoyloxymethyl)isoxazole-3-carboxylate trifluoroacetate, obtained in step 14.3., 0.23 g (1.15 mmol) of 2,6-dichloroquinoline and 730 μL (4.20 mmol) of N,N-diisopropylethylamine in 5 mL of acetonitrile are introduced into a sealed tube. The mixture is then heated at 120° C. for 12 hours. The mixture is allowed to cool to room temperature and the reaction medium is then taken up in ethyl acetate, the aqueous phase is separated out and extracted twice with ethyl acetate, and the combined organic phases are washed with saturated aqueous ammonium chloride solution and dried over sodium sulfate. After evaporating off the solvent, the residue obtained is purified by chromatography on a column of silica gel, eluting with a 99/1 mixture of dichloromethane and methanol, and 0.07 g of pure product is thus obtained in the form of a white powder.

m.p. (° C.): 132-134° C., LC-MS: M+H=491,
¹H NMR (DMSO) δ (ppm): 8.05 (d, 1H); 7.90-7.70 (m, 2H); 7.60-7.50 (m, 2H); 7.35 (d, 1H); 6.90 (s, 1H); 5.25 (m, 2H); 4.45-4.30 (m, 4H); 3.40-3.20 (m, 4H); 1.90-1.60 (m, 4H); 1.35 (t, 3H).

EXAMPLE 15 (COMPOUND 57)

3-Methylcarbamoylisoxazol-5-ylmethyl [4-fluoro-1-(4-trifluoromethylpyrimidin-2-yl)piperidin-4-yl]methylcarbamate

15.1. Ethyl 5-[4-fluoro-1-(4-trifluoromethylpyrimidin-2-yl)-piperidin-4-ylmethylcarbamoyloxymethyl]isoxazole-3-carboxylate The process is performed according to the procedure described in Example 14 (step 14.4.). Starting with 0.46 g (1.05 mmol) of ethyl 5-(4-fluoropiperidin-4-ylmethylcarbamoyloxymethyl)-isoxazole-3-carboxylate trifluoroacetate, obtained in step 14.3., 0.21 g (1,15 mmol) of 2-chloro-4-trifluoromethyl-pyrimidine and 730 μL (4.20 mmol) of N,N-diisopropylethylamine in 5 mL of acetonitrile, 0.22 g of pure product is thus obtained in the form of a white powder.

m.p. (° C.): 136-138° C., LC-MS: M+H=476
¹H NMR (DMSO) δ (ppm): 8.70 (d, 1H); 7.75 (t, 1H); 7.00 (d, 1H); 6.90 (s, 1H); 5.25 (s, 2H); 4.50-4.30 (m, 4H); 3.40-3.15 (m, 4H); 1.90-1.50 (m, 4H); 1.30 (t, 3H).

15.2. 3-Methylcarbamoylisoxazol-5-ylmethyl [4-fluoro-1-(4-trifluoromethylpyrimidin-2-yl)piperidin-4-yl]methylcarbamate A solution of 0.14 g (0.29 mmol) of ethyl 5-[4-fluoro-1-(4-trifluoromethylpyrimidin-2-yl)piperidin-4-ylmethylcarbamoyl-oxymethyl]isoxazole-3-carboxylate, prepared in step 15.1., in 1.10 mL (8.83 mmol) of a solution of methylamine in ethanol, is stirred at room temperature for 1 hour 30 minutes in a sealed tube. The resulting mixture is evaporated to dryness. The residue obtained is triturated in ether and filtered. After drying under vacuum at about 60° C., 0.12 g of pure product is obtained in the form of a white powder.

m.p. (° C.): 187-189° C., LC-MS: M+H=461

$^1$H NMR (DMSO) δ (ppm): 8.70 (m, 2H); 7.75 (m, 1H); 7.00 (m, 1H); 6.80 (s, 1H); 5.20 (m, 2H); 4.45 (m, 2H); 3.40-3.20 (m, 4H); 2.80 (m, 3H); 1.90-1.55 (m, 4H).

EXAMPLE 16 (COMPOUND 43)

3-Carbamoylisoxazol-5-ylmethyl [2-(5'-isobutyl-3,4,5,6-tetrahydro-2H-[1,2']bipyridinyl-4-yl]ethylcarbamate

16.1. Ethyl [2-(5'-bromo-3,4,5,6-tetrahydro-2H-[1,2'] bipyridinyl-4-yl)ethyl]carbamate The process is performed according to the method described in Example 1 (step 1.5.). Starting with 4.52 g (15.90 mmol) of 2-(5'-bromo-3,4,5,6-tetrahydro-2H-[1,2']bipyridinyl-4-yl)-ethylamine, prepared in step 10.2., 1.89 g (17.49 mmol) of ethyl chloroformate, 5.13 g (39.76 mmol) of N,N-diisopropylethylamine and 0.19 g (1.59 mmol) of N,N-dimethylaminopyridine, and after purifying on a column of silica gel, eluting with a 99/1/0.1 mixture of dichloromethane, methanol and 28% aqueous ammonia, 3.87 g of expected product are obtained in the form of a powder.

m.p. (° C.): 87-89° C.

$^1$H NMR (DMSO) δ (ppm): 8.00 (m, 1H); 7.30 (m, 1H); 6.40 (d, 1H); 4.45 (broad s, 1H); 4.15-3.90 (m, 4H); 3.10 (m, 2H); 2.60 (m, 2H); 1.65 (m, 2H); 1.55-1.25 (m, 3H); 1.20-0.95 (m, 5H).

16.2. Ethyl {2-[5'-(2-methylpropenyl)-3,4,5,6-tetrahydro-2H-[1,2']bipyridinyl-4-yl]ethyl}carbamate The process is performed according to the method described in Example 10 (step 10.5.). Starting with 1.00 g (2.81 mmol) of ethyl [2-(5'-bromo-3,4,5,6-tetrahydro-2H-[1,2']bipyridinyl-4-yl)ethyl]carbamate, prepared in the preceding step, 0.61 g (3.37 mmol) of pinacol 2-methyl-1-propenylboronate (commercial), 2.74 g (8.42 mmol) of caesium carbonate, suspended in 18 mL of a 9/1 mixture of tetrahydrofuran and water, and 0.23 g (0.28 mmol) of PdCl$_2$dppf.CH$_2$Cl$_2$, and after purifying on a column of silica gel, eluting with a 99/1/0.1 mixture of dichloromethane, methanol and 28% aqueous ammonia, 0.75 g of expected product is obtained in the form of a wax.

$^1$H NMR (CDCl$_3$) δ (ppm): 8.10 (m, 1H); 7.40 (m, 1H); 6.65 (d, 1H); 6.10 (m, 1H); 4.65 (broad s, 1H); 4.40-4.10 (m, 4H); 3.25 (m, 2H); 2.85 (m, 2H); 1.90-1.75 (m, 8H); 1.70-1.40 (m, 4H); 1.35-1.20 (m, 4H).

16.3. Ethyl [2-(5'-isobutyl-3,4,5,6-tetrahydro-2H-[1,2']bipyridinyl-4-yl)ethyl]carbamate To a solution of 0.74 g (2.23 mmol) of ethyl {2-[5'-(2-methylpropenyl)-3,4,5,6-tetrahydro-2H-[1,2']bipyridinyl-4-yl]ethyl}-carbamate obtained in the preceding step, in 30 mL of methanol is added 0.10 g (0.94 mmol) of palladium-on-charcoal. The reaction medium is placed in a Parr bomb under a hydrogen atmosphere (10 psi) at room temperature for 1 hour 30 minutes. The resulting mixture is filtered through a Büchner funnel and the filtrate is then concentrated under reduced pressure. 0.74 g of expected product is thus obtained in the form of a powder.

m.p. (° C.): 78-80° C.

$^1$H NMR (CDCl$_3$) δ (ppm): 8.00 (m, 1H); 7.30 (m, 1H); 6.65 (d, 1H); 4.65 (broad s, 1H); 4.35-4.05 (m, 4H); 3.30 (m, 2H); 2.80 (m, 2H); 2.35 (d, 2H); 1.90-1.75 (m, 2H); 1.70-1.45 (m, 2H); 1.35-1.20 (m, 3H); 0.90 (d, 6H).

16.4. 2-(5'-Isobutyl-3,4,5,6-tetrahydro-2H-[1,2']bipyridinyl-4-yl)ethylamine To a solution of 0.64 g (1.93 mmol) of ethyl [2-(5'-isobutyl-3,4,5,6-tetrahydro-2H-[1,2']bipyridinyl-4-yl)ethyl]carbamate, obtained in step 16.3., in 9.70 mL of ethanol/water (1/1), at room temperature, 2.17 g (38.68 mmol) of potassium hydroxide are added. The mixture is then heated at 110° C. for 12 hours. 2.17 g (38.68 mmol) of potassium hydroxide and the mixture is left to stir for 4 hours. The mixture is allowed to cool to room temperature and concentrated under reduced pressure. The reaction medium is taken up in dichloromethane, the aqueous phase is separated out and extracted twice with dichloromethane, and the combined organic phases are washed with saturated aqueous sodium chloride solution and dried over sodium sulfate. After evaporating under reduced pressure, 0.37 g of expected product is obtained in the form of a yellow wax.

LC-MS: M+H=262

$^1$H NMR (CDCl$_3$) δ (ppm): 8.00 (m, 1H); 7.30 (m, 1H); 6.65 (d, 1H); 4.25 (m, 2H); 2.80 (m, 4E); 2.35 (d, 2H); 1.80 (m, 3H); 1.60 (m, 1H); 1.45 (m, 2H); 1.30 (m, 4H); 0.90 (d, 6H).

16.5. 3-Carbamoylisoxazol-5-ylmethyl [2-(5'-isobutyl-3,4,5,6-tetrahydro-2H-[1,2']bipyridinyl-4-yl]ethylcarbamate The process is performed according to the procedure described in Example 1 in step 1.6. Starting with 0.37 g (1.42 mmol) of 2-(5'-isobutyl-3,4,5,6-tetrahydro-2H-[1,2']bipyridinyl-4-yl)-ethylamine, obtained in step 16.4., 0.52 g (1.70 mmol) of 3-carbamoylisoxazol-5-ylmethyl 4-nitrophenylcarbonate, obtained in step 8.3., 0.62 mL g (3.54 mmol) of N,N-diisopropylethylamine and 0.087 g (0.71 mmol) of N,N-dimethylaminopyridine, in 14 mL of 1,2-dichloroethane, 0.42 g of pure product is obtained in the form of a white powder.

m.p. (° C.): 168-170° C., LC-MS: M+H=430

$^1$H NMR (DMSO) δ (ppm): 8.10 (m, 1H); 7.95-7.75 (m, 2H); 7.50-7.25 (m, 2H); 6.75 (m, 2H); 5.20 (m, 2H); 4.20 (m, 2H); 3.10 (m, 2H); 2.70 (m, 2H); 2.30 (d, 2H); 1.85-1.65 (m, 3H); 1.60-1.30 (m, 3H); 1.10 (m, 2H); 0.85 (m, 6H).

EXAMPLE 17 (COMPOUND 72)

3-Methylcarbamoylisoxazol-5-ylmethyl {2-[4-methyl-1-(4-trifluoromethylpyrimidin-2-yl)piperidin-4-yl]ethyl}carbamate

17.1. tert-Butyl 4-(2-aminoethyl)-4-methylpiperidine-1-carboxylate

The process is performed according to the procedure described in Example 12 (step 12.2.) Starting with 1.40 g (5.87 mmol) of tert-butyl 4-cyanomethyl-4-methylpiperidine-1-carboxylate (WO 2006/001 752) and 1.72 g (29.37 mmol) of Raney nickel in 20 mL of methanol under a hydrogen atmosphere (70 psi) at 45° C., 1.35 g of expected product are obtained in the form of a wax.

LC-MS: M+H=243

$^1$H NMR (CDCl$_3$) δ (ppm): 3.60-3.40 (m, 2H); 3.30-3.10 (m, 2H); 2.75 (m, 2H); 1.50 (s, 9H); 1.40-1.25 (m, 6H); 0.95 (s, 3H).

17.2. tert-Butyl 4-methyl-4-[2-(3-methylcarbamoyl-isoxazol-5-ylmethoxycarbonylamino)ethyl]piperidine-1-carboxylate The process is performed according to the procedure described in Example 12 (step 12.3.). Starting with 0.54 g (2.22 mmol) of tert-butyl 4-(2-aminoethyl)-4-methylpiperidine-1-carboxylate and 0.78 g (2.45 mmol) of 3-(methylcarbamoyl)-isoxazol-5-ylmethyl 4-nitrophenylcarbonate obtained in step 9.2., 580 µL (3.34 mmol) of N,N-diisopropylethylamine and 0.13 g (1.11 mmol) of N,N-dimethylaminopyridine in 22 mL of 1,2-dichloroethane, 0.94 g of expected product is obtained in the form of a wax.

LC-MS: M+H=425

$^1$H NMR (DMSO) δ (ppm): 8.70 (broad s, 1H); 7.40 (broad s, 1H); 6.75 (s, 1H); 5.20 (s, 2H); 3.40 (m, 2H); 3.20 (m, 2H); 3.05 (m, 2H); 2.80 (d, 3H); 1.40 (m, 1H); 1.25 (m, 4H); 0.95 (s, 3H).

17.3. 3-Methylcarbamoylisoxazol-5-ylmethyl [2-(4-methylpiperidin-4-yl)ethyl]carbamate hydrochloride The process is performed according to the procedure described in Example 11 (step 11.2.). Starting with 0.97 g (2.30 mmol) of tert-butyl 4-methyl-4-[2-(3-methylcarbamoylisoxazol-5-ylmethoxycarbonylamino)ethyl]piperidine-1-carboxylate, obtained in step 17.2., and 5.74 mL (22.97 mmol) of a 4N solution of hydrogen chloride in dioxane, and after triturating with ether, 0.73 g of expected product is obtained in the form of a white powder.

m.p. (° C.): 188-190, LC-MS: M+H=361

$^1$H NMR (DMSO) δ (ppm): 8.70 (broad s, 1H); 8.50 (broad s, 1H); 7.45 (broad s, 1H); 6.80 (s, 1H); 5.20 (s, 2H); 3.00 (m, 6H); 2.75 (d, 3H); 1.60-1.40 (m, 6H); 0.95 (m, 3H).

17.4. 3-Methylcarbamoylisoxazol-5-ylmethyl {2-[4-Methyl-1-(4-trifluoromethylpyrimidin-2-yl)piperidin-4-yl]ethyl}carbamate The process is performed according to the procedure described in Example 12 (step 12.5.). Starting with 0.30 g (0.83 mmol) of 3-methylcarbamoylisoxazol-5-ylmethyl [2-(4-methylpiperidin-4-yl)ethyl]carbamate hydrochloride, 0.23 g (1.25 mmol) of 2-chloro-4-trifluoromethylpyrimidine and 430 µL (2.49 mmol) of N,N-diisopropylethylamine, dissolved in 2.77 mL of acetonitrile, 0.29 g of expected product is obtained in the form of a powder.

m.p. (° C.): 160-162° C., LC-MS: M+H=471

$^1$H NMR (DMSO) δ (ppm): 8.80-8.60 (m, 2H); 7.45 (m, 1H); 6.95 (m, 1H); 6.80 (s, 1H); 5.20 (s, 2H); 3.95 (m, 2H); 3.60 (m, 2H); 3.10 (m, 2H); 2.80 (s, 3H); 1.50 (m, 2H); 1.40 (m, 4H); 1.00 (s, 3H).

EXAMPLE 18 (COMPOUND 64)

3-Methylcarbamoylisoxazol-5-ylmethyl {2-[1-(6-chloroquinoxalin-2-yl)-4-ethylpiperidin-4-yl]ethyl}carbamate

18.1. tert-Butyl 4-(cyanoethoxycarbonylmethyl)-4-ethyl-piperidine-1-carboxylate To a solution of 2.00 g (6.79 mmol) of tert-butyl 4-(cyanoethoxycarbonylmethylene)piperidine-1-carboxylate (WO 2006/001752) in 33 mL of tetrahydrofuran are added dropwise, at −5° C. under argon, 4.53 mL (13.59 mmol) of a 3M solution of ethylmagnesium bromide in ether. The reaction medium is then stirred at room temperature for 12 hours. Ethyl acetate is added and the medium is cooled in a bath of ice/water, followed by addition of saturated ammonium chloride solution. The aqueous phase is separated out and extracted three times with ethyl acetate, the combined organic phases are washed with saturated aqueous sodium chloride solution and dried over sodium sulfate, and the filtrate is concentrated under reduced pressure. The residue is chromatographed on silica gel, eluting with a 95/5 mixture of cyclohexane and ethyl acetate to give 1.63 g of pure product in the form of a white powder.

LC-MS: M+H=325

$^1$H NMR (CDCl$_3$) δ (ppm): 4.25 (s, 1H); 4.20 (q, 2H); 3.50-3.15 (t, 4H); 1.60 (q, 2H); 2.50-1.55 (t, 2H); 1.40 (s, 9H); 1.20 (t, 3H); 0.85 (t, 3H).

18.2. tert-Butyl 4-cyanomethyl-4-ethylpiperidine-1-carboxylate

To a solution of 1.30 g (4.01 mmol) of tert-butyl 4-(cyanoethoxycarbonylmethyl)-4-ethylpiperidine-1-carboxylate, obtained in the preceding step, in 14 mL of dimethyl sulfoxide are added 0.09 g (1.60 mmol) of sodium chloride and 0.14 g (8.01 mmol) of water. The reaction medium is stirred at 150° C. for 1 hour. Diethyl ether and water are added. The aqueous phase is separated out and extracted three times with diethyl ether, the combined organic phases are washed with saturated aqueous sodium chloride solution and dried over sodium sulfate, and the filtrate is concentrated under reduced pressure. The residue is chromatographed on silica gel, eluting with a 95/5 mixture of cyclohexane and ethyl acetate to give 0.96 g of pure product in the form of a wax.

LC-MS: M+H=253

$^1$H NMR (CDCl$_3$) δ (ppm): 3.30 (t, 4H); 2.60 (s, 2H); 1.45 (q, 2H); 1.40 (t, 4H); 1.35 (s, 9H); 0.80 (t, 3H).

18.3. tert-Butyl 4-(2-aminoethyl)-4-ethylpiperidine-1-carboxylate

The process is performed according to the procedure described in Example 12 (step 12.2.). Starting with 0.96 g (3.83 mmol) of tert-butyl 4-cyanomethyl-4-ethylpiperidine-1-carboxylate and 1.12 g (19.15 mmol) of Raney nickel in 50 mL of methanol under a hydrogen atmosphere (70 psi) at 50° C., and after chromatography on a column of silica gel, eluting with a 95/5/0.5 mixture of dichloromethane, methanol and 28% aqueous ammonia, 0.71 g of expected product is obtained in the form of a wax.

LC-MS: M+H=257

$^1$H NMR (CDCl$_3$) δ (ppm): 3.30 (m, 4H); 2.50 (m, 2H); 1.35 (t, 2H); 1.40 (s, 9H); 1.30 (q, 2H); 1.25 (m, 4H); 0.80 (t, 3H).

18.4. tert-Butyl 4-ethyl-4-[2-(3-methylcarbamoyl-isoxazol-5-ylmethoxycarbonylamino)ethyl]piperidine-1-carboxylate The process is performed according to the procedure described in Example 12 (step 12.3.). Starting with 0.71 g (2.78 mmol) of tert-butyl 4-(2-aminoethyl)-4-ethylpiperidine-1-carboxylate, 0.98 g (3.06 mmol) of 3-(methylcarbamoyl)-isoxazol-5-ylmethyl 4-nitrophenylcarbonate obtained in step 9.1., 730 µL (4.17 mmol) of N,N-diisopropylethylamine and 0.17 g (1.39 mmol) of N,N-dimethylaminopyridine in 27 mL of 1,2-dichloroethane, 0.94 g of expected product is obtained in the form of a powder.

LC-MS: M+H=439

¹H NMR (CDCl₃) δ (ppm): 8.70 (d, 1H); 7.40 (t, 1H); 6.75 (s, 1H); 5.20 (s, 2H); 3.30 (q, 2H); 3.25 (m, 4H); 2.80 (d, 3H); 1.50-1.20 (m, 8H); 1.10(s, 9H); 0.80 (t, 3H).

18.5. 3-Methylcarbamoylisoxazol-5-ylmethyl [2-(4-ethylpiperidin-4-yl)ethyl]carbamate hydrochloride The process is performed according to the procedure described in Example 11 (step 11.2.). Starting with 0.94 g (2.14 mmol) of tert-butyl 4-ethyl-4-[2-(3-methylcarbamoyl-isoxazol-5-ylmethoxycarbonylamino)ethyl]piperidine-1-carboxylate, obtained in step 18.4., 2.68 mL (10.72 mmol) of a 4N solution of hydrogen chloride in dioxane, and after triturating in ether, 0.76 g of expected product is obtained in the form of a white powder.

m.p. (° C.): 222-224, LC-MS: M+H=339

¹H NMR (DMSO) δ (ppm): 8.70 (broad s, 2H); 7.40 (t, 1H); 6.80 (s, 1H); 5.20 (s, 2H); 2.95 (m, 6H); 2.75 (d, 3H); 1.55 (q, 2H); 1.45 (t, 2H); 1.35 (m, 4H); 0.80 (t, 3H).

18.6. 3-Methylcarbamoylisoxazol-5-ylmethyl {2-[1-(6-chloroquinoxalin-2-yl)-4-ethylpiperidin-4-yl]ethyl}carbamate The process is performed according to the procedure described in Example 12 (step 12.5.). Starting with 0.30 g (0.89 mmol) of 3-methylcarbamoylisoxazol-5-ylmethyl [2-(4-ethylpiperidin-4-yl)ethyl]carbamate hydrochloride, 0.26 g (1.33 mmol) of 2,6-dichloroquinoxaline and 460 μL (2.66 mmol) of N,N-diisopropylethylamine dissolved in 3 mL of acetonitrile, 0.29 g of expected product is obtained in the form of a yellow powder.

m.p. (° C.): 158-160° C., LC-MS: M+H=501

¹H NMR (DMSO) δ (ppm): 8.80 (s, 1H); 8.70 (m, 1H); 7.90 (s, 1H); 7.60 (s, 2H); 7.40 (m, 1H); 6.80 (s, 1H); 5.20 (s, 2H); 3.90-3.60 (m, 4H); 3.00 (m, 2H); 2.80 (m, 3H); 1.50-1.30 (m, 8H); 0.80 (t, 3H).

EXAMPLE 19 (COMPOUND 65)

3-Methylcarbamoylisoxazol-5-ylmethyl {2-[1-(6-chloroquinoxalin-2-yl)-4-isobutylpiperidin-4-yl]ethyl}carbamate

19.1. tert-Butyl 4-(cyanoethoxycarbonylmethyl)-4-isobutylpiperidine-1-carboxylate The process is performed according to the procedure described in Example 18 (step 18.1.). Starting with 5.00 g (16.99 mmol) of tert-butyl 4-(cyanoethoxycarbonylmethylene)piperidine-1-carboxylate (WO 2006/001 752) in 56 mL of tetrahydrofuran, and 16.99 mL (33.97 mmol) of a 2M solution of isobutylmagnesium bromide in ether, 1.46 g of pure product are obtained in the form of a wax.

LC-MS: M+H=353

¹H NMR (CDCl₃) δ (ppm): 4.25 (q, 2H); 3.80 (s, 1H); 3.45 (m, 2H); 3,30 (m, 2H); 1.75 (m, 5H); 1.60 (m, 2H); 1.40 (s, 9H); 1.30 (t, 3H); 0.90 (d, 6H).

19.2. tert-Butyl 4-cyanomethyl-4-isobutylpiperidine-1-carboxylate

The process is performed according to the procedure described in Example 18 (step 18.2.). Starting with 1.46 g (4.16 mmol) of tert-butyl 4-(cyanoethoxycarbonylmethyl)-4-isobutyl-piperidine-1-carboxylate obtained in the preceding step, in 14 ml of dimethyl sulfoxide, 0.097 g (1.66 mmol) of sodium chloride and 0.15 g (8.31 mmol) of water, 1.10 g of pure product are obtained in the form of a wax.

LC-MS: M+H=281

¹H NMR (CDCl₃) δ (ppm): 3.50-3.30 (m, 4H); 2.45 (m, 2H); 2.40 (s, 2H); 1.70 (m, 2H); 1.60 (m, 3H); 1.40 (s, 9H); 0.90 (d, 6H).

19.3. tert-Butyl 4-(2-aminoethyl)-4-isobutylpiperidine-1-carboxylate

The process is performed according to the procedure described in Example 12 (step 12.2.). Starting with 1.10 g (3.95 mmol) of tert-butyl 4-cyanomethyl-4-isobutylpiperidine-1-carboxylate and 1.16 g (19.75 mmol) of Raney nickel in 13 mL of methanol under a hydrogen atmosphere (70 psi), at 45° C. and after chromatography on a column of silica gel, eluting with a 96/4/0.4 mixture of dichloromethane, methanol and 28% aqueous ammonia, 0.50 g of expected product is obtained in the form of an oil.

LC-MS: M+H=285

¹H NMR (CDCl₃) δ (ppm): 3.50-3.30 (m, 4H); 2.45 (m, 2H); 1.70 (m, 1H); 1.60 (m, 4H); 1.40 (s, 9H); 1.35 (m, 4H); 1.25 (m, 2H); 0.90 (d, 6H).

19.4. tert-Butyl 4-isobutyl-4-[2-(3-methylcarbamoyl-isoxazol-5-ylmethoxycarbonylamino)ethyl]piperidine-1-carboxylate The process is performed according to the procedure described in Example 12 (step 12.3.). Starting with 0.49 g (1.73 mmol) of tert-butyl 4-(2-aminoethyl)-4-isobutylpiperidine-1-carboxylate, 0.61 g (1.91 mmol) of 3-(methylcarbamoyl)-isoxazol-5-ylmethyl 4-nitrophenylcarbonate obtained in step 9.2., 450 μL (2.60 mmol) of N,N-diisopropylethylamine and 0.10 g (0.87 mmol) of N,N-dimethylaminopyridine in 17 mL of 1,2-dichloroethane, 0.73 g of expected product is obtained in the form of a wax.

LC-MS: M+H=467

¹H NMR (DMSO) δ (ppm): 8.70 (broad s, 1H); 7.40 (m, 1H); 6.80 (s, 1H); 5.20 (s, 2H); 3.40-3.15 (m, 4H); 3.00 (m, 2H); 2.80 (d, 3H); 1.70 (m, 1H); 1.50 (m, 2H); 1.40 (s, 9H); 1.30 (m, 4H); 1.20 (m, 2H); 0.90 (d, 6H).

19.5. 3-Methylcarbamoylisoxazol-5-ylmethyl [2-(4-isobutyl-piperidin-4-yl)ethyl]carbamate The process is performed according to the procedure described in Example 11 (step 11.2.). Starting with 0.71 g (1.53 mmol) of tert-butyl 4-ethyl-4-[2- (3-methylcarbamoyl-isoxazol-5-yl-methoxycarbonylamino)isobutyl]piperidine-1-carboxylate, obtained in step 19.4., and 3.83 mL (15.30 mmol) of a 4N solution of hydrogen chloride in dioxane, and after triturating with ether, 0.60 g of the expected product is obtained in the form of an oil.

LC-MS: M+H=367

¹H NMR (DMSO) δ (ppm): 8,70 (broad s, 1H); 8.50 (broad s, 1H); 7.40 (m, 1H); 6.80 (s, 1H); 5.20 (s, 25); 3.00 (m, 6H); 2.75 (d, 3H); 1.70 (m, 1H); 1.50 (m, 6H); 1.30 (m, 2H); 0.90 (d, 65).

19.6. 3-Methylcarbamoylisoxazol-5-ylmethyl {2-[1-(6-chloroquinoxalin-2-yl)-4-isobutylpiperidin-4-yl]ethyl}carbamate The process is performed according to the procedure described in Example 12 (step 12.5.). Starting with 0.30 g (0.74 mmol) of 3-methylcarbamoylisoxazol-5-ylmethyl [2-(4-ethylpiperidin-4-yl)isobutyl]carbamate hydrochloride obtained in the preceding step, 0.22 g (1.12 mmol) of 2,6-dichloroquinoxaline and 390 µL (2.23 mmol) of N,N-diisopropylethylamine dissolved in 2.50 mL of acetonitrile, 0.29 g of expected product is obtained in the form of a yellow powder.

m.p. (° C.): 144-146° C., LC-MS: M+H=530

$^1$H NMR (DMSO) δ (ppm): 8.80 (s, 1H); 8.70 (m, 1H); 7.90 (s, 1H); 7.60 (s, 2H); 7.40 (m, 1H); 6.80 (s, 1H); 5.20 (s, 2H); 3.90 (m, 2H); 3.70 (m, 2H); 3.10 (m, 2H); 2.80 (m, 3H); 1.80 (m, 1H); 1.60-1.40 (m, 6H); 1.30 (m, 2H); 0.90 (d, 6H).

EXAMPLE 20 (COMPOUND 62)

3-Methylcarbamoylisoxazol-5-ylmethyl {2-[N-hydroxy-1-(4-trifluoromethylpyrimidin-2-yl)piperidin-4-yl]ethyl}carbamate 20.1. Benzyl 4-ethoxycarbonylmethyl-4-hydroxypiperidine-1-carboxylate To a solution of 5.00 g (56.75 mmol) of ethyl acetate in 140 mL of diethyl ether are added slowly, at –78° C. under argon, 28.38 mL (56.75 mmol) of a solution of lithium diisopropylamide (2N). After stirring for 30 minutes, 12.57 g (53.91 mmol) of benzyl 4-oxopiperidine-1-carboxylate dissolved in 140 mL of diethyl ether are added dropwise, at –78° C. under argon. The reaction medium is then stirred at room temperature for 2 hours. Ethyl acetate is added and the medium is cooled in a bath of ice/water, followed by addition of saturated ammonium chloride solution. The aqueous phase is separated out and extracted three times with ethyl acetate, the combined organic phases are washed with saturated aqueous sodium chloride solution and dried over sodium sulfate, and the filtrate is concentrated under reduced pressure. The residue is chromatographed on silica gel, eluting with an 85/15 mixture of cyclohexane and ethyl acetate to give 13.00 g of pure product in the form of an oil.

LC-MS: M+H=322

$^1$H NMR (DMSO) δ (ppm): 7.50-7.30 (m, 5H); 5.10 (s, 2H); 4.70 (s, 1H); 4.10 (q, 2H); 3.70 (m, 2H); 3.20 (broad s, 2H); 2.40 (s, 2H); 1.60 (m, 4H); 1.20 (t, 3H).

20.2. Ethyl (4-Hydroxypiperidin-4-yl)acetate hydrobromide

To a solution of 2.00g (6.22 mmol) of benzyl 4-ethoxycarbonylmethyl-4-hydroxypiperidine-1-carboxylate, obtained in the preceding step, in 31 mL of dichloromethane, cooled in an ice/water bath, are added slowly 5.46 mL (31.12 mmol) of a 5.7N solution of hydrogen bromide in acetic acid. Stirring is continued at room temperature for 2 hours. 50 mL of toluene are added and the resulting mixture is evaporated to dryness. The residue is triturated in ether. After filtering through a sinter funnel, 1.50 g of the expected product are obtained in the form of the hydrobromide.

$^1$H NMR (DMSO) δ (ppm): 8.45 (broad s, 2H); 4.10 (q, 2H); 3.40 (broad s, 1H); 3.10 (m, 4H); 2.40 (m, 2H); 1.80 (m, 4H); 1.20 (t, 3H).

20.3. Ethyl [4-hydroxy-1-(4-trifluoromethylpyrimidin-2-yl)-piperidin-4-yl]acetate The process is performed according to the procedure described in Example 12 (step 12.5.). Starting with 1.21 g (4.51 mmol) of ethyl (4-hydroxypiperidin-4-yl)acetate hydrobromide, obtained in the preceding step, 0.90 g (4.96 mmol) of 2-chloro-4-trifluoromethylpyrimidine and 1.65 mL (9.48 mmol) of N,N-diisopropylethylamine dissolved in 10 mL of acetonitrile, and after purification by chromatography on silica gel, eluting with a 99/1/0.1 mixture of dichloromethane, methanol and 28% aqueous ammonia, 1.33 g of expected product are obtained in the form of a wax.

$^1$H NMR (CDCl$_3$) δ (ppm): 8.40 (d, 1H); 6.60 (d, 2H); 4.45 (m, 2H); 4.10 (q, 2H); 3.65 (broad s, 1H); 3.40-3.20 (m, 2H); 2.40 (s, 2H); 1.75 (m, 2H); 1.60-1.30 (m, 2H); 1.20 (t, 3H).

20.4. 4-(2-Hydroxyethyl)-1-(4-trifluoromethylpyrimidin-2-yl)-piperidin-4-ol

To a solution of 1.30 g of ethyl [4-hydroxy-1-(4-trifluoromethylpyrimidin-2-yl)piperidin-4-yl]acetate, obtained in the preceding step, in 39 mL of tetrahydrofuran is added portionwise, at –10° C., 0.15 g of lithium aluminium hydride. The mixture is then stirred at room temperature for 1 hour. The reaction medium is cooled to about 0° C. and 15 mL of aqueous sodium hydroxide solution (1M) are then added slowly. The resulting mixture is stirred at room temperature for 30 minutes, followed by portionwise addition of wet sodium sulfate. The salts are separated out by filtration on Celite and the phases are then separated by settling. The aqueous phase is extracted with ethyl acetate, the combined organic phases are dried over sodium sulfate and the filtrate is concentrated under reduced pressure. The residue thus obtained is purified by chromatography on silica gel, eluting with a 97/3/0.3 mixture of dichloromethane, methanol and 28% aqueous ammonia. 0.64 g of expected product is obtained in the form of a wax.

$^1$H NMR (CDCl$_3$) δ (ppm): 8.40 (d, 1H); 6.60 (d, 1H); 4.45 (m, 2H); 4.00 (q, 2H); 3.60-3.30 (m, 2H); 3.20 (broad s, 1H); 2.50 (broad s, 1H); 1.80 (m, 4H); 1.65-1.40 (m, 2H).

20.5. 4,5,6,7-Tetrachloro-2-{2-[4-hydroxy-1-(4-trifluoromethylpyrimidin-2-yl)piperidin-4-yl]ethyl}isoindole-1,3-dione The process is performed according to the procedure described in Example 1 (step 1.3.). Starting with 0.63 g (2.16 mmol) of 4-(2-hydroxyethyl)-1-(4-trifluoromethylpyrimidin-2-yl)-piperidin-4-ol, obtained in the preceding step, 0.62 g (2.38 mmol) of triphenylphosphine, 0.69 g (2.38 mmol) of 4,5,6,7-tetrachlorosoindole-1,3-dione and a solution of 0.41 g (2.38 mmol) of diethyl azodicarboxylate (DEAD) in 10 mL of tetrahydrofuran, 0.38 g of the expected product is obtained.

$^1$H NMR (CDCl$_3$) δ (ppm): 8.40 (d, 1H); 6.70 (d, 1H); 4.50 (m, 2H); 3.90 (m, 2H); 3.60-3.30 (m, 2H); 1.90 (m, 2H); 1.70-1.40 (m, 4H).

20.6. 4-(2-Aminoethyl)-1-(4-trifluoromethylpyrimidin-2-yl)-piperidin-4-ol

The process is performed according to the procedure described in Example 1 (step 1.4.). Starting with 0.38 g (0.68 mmol) of 4,5,6,7-tetrachloro-2-{2-[4-hydroxy-1-(4-trifluoromethylpyrimidin-2-yl)piperidin-4-yl]ethyl}isoindole-1,3-dione), obtained in the preceding step, dissolved in an acetonitrile/tetrahydrofuran/water mixture (2/1/1) and 0.18 g (3.06 mmol) of ethylenediamine in 4.50 mL of ethanol, and after chromatography on silica gel, eluting with a 90/10/1 mixture of dichloromethane, methanol and 28% aqueous ammonia, 0.15 g of expected product is obtained in the form of a wax.

¹H NMR (CDCl₃) δ (ppm): 8.40 (d, 1H); 6.60 (d, 1H); 4.50 (m, 2H); 3.50-3.20 (m, 2H); 3.20 (m, 2H); 2.90-2.60 (broad s, 2H); 1.70 (m, 2H); 1.50-1.30 (m, 4H).

20.7. 3-Methylcarbamoylisoxazol-5-ylmethyl {2-[4-hydroxy-1-(4-trifluoromethylpyrimidin-2-yl)piperidin-4-yl]ethyl}carbamate The process is performed according to the procedure described in Example 12 (step 12.3.). Starting with 0.13 g (0.45 mmol) of 4-(2-aminoethyl)-1-(4-trifluoromethylpyrimidin-2-yl)-piperidin-4-ol, obtained in the preceding step, 0.187 g (0.58 mmol) of 3-(methylcarbamoyl)isoxazol-5-ylmethyl 4-nitrophenylcarbonate obtained in step 9.1., 200 μL (1.12 mmol) of N,N-diisopropylethylamine and 0.027 g (0.22 mmol) of N,N-dimethylaminopyridine in 2.20 mL of 1,2-dichloroethane, 0.165 g of expected product is obtained in the form of a powder.

m.p. (° C.): 138-140° C., LC-MS: M+H=473

¹H NMR (DMSO) δ (ppm): 8.70 (m, 2H); 7.35 (t, 1H); 6.95 (m, 1H); 6.80 (s, 1H); 5.20 (m, 2H); 4.50 (s, 1H); 4.30 (m, 2H); 3.40 (m, 2H); 3.20 (m, 2H); 2.80 (m, 3H); 1.90 (m, 4H); 1.45 (m, 2H).

EXAMPLE 21 (COMPOUND 29)

3-Methylcarbamoylisoxazol-5-ylmethyl {2-[1-(4'-fluorobiphenyl-4-yl)piperidin-4-yl]ethyl}carbamate

21.1. tert-Butyl {2-[1-(4-bromo-phenyl)piperidin-4-yl]ethyl}-carbamate 6.19 g (21.90 mmol) of 1-bromo-4-iodobenzene, 5.00 g (21.90 mmol) of tert-butyl (2-piperidin-4-ylethyl)carbamate, 9.98 g (60.66 mmol) of caesium carbonate and 0.54 g (0.88 mmol) of BINAP (2,2'-bis(diphenylphosphino)-1,1'-binaphthyl) suspended in 100 mL of toluene are placed under an inert atmosphere. 0.098 g (0.44 mmol) of palladium diacetate is then added. The reaction mixture is then refluxed for 6 hours. 0.045 g (0.20 mmol) of palladium diacetate and 0.25 g (0.40 mmol) of BINAP are added and the mixture is left to stir at reflux for 12 hours. The reaction medium is allowed to cool, and ethyl acetate and water are added. The aqueous phase is separated out and extracted twice with ethyl acetate, and the combined organic phases are washed with saturated aqueous sodium chloride solution and dried over sodium sulfate. After evaporating off the solvent, the residue obtained is purified by chromatography on silica gel, eluting with a 98/2/0.2 mixture of dichloromethane, methanol and 28% aqueous ammonia to give 1.66 g of expected product in the form of a white solid.

m.p. (° C.): 120-122° C., LC-MS: M+H=384

¹H NMR (DMSO) δ (ppm): 7.30 (d, 2H); 6.90 (d, 2H); 6.70 (broad s, 1H); 3.70 (m, 2H); 2.95 (m, 2H); 2.60 (m, 2H); 1.70 (m, 2H); 1.40 (s, 9H); 1.35 (m, 3H); 1.20 (m, 2H).

21.2. tert-Butyl {2-[1-(4'-fluorobiphenyl-4-yl)piperidin-4-yl]ethyl}carbamate The process is performed according to the procedure described in Example 10 (step 10.5.). Starting with 1.50 g (3.91 mmol) of tert-butyl {2-[1-(4-bromophenyl)piperidin-4-yl]ethyl}-carbamate, obtained in the preceding step, 0.66 g (4.70 mmol) of 4-fluorophenylboronic acid, 3.82 g (11.74 mmol) of caesium carbonate in 40 mL of a 9/1 mixture of tetrahydrofuran and water, and 0.32 g (0.39 mmol) of PdCl₂dppf.CH₂Cl₂, and after purification by chromatography on silica gel, eluting with a 98/2/0.2 mixture of dichloromethane, methanol and 28% aqueous ammonia, 1.23 g of expected product are obtained in the form of a white solid.

m.p. (° C.): 173-175° C., LC-MS: M+H=399

¹H NMR (DMSO) δ (ppm): 7.60 (m, 2H); 7.50 (d, 2H); 7.20 (m, 2H); 6.95 (d, 2H); 6.75 (broad s, 1H); 3.70 (m, 2H); 2.95 (m, 2H); 2.70 (m, 2H); 1.70 (m, 2H); 1.40 (s, 9H); 1.35 (m, 3H); 1.20 (m, 2H).

21.3. 2-[1-(4'-Fluorobiphenyl-4-yl)piperidin-4-yl]ethylamine

The process is performed according to the procedure described in Example 14 (step 14.3.). Starting with 1.10 g (2.76 mmol) of tert-butyl {2-[1-(4'-fluorobiphenyl-4-yl)piperidin-4-yl]-ethyl}carbamate, obtained in the preceding step, and 2.11 mL (25.09 mmol) of trifluoroacetic acid in 20 mL of dichloromethane, and after basification by treatment with 35% sodium hydroxide, extracting with dichloromethane, drying over sodium sulfate and evaporating to dryness, 0.74 g of expected product is obtained in the form of an amorphous orange-coloured solid.

LC-MS: M+H=299

¹H NMR (DMSO) δ (ppm): 7.60 (m, 2H); 7.50 (d, 2H); 7.25 (m, 2H); 7.00 (d, 2H); 3.75 (m, 2H); 2.85 (m, 2H); 2.75 (m, 2H); 1.70 (m, 2H); 1.50 (m, 1H); 1.35 (m, 2H); 1.25 (m, 2H).

21.4. 3-Methylcarbamoylisoxazol-5-ylmethyl {2-[1-(4'-fluorobiphenyl-4-yl)piperidin-4-yl]ethyl}carbamate The process is performed according to the procedure described in Example 12 (step 12.3.). Starting with 0.27 g (0.90 mmol) of 2-[1-(4'-fluorobiphenyl-4-yl)piperidin-4-yl]ethylamine, obtained in the preceding step, 0.29 g (0.90 mmol) of 3-(methylcarbamoyl)isoxazol-5-ylmethyl 4-nitrophenylcarbonate obtained in step 9.1., and 320 μL (1.81 mmol) of N,N-diisopropylethylamine in 10 mL of 1,2-dichloroethane, and after triturating in ether, 0.26 g of expected product is obtained in the form of a white powder.

m.p. (° C.): 212-215° C., LC-MS: M+H=481

¹H NMR (DMSO) δ (ppm): 8.70 (broad s, 1H); 7.60 (m, 2H); 7.50 (m, 2H); 7.45 (broad s, 1H); 7.25 (m, 2H); 7.00 (m, 2H); 6.90 (s, 1H); 5.20 (s, 2H); 3.75 (m, 2H); 3.10 (m, 2H); 2.80 (s, 3H); 2.70 (m, 2H); 1.75 (m, 2H); 1.45 (m, 3H); 1.25 (m, 2H).

EXAMPLE 22 (COMPOUND 79)

3-Methylcarbamoylisoxazol-5-ylmethyl (±)-[1-(4-chlorophthalazin-1-yl)pyrrolidin-3-ylmethyl]carbamate

22.1 tert-Butyl (±)-3-[(3-methylcarbamoylisoxazol-5-ylmethoxycarbonylamino)methyl]pyrrolidine-1-carboxylate The process is performed according to the procedure described in Example 1 (step 1.6.). Starting with 2.00 g (9.99 mmol) of (±)-1-Boc-3-(aminomethyl)pyrrolidine (commercial), 3.52 g (10.98 mmol) of 3-(methylcarbamoyl)isoxazol-5-ylmethyl 4-nitrophenylcarbonate obtained in step 9.2., 2.61 mL (14.98 mmol) of N,N-diisopropylethylamine and 0.61 g (4.99 mmol) of dimethylaminopyridine in 100 mL of 1,2-dichloroethane, and after purification by chromatography on silica gel, eluting with a 100/0/0 to 98/2/0.2 mixture of dichloromethane, methanol and 28% aqueous ammonia, 1.32 g of expected product are obtained in the form of a wax.

LC-MS: M+H=383

$^1$H NMR (DMSO) δ (ppm): 8.70 (bs, 1H); 7.00 (bs, 1H); 6.80 (s, 1H); 5.25 (s, 2H); 3.40 (m, 3H); 3.00 (m, 3H); 2.80 (s, 3H); 2.20 (m, 1H); 1.90 (m, 1H); 1.60 (m, 1H); 1.40 (s, 9H).

22.2 3-Methylcarbamoylisoxazol-5-ylmethyl (±)-pyrrolidin-3-ylmethylcarbamate hydrochloride The process is performed according to the procedure described in Example 11 (step 11.2.). Starting with 1.30 g (3.40 mmol) of tert-butyl 3-[(3-methylcarbamoylisoxazol-5-ylmethoxycarbonylamino)methyl]pyrrolidine-1-carboxylate and 4.25 mL of hydrogen chloride as a 4N solution in dioxane, and after triturating in diethyl ether, 0.82 g of a white powder is obtained.

m.p. (° C.): 187-189° C., LC-MS: M+H=283

$^1$H NMR (DMSO) δ (ppm): 8.70 (bs, 1H); 8.00 (m, 2H); 6.80 (m, 1H); 5.25 (s, 2H); 3.60 (m, 1H); 3.45 (m, 1H); 3.30 (m, 1H); 3.10 (m, 1H); 2.90 (m, 2H); 2.80 (s, 3H); 2.50 (m, 1H); 2.05 (m, 1H); 1.70 (m, 1H).

22.3 3-Methylcarbamoylisoxazol-5-ylmethyl (±)-[1-(4-chlorophthalazin-1-yl)pyrrolidin-3-ylmethyl]arbamate The process is performed according to the procedure described in Example 12 (step 12.5.). Starting with 0.19 g (0.60 mmol) of 3-methylcarbamoylisoxazol-5-ylmethyl pyrrolidin-3-ylmethylcarbamate hydrochloride, 0.17 g (0.89 mmol) of 1,4-dichlorophthalazine and 0.21 mL (0.15 mmol) of N,N-diisopropylethylamine (15 min, 150° C.), and after purification by chromatography on silica gel, eluting with a 100/0/0 to 98/2/0.2 mixture of dichloromethane, methanol and 28% aqueous ammonia, 0.09 g of expected product is obtained in the form of a white powder.

m.p. (° C.): 159-161° C., LC-MS: M+H=445

$^1$H NMR (DMSO) δ (ppm): 8.80 (m, 1H); 8.40 (m, 1H); 8.15 (m, 1H); 8.05 (m, 2H); 7.80 (m, 1H); 6.80 (s, 1H); 5.25 (s, 2H); 3.65 (m, 1H); 3.50 (m, 2H); 3.30 (m, 1H); 3.20 (m, 2H); 2.80 (m, 4H); 2.05 (m, 1H); 1.70 (m, 1H).

EXAMPLE 23 (COMPOUND 82)

3-Carbamoylisoxazol-5-ylmethyl {2-[1-(4-trifluoromethylpyrimidin-2-yl)azetidin-3-yl]ethyl}carbamate

23.1 tert-Butyl {2-[1-(4-trifluoromethylpyrimidin-2-yl)-azetidin-3-yl]ethyl}carbamate The process is performed according to the procedure described in Example 14 (step 14.4.). Starting with 3.00 g (12.57 mmol) of tert-butyl (2-azetidin-3-ylethyl)carbamate (commercial), 3.00 g (16.47 mmol) of 2-chloro-4-trifluoromethylpyrimidine and 7.73 mL (44.35 mmol), 4.00 g of product are obtained in the form of an orange-coloured powder after purification by chromatography on silica gel, eluting with a 100/0/0 to 98/2/0.2 mixture of dichloromethane, methanol and 28% aqueous ammonia.

m.p. (° C.): 95-97° C.

23.2 2-[1-(4-Trifluoromethylpyrimidin-2-yl)azetidin-3-yl]-ethylamine

The process is performed according to the procedure described in Example 11 (step 11.2.). Starting with 3.67 g (10.60 mmol) of tert-butyl {2-[1- (4-trifluoromethylpyrimidin-2-yl)azetidin-3-yl]ethyl}carbamate and 10.60 mL (42.38 mmol) of a 4N solution of hydrogen chloride in dioxane, 1.75 g of product are obtained in the form of a yellow oil, after purification by chromatography on silica gel, eluting with a 100/0/0 to 90/10/1 mixture of dichloromethane, methanol and 28% aqueous ammonia.

LC-MS: M+H=247

$^1$H NMR (CDCl$_3$) δ (ppm): 8.50 (d, 1H); 6.80 (d, 1H); 4.30 (m, 2H); 3.90 (m, 2H); 2.85 (m, 1H); 2.75 (m, 2H); 1.85 (m, 2H); 1.30 (bs, 2H).

23.3 3-Carbamoylisoxazol-5-ylmethyl {2-[1-(4-trifluoromethylpyrimidin-2-yl)azetidin-3-yl]ethyl}carbamate The process is performed according to the procedure described in Example 1 (step 1.6.). Starting with 0.30 g (1.22 mmol) of 2-[1-(4-trifluoromethylpyrimidin-2-yl)azetidin-3-yl]ethylamine, 0.45 g (1.46 mmol) of 3-carbamoylisoxazol-5-ylmethyl 4-nitrophenylcarbonate described in Example 8 (step 8.3.), 0.53 mL (3.05 mmol) of diisopropylethylamine and 0.07 g (0.61 mmol) of dimethylaminopyridine, 0.41 g of product is obtained in the form of a white powder after purification by chromatography on silica gel, eluting with a 100/0/0 to 98/2/0.2 mixture of dichloromethane, methanol and 28% aqueous ammonia.

m.p. (° C.): 163-165° C., LC-MS: M+H=415

$^1$H NMR (DMSO) δ (ppm): 8.65 (d, 1H); 8.15 (bs, 1H); 7.85 (bs, 1H); 7.50 (bt, 1H); 7.05 (d, 1H); 6.80 (s, 1H); 5.20 (s, 2H); 4.20 (s, 2H); 3.70 (m, 2H); 3.10 (m, 2H); 2.75 (m, 1H); 1.80 (m, 2H).

EXAMPLE 24 (COMPOUND 84)

3-Methylcarbamoylisoxazol-5-ylmethyl (−)-[1-(4-chloropyrimidin-2-yl)pyrrolidin-3-ylmethy]carbamate 0.32 g of 3-methylcarbamoylisoxazol-5-ylmethyl (±)-[1-(4-chloropyrimidin-2-yl)pyrrolidin-3-ylmethyl]carbamate was separated by chiral HPLC preparative chromatography (Chiralpak AD 20 μm 50×220 mm), eluting with a propanol/n-heptane mixture in 25/75 proportions to give 0.070 g of product obtained in base form.

t$_R$: 45 min.

m.p. (° C.): 114.4-118.3° C., LC-MS: M+H=429

[α]$^{2° C.}$ −9.88 (c=0.333, DMSO, 589 nm)

$^1$H NMR (DMSO) δ (ppm): 8.70 (bs, 1H); 8.60 (bs, 1H); 8.05 (m, 1H); 7.00 (m, 1H); 6.80 (s, 1H); 5.25 (s, 2H); 3.45 (m, 2H); 3.30 (m, 3H); 3.10 (m, 1H); 2.80 (m, 3H); 2.50 (m, 1H); 2.00 (m, 1H); 1.70 (m, 1H).

EXAMPLE 25 (COMPOUND 85)

3-Methylcarbamoylisoxazol-5-ylmethyl (+)-[1-(4-chloropyrimidin-2-yl)pyrrolidin-3-ylmethyl]carbamate 0.32 g of 3-methylcarbamoylisoxazol-5-ylmethyl (±)-[1-(4-chloropyrimidin-2-yl)pyrrolidin-3-ylmethyl]carbamate was separated by chiral HPLC preparative chromatography (Chiralpak AD 20 μm 50×220 mm), eluting with a propanol/ n-heptane mixture in 25/75 proportions to give 0.090 g of product obtained in base form.

$t_R$: 52 min.

m.p. (° C.): 114.4-118.3° C., LC-MS: M+H=429

$[\alpha]^{20°\,C.}$+9.55(c=0.222, DMSO, 589 nm)

¹H NMR (DMSO) δ (ppm): 8.70 (bs, 1H); 8.60 (bs, 1H); 8.05 (m, 1H); 7.00 (m, 1H); 6.80 (s, 1H); 5.25 (s, 2H); 3.45 (m, 2H); 3.30 (m, 3H); 3.10 (m, 1H); 2.80 (m, 3H); 2.50 (m, 1H); 2.00 (m, 1H); 1.70 (m, 1H).

Table 1 below illustrates the chemical structures and the physical properties of a number of compounds according to the invention.

In this table:
- all the compounds are in base form;
- the "m.p. (° C.)" column gives the melting points of the products in degrees Celsius (° C.);
- the term "Rot." indicates the laevorotatory or dextrorotatory nature of the compound;
- the dotted bond "- - -" represents the bond connecting the substituent to the rest of the molecule.

TABLE 1

| No. | $R_1$ | m | n | A | $R_2$ | $R_3$ | $R_4$ | m.p. (° C.) |
|---|---|---|---|---|---|---|---|---|
| 1. | 6-Cl-quinolin-2-yl | 2 | 2 | (CH₂)₂ | H | H | 5-carbamoyl-isoxazol-3-yl | 220-222° C. |
| 2. | 6-Cl-quinolin-2-yl | 2 | 2 | (CH₂)₂ | H | H | 1-methyl-1H-1,2,4-triazol-5-yl | 122-124° C. |
| 3. | 6-Cl-quinolin-2-yl | 2 | 2 | (CH₂)₂ | H | H | 3-(4-chlorophenyl)-isoxazol-5-yl | 139-140° C. |
| 4. | 6-Cl-quinolin-2-yl | 2 | 2 | (CH₂)₂ | H | H | 3-(4-chlorophenyl)-1,2,4-oxadiazol-5-yl | 134-136° C. |
| 5. | 5-(4-fluorophenyl)-pyridin-2-yl | 2 | 2 | (CH₂)₂ | H | H | 3-ethyl-1,2,4-oxadiazol-5-yl | 110-112° C. |

TABLE 1-continued

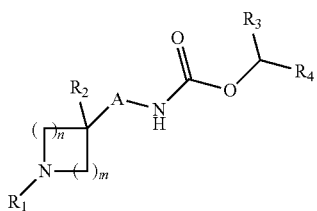

| No. | R₁ | m | n | A | R₂ | R₃ | R₄ | m.p. (°C.) |
|---|---|---|---|---|---|---|---|---|
| 6. | 6-chloroquinolin-2-yl | 2 | 2 | (CH₂)₂ | H | H | 5-methyl-3-phenylisoxazol-4-yl | 110-112° C. |
| 7. | 6-(4-fluorophenyl)pyridin-3-yl | 2 | 2 | (CH₂)₂ | H | H | 3-isopropyl-1,2,4-oxadiazol-5-yl | 96-98° C. |
| 8. | 6-(4-fluorophenyl)pyridin-3-yl | 2 | 2 | (CH₂)₂ | H | H | 1-methyl-1H-pyrazol-3-yl | 154-156° C. |
| 9. | 6-(4-fluorophenyl)pyridin-3-yl | 2 | 2 | (CH₂)₂ | H | H | 1,2,3-thiadiazol-4-yl | 139-141° C. |
| 10. | 6-(4-fluorophenyl)pyridin-3-yl | 2 | 2 | (CH₂)₂ | H | H | 5-tert-butyl-1,3,4-thiadiazol-2-yl | 139-140° C. |
| 11. | 6-(4-fluorophenyl)pyridin-3-yl | 2 | 2 | (CH₂)₂ | H | H | 3-isopropyl-1,3,4-oxadiazol-5-yl | 112-113° C. |

TABLE 1-continued
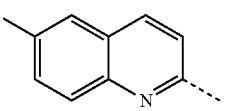
| No. | R₁ | m | n | A | R₂ | R₃ | R₄ | m.p. (° C.) |
|---|---|---|---|---|---|---|---|---|
| 12. | 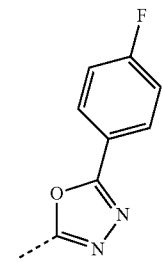 | 2 | 2 | (CH₂)₂ | H | H | 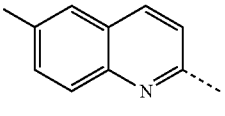 | 169-170° C. |
| 13. | 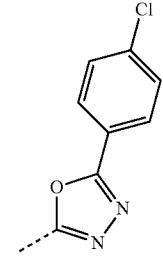 | 2 | 2 | (CH₂)₂ | H | H | 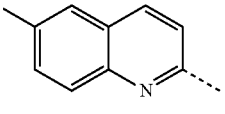 | 152-153° C. |
| 14. | 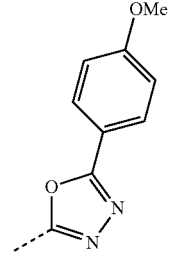 | 2 | 2 | (CH₂)₂ | H | H | 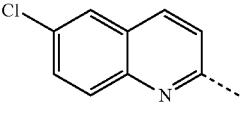 | 154-156° C. |
| 15. | 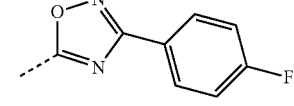 | 2 | 2 | (CH₂)₂ | H | H | 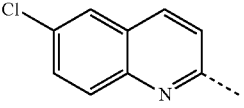 | 160-162° C. |
| 16. | 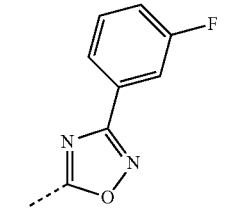 | 2 | 2 | (CH₂)₂ | H | H | (3-fluorophenyl-1,2,4-oxadiazole) | 134-136° C. |

TABLE 1-continued

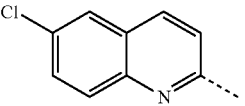

| No. | R₁ | m | n | A | R₂ | R₃ | R₄ | m.p. (° C.) |
|---|---|---|---|---|---|---|---|---|
| 17. | 6-chloroquinolin-2-yl | 2 | 2 | (CH₂)₂ | H | H | 5-(4-chlorophenyl)-1,2,4-thiadiazol-3-yl | 191-193° C. |
| 18. | 6-chloroquinolin-2-yl | 2 | 2 | (CH₂)₂ | H | H | 1,2,3-thiadiazol-4-yl | 146-148° C. |
| 19. | 5-(4-fluorophenyl)pyridin-2-yl | 2 | 2 | (CH₂)₂ | H | H | 5-(aminocarbonyl)isoxazol-3-yl | 202-204° C. |
| 20. | 6-chloroquinolin-2-yl | 2 | 2 | (CH₂)₂ | H | H | 5-(methylaminocarbonyl)isoxazol-3-yl | 200-202° C. |
| 21. | 5-(4-fluorophenyl)pyridin-2-yl | 2 | 2 | (CH₂)₂ | H | H | 4-(aminocarbonyl)-2-methyloxazol-5-yl | 206-208° C. |
| 22. | 6-(4-fluorophenyl)pyridin-2-yl | 2 | 2 | (CH₂)₂ | H | H | 5-(methylaminocarbonyl)isoxazol-3-yl | 155.5-157.5° C. |
| 23. | 6-fluoroquinolin-2-yl | 2 | 2 | (CH₂)₂ | H | H | 5-(aminocarbonyl)isoxazol-3-yl | 200-202° C. |
| 24. | 6-(4-fluorophenyl)pyridin-2-yl | 2 | 2 | (CH₂)₂ | H | H | 5-(aminocarbonyl)isoxazol-3-yl | 172-174° C. |

TABLE 1-continued

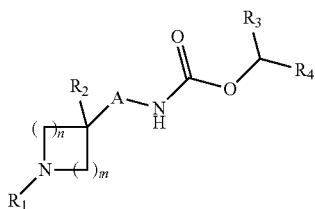

| No. | R₁ | m | n | A | R₂ | R₃ | R₄ | m.p. (°C.) |
|---|---|---|---|---|---|---|---|---|
| 25. | 6-fluoroquinolin-2-yl | 2 | 2 | (CH₂)₂ | H | H | 5-(N-methylcarbamoyl)isoxazol-3-yl | 180–182° C. |
| 26. | 5-(4-fluorophenyl)pyridin-2-yl | 2 | 2 | (CH₂)₂ | H | H | 5-(N-methylcarbamoyl)isoxazol-3-yl | 191–193° C. |
| 27. | 6-(4-fluorophenyl)pyridin-2-yl | 2 | 2 | (CH₂)₂ | H | H | 5-(N,N-dimethylcarbamoyl)isoxazol-3-yl | 81–83° C. |
| 28. | 5-(3-fluorophenyl)pyridin-2-yl | 2 | 2 | (CH₂)₂ | H | H | 5-carbamoylisoxazol-3-yl | 172–176° C. |
| 29. | 4′-fluorobiphenyl-4-yl | 2 | 2 | (CH₂)₂ | H | H | 5-(N-methylcarbamoyl)isoxazol-3-yl | 212–215° C. |
| 30. | 5-(4-fluorophenyl)pyridin-2-yl | 2 | 2 | (CH₂)₂ | H | H | 5-(N,N-dimethylcarbamoyl)isoxazol-3-yl | 149–151° C. |
| 31. | 6-chloroquinolin-2-yl | 2 | 2 | (CH₂)₂ | H | H | 5-(N,N-dimethylcarbamoyl)isoxazol-3-yl | 114–116° C. |

TABLE 1-continued

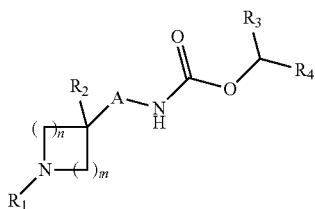

| No. | R₁ | m | n | A | R₂ | R₃ | R₄ | m.p. (°C.) |
|---|---|---|---|---|---|---|---|---|
| 32. | 6-(4-fluorophenyl)pyrazin-2-yl | 2 | 2 | (CH₂)₂ | H | H | 5-(N-methylcarbamoyl)isoxazol-3-yl | 150-152° C. |
| 33. | 6-(4-fluorophenyl)pyrazin-2-yl | 2 | 2 | (CH₂)₂ | H | H | 5-carbamoylisoxazol-3-yl | 165-167° C. |
| 34. | 6-(4-fluorophenyl)pyrazin-2-yl | 2 | 2 | (CH₂)₂ | H | H | 5-(N,N-dimethylcarbamoyl)isoxazol-3-yl | 100-102° C. |
| 35. | 5-(4-fluorophenyl)pyrimidin-2-yl | 2 | 2 | (CH₂)₂ | H | H | 5-(N-methylcarbamoyl)isoxazol-3-yl | 209-211° C. |
| 36. | 5-(4-fluorophenyl)pyrimidin-2-yl | 2 | 2 | (CH₂)₂ | H | H | 5-(N,N-dimethylcarbamoyl)isoxazol-3-yl | 147-149° C. |
| 37. | 4-(trifluoromethyl)pyrimidin-2-yl | 2 | 2 | (CH₂)₂ | H | H | 5-(N-methylcarbamoyl)isoxazol-3-yl | 164-166° C. |
| 38. | 4-(trifluoromethyl)pyrimidin-2-yl | 2 | 2 | (CH₂)₂ | H | H | 5-carbamoylisoxazol-3-yl | 165-167° C. |

TABLE 1-continued
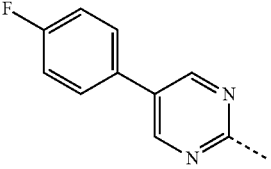
| No. | R₁ | m | n | A | R₂ | R₃ | R₄ | m.p. (° C.) |
|---|---|---|---|---|---|---|---|---|
| 39. | 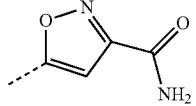 | 2 | 2 | (CH₂)₂ | H | H | 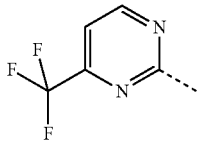 | 209-211° C. |
| 40. | 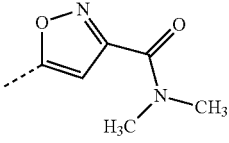 | 2 | 2 | (CH₂)₂ | H | H | 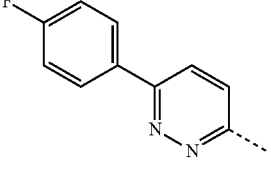 | 100-102° C. |
| 41. | 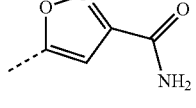 | 2 | 2 | (CH₂)₂ | H | H | 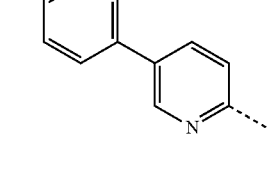 | 198-200° C. |
| 42. | 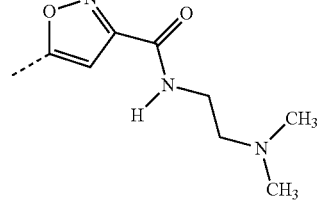 | 2 | 2 | (CH₂)₂ | H | H | 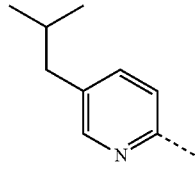 | 143-145° C. |
| 43. | 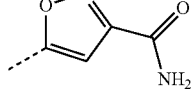 | 2 | 2 | (CH₂)₂ | H | H | 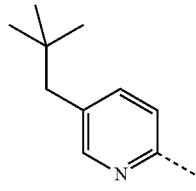 | 168-170° C. |
| 44. | 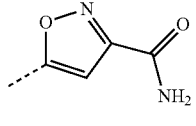 | 2 | 2 | (CH₂)₂ | H | H | 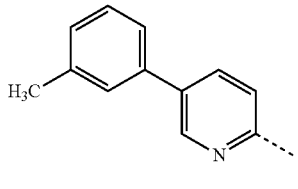 | 173-175° C. |
| 45. | 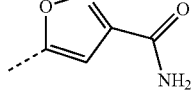 | 2 | 2 | (CH₂)₂ | H | H | | 179-181° C. |

TABLE 1-continued

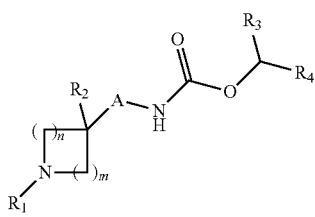

| No. | R₁ | m | n | A | R₂ | R₃ | R₄ | m.p. (° C.) |
|---|---|---|---|---|---|---|---|---|
| 46. | 4-fluorophenyl-pyridine | 2 | 2 | (CH₂)₂ | H | H | 5-isoxazolyl-C(O)-N(4-methylpiperazine) | 180-182° C. |
| 47. | 3-(trifluoromethoxy)phenyl-pyridine | 2 | 2 | (CH₂)₂ | H | H | 5-isoxazolyl-C(O)NH₂ | 177-179° C. |
| 48. | 3-chlorophenyl-pyridine | 2 | 2 | (CH₂)₂ | H | H | 5-isoxazolyl-C(O)NH₂ | 179-181° C. |
| 49. | 3-methoxy-5-fluorophenyl-pyridine | 2 | 2 | (CH₂)₂ | H | H | 5-isoxazolyl-C(O)NH₂ | 175-177° C. |
| 50. | benzo[1,3]dioxol-5-yl-pyridine | 2 | 2 | (CH₂)₂ | H | H | 5-isoxazolyl-C(O)NH₂ | 206-208° C. |
| 51. | 4-(trifluoromethyl)pyrimidine | 2 | 2 | CH₂ | F | H | 5-isoxazolyl-C(O)OCH₂CH₃ | 136-138° C. |

TABLE 1-continued

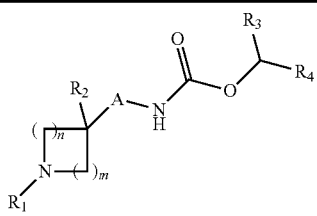

| No. | R₁ | m | n | A | R₂ | R₃ | R₄ | m.p. (°C.) |
|---|---|---|---|---|---|---|---|---|
| 52. | 4-(trifluoromethyl)pyrimidin-2-yl | 2 | 2 | (CH₂)₃ | H | H | 1-methyl-1H-pyrazol-3-yl | 72-74° C. |
| 53. | 6-chloroquinolin-2-yl | 2 | 2 | (CH₂)₂ | H | H | 5-(carboxy)isoxazol-3-yl | 180-182° C. |
| 54. | 6-chloroquinoxalin-2-yl | 2 | 2 | CH₂ | H | H | 5-isopropyl-1,3,4-oxadiazol-2-yl | 136-138° C. |
| 55. | 4-(trifluoromethyl)pyrimidin-2-yl | 2 | 2 | CH₂ | H | H | 5-isopropyl-1,3,4-oxadiazol-2-yl | 104-106° C. |
| 56. | 6-chloroquinolin-2-yl | 2 | 2 | CH₂ | F | H | 5-(ethoxycarbonyl)isoxazol-3-yl | 132-134° C. |
| 57. | 4-(trifluoromethyl)pyrimidin-2-yl | 2 | 2 | CH₂ | F | H | 5-(N-methylcarbamoyl)isoxazol-3-yl | 187-189° C. |
| 58. | 4-nitro-2-(trifluoromethyl)phenyl | 2 | 2 | CH₂ | H | H | 5-isopropyl-1,3,4-oxadiazol-2-yl | Wax |
| 59. | 4-chlorophthalazin-1-yl | 2 | 2 | CH₂ | H | H | 5-isopropyl-1,3,4-oxadiazol-2-yl | 139-141° C. |

TABLE 1-continued

[Structure: azetidine/pyrrolidine ring with N-R₁, substituent R₂, linker A-NH-C(=O)-O-CR₃R₄]

| No. | R₁ | m | n | A | R₂ | R₃ | R₄ | m.p. (°C) |
|---|---|---|---|---|---|---|---|---|
| 60. | 4-(trifluoromethyl)pyrimidin-2-yl | 1 | 1 | (CH₂)₂ | N(CH₃)₂ | H | 5-(N-methylcarbamoyl)isoxazol-3-yl | 154-156° C. |
| 61. | 4-(trifluoromethyl)pyrimidin-2-yl | 2 | 2 | (CH₂)₂ | CH₂CH₃ | H | 5-(N-methylcarbamoyl)isoxazol-3-yl | 152-154° C. |
| 62. | 4-(trifluoromethyl)pyrimidin-2-yl | 2 | 2 | (CH₂)₂ | OH | H | 5-(N-methylcarbamoyl)isoxazol-3-yl | 138-140° C. |
| 63. | 4-chlorophthalazin-1-yl | 1 | 1 | (CH₂)₂ | N(CH₃)₂ | CF₃ | 1-methyl-1H-imidazol-2-yl | 168-170° C. Rot. (±) |
| 64. | 7-chloroquinoxalin-2-yl | 2 | 2 | (CH₂)₂ | CH₂CH₃ | H | 5-(N-methylcarbamoyl)isoxazol-3-yl | 158-160° C. |
| 65. | 7-chloroquinoxalin-2-yl | 2 | 2 | (CH₂)₂ | CH₂CH(CH₃)₂ | H | 5-(N-methylcarbamoyl)isoxazol-3-yl | 144-146° C. |
| 66. | 4-nitro-2-(trifluoromethyl)phenyl | 2 | 2 | (CH₂)₂ | CH₂CH(CH₃)₂ | H | 5-(N-methylcarbamoyl)isoxazol-3-yl | 145-147° C. |
| 67. | isoquinolin-1-yl | 2 | 2 | CH₂ | H | H | 5-(propan-2-yl)-1,3,4-oxadiazol-2-yl | 95-97° C. |

TABLE 1-continued

| No. | R₁ | m | n | A | R₂ | R₃ | R₄ | m.p. (°C.) |
|---|---|---|---|---|---|---|---|---|
| 68. | 4-F-phenyl-pyrazinyl | 2 | 2 | (CH₂)₂ | H | H | isoxazole-3-C(O)NH₂ | 187-189° C. |
| 69. | 4-F-phenyl-pyrazinyl | 2 | 2 | (CH₂)₂ | H | H | isoxazole-3-C(O)NHCH₃ | 181.5-183.5° C. |
| 70. | 4-CF₃-pyrimidin-2-yl | 2 | 2 | bond | H | H | isoxazole-3-C(O)NHCH₃ | 197-199° C. |
| 71. | 6-Cl-quinolin-2-yl | 2 | 2 | (CH₂)₂ | H | H | isoxazole-3-C(O)OCH₂CH₃ | 117-119° C. |
| 72. | 4-CF₃-pyrimidin-2-yl | 2 | 2 | (CH₂)₂ | CH₃ | H | isoxazole-3-C(O)NHCH₃ | 160-162° C. |
| 73. | 6-Cl-quinolin-2-yl | 2 | 2 | (CH₂)₂ | H | CF₃ | 1-methyl-imidazol-2-yl | 196-198° C. Rot. (±) |
| 74. | 4-CF₃-pyrimidin-2-yl | 2 | 3 | bond | H | H | isoxazole-3-C(O)NH₂ | 171-173° C. Rot. (±) |

TABLE 1-continued

| No. | R₁ | m | n | A | R₂ | R₃ | R₄ | m.p. (° C.) |
|---|---|---|---|---|---|---|---|---|
| 75. | 1-chloro-phthalazin-4-yl | 2 | 2 | bond | H | H | 5-(N-methylcarbamoyl)isoxazol-3-yl | 208-210° C. |
| 76. | 2-nitro-6-(trifluoromethyl)phenyl | 2 | 2 | bond | H | H | 5-(N-methylcarbamoyl)isoxazol-3-yl | 156-158° C. |
| 77. | 7-chloroquinoxalin-2-yl | 2 | 2 | bond | H | H | 5-(N-methylcarbamoyl)isoxazol-3-yl | 232-234° C. |
| 78. | 7-chloroquinoxalin-2-yl | 2 | 2 | (CH₂)₂ | CH₃ | H | 5-(N-methylcarbamoyl)isoxazol-3-yl | 167-169° C. |
| 79. | 1-chloro-phthalazin-4-yl | 2 | 1 | CH₂ | H | H | 5-(N-methylcarbamoyl)isoxazol-3-yl | 159-161° C. Rot. (±) |
| 80. | 6-chloroquinolin-2-yl | 2 | 2 | (CH₂)₂ | H | isobutyl | furan-3-yl | 97-99° C. Rot. (±) |
| 81. | 6-(4-fluorophenyl)pyridin-2-yl | 2 | 2 | (CH₂)₂ | H | isobutyl | furan-3-yl | 101-103° C. Rot. (±) |
| 82. | 4-(trifluoromethyl)pyrimidin-2-yl | 1 | 1 | (CH₂)₂ | H | H | 5-carbamoylisoxazol-3-yl | 163-165° C. |

TABLE 1-continued

| No. | R₁ | m | n | A | R₂ | R₃ | R₄ | m.p. (° C.) |
|---|---|---|---|---|---|---|---|---|
| 83. | 4-(trifluoromethyl)pyrimidin-2-yl | 1 | 1 | (CH₂)₂ | H | H | 5-(N-methylcarbamoyl)isoxazol-3-yl | 155-157° C. |
| 84. | 4-(trifluoromethyl)pyrimidin-2-yl | 2 | 1 | CH₂ | H | H | 5-(N-methylcarbamoyl)isoxazol-3-yl | 114.4-118.3° C. Rot. (−) |
| 85. | 4-(trifluoromethyl)pyrimidin-2-yl | 2 | 1 | CH₂ | H | H | 5-(N-methylcarbamoyl)isoxazol-3-yl | 114.4-118.3° C. Rot. (+) |

Table 2 below gives the results of the ¹H NMR analyses and of the LC-MS analyses for the compounds of Table 1. In this table, the RT column indicates the retention time.

TABLE 2

| | | LC-MS | | |
|---|---|---|---|---|
| No. | ¹H NMR | M + H | RT | Method |
| 1 | (DMSO) δ (ppm): 8.15 (broad s, 1H); 8.0 (d, 1H); 7.85 (broad s, 1H); 7.75 (d, 1H); 7.50 (q, 2H); 7.45 (broad t, 1H); 7.30 (d, 1H); 6.80 (s, 1H); 5.20 (s, 2H); 4.50 (broad d, 2H); 3.10 (m, 2H); 2.90 (broad t, 2H); 1.80 (broad d, 2H); 1.60 (m, 1H); 1.40 (m, 2H); 1.15 (m, 2H). | 458 | 0.79 | A |
| 2 | (DMSO) δ (ppm): 8.0 (d, 1H); 7.9 (s, 1H); 7.80 (s, 1H); 7.50 (q, 2H); 7.40 (broad t, 1H); 7.30 (d, 1H); 5.15 (s, 2H); 4.55 (broad d, 2H); 4.10 (s, 3H); 3.10 (m, 2H); 2.90 (broad t, 2H); 1.80 (broad d, 2H); 1.60 (m, 1H); 1.40 (m, 2H); 1.15 (m, 2H). | 429 | 0.75 | A |
| 3 | (DMSO) δ (ppm): 8.0 (d, 1H); 7.90 (d, 2H); 7.80 (s, 1H); 7.60 (q, 2H); 7.50 (q, 2H); 7.40 (broad t, 1H); 7.25 (d, 1H); 7.10 (s, 1H); 5.2 (s, 2H); 4.50 (broad d, 2H); 3.10 (m, 2H); 2.85 (broad t, 2H); 1.80 (broad d, 2H); 1.65 (m, 1H); 1.4 (m, 2H); 1.15 (m, 2H). | 525 | 1.12 | A |
| 4 | (DMSO) δ (ppm): 8.05 (m, 3H); 7.80 (s, 1H); 7.75 (m, 3H); 7.50 (q, 2H); 7.25 (d, 1H); 5.4 (s, 2H); 4.50 (broad d, 2H); 3.15 (m, 2H); 2.85 (broad t, 2H); 1.80 (broad d, 2H); 1.65 (m, 1H); 1.4 (m, 2H); 1.15 (m, 2H). | 526 | 5.87 | B |
| 5 | (DMSO) δ (ppm): 8.40 (s, 1H); 7.8 (d, 1H); 7.7 (dd, 2H); 7.65 (broad t, 1H); 7.30 (t, 2H); 6.90 (d, 1H); 5.30 (s, 2H); 4.35 (broad d, 2H); 3.1 (m, 2H); 2.85 (broad t, 2H); 2.75 (q, 2H); 1.75 (broad d, 2H); 1.60 (m, 1H); 1.45 (m, 2H); 1.25 (t, 3H); 1.15 (m, 2H). | 454 | 0.93 | A |
| 6 | (DMSO) δ (ppm): 8.0 (d, 1H); 7.75 (m, 3H); 7.55 (m, 5H); 7.30 (m, 2H); 5.0 (s, 2H); 4.55 (broad d, 2H); 3.10 (m, 2H); 2.90 (broad t, 2H); 2.5 (s, 3H); 1.75 (broad d, 2H); 1.60 (m, 1H); 1.4 (m, 2H); 1.15 (m, 2H). | 505 | 1.04 | A |

TABLE 2-continued

| No. | ¹H NMR | LC-MS M + H | RT | Method |
|---|---|---|---|---|
| 7 | (DMSO) δ (ppm): 8.40 (s, 1H); 7.8 (d, 1H); 7.65 (dd, 2H); 7.55 (broad t, 1H); 7.25 (t, 2H); 6.90 (d, 1H); 5.30 (s, 2H); 4.30 (broad d, 2H); 3.10 (m, 3H); 2.80 (broad t, 2H); 1.75 (broad d, 2H); 1.60 (m, 1H); 1.4 (m, 2H); 1.25 (d, 6H); 1.15 (m, 2H). | 468 | 0.98 | A |
| 8 | (DMSO) δ (ppm): 8.40 (s, 1H); 7.8 (d, 1H); 7.65 (m, 3H); 7.25 (t, 2H); 7.15 (broad t, 1H); 6.90 (d, 1H); 6.2 (s, 1H); 4.95 (s, 2H); 4.30 (broad d, 2H); 3.80 (s, 3H); 3.05 (m, 2H); 2.80 (broad t, 2H); 1.75 (broad d, 2H); 1.60 (m, 1H); 1.4 (m, 2H); 1.15 (m, 2H). | 438 | 0.85 | A |
| 9 | (DMSO) δ (ppm): 9.15 (s, 1H); 8.4 (s, 1H); 7.8 (d, 1H); 7.7 (dd, 2H); 7.40 (broad t, 1H); 7.25 (t, 2H); 6.90 (d, 1H); 5.5 (s, 2H); 4.35 (broad d, 2H); 3.1 (m, 2H); 2.85 (broad t, 2H); 1.75 (broad d, 2H); 1.55 (m, 1H); 1.4 (m, 2H); 1.15 (m, 2H). | 442 | 0.87 | A |
| 10 | (DMSO) δ (ppm): 8.40 (s, 1H); 7.80 (d, 1H); 7.70 (dd, 2H); 7.50 (broad t, 1H); 7.30 (t, 2H); 6.90 (d, 1H); 5.40 (s, 2H); 4.35 (broad d, 2H); 3.10 (m, 2H); 2.80 (broad t, 2H); 1.75 (broad d, 2H); 1.55 (m, 1H); 1.45 (m, 11H); 1.15 (m, 2H). | 498 | 0.99 | A |
| 11 | (DMSO) δ (ppm): 8.40 (s, 1H); 7.80 (d, 1H); 7.65 (dd, 2H); 7.45 (broad t, 1H); 7.25 (t, 2H); 6.90 (d, 1H); 5.15 (s, 2H); 4.30 (broad d, 2H); 3.30 (m, 1H); 3.10 (m, 2H); 2.80 (broad t, 2H); 1.75 (broad d, 2H); 1.60 (m, 1H); 1.40 (m, 2H); 1.30 (d, 6H); 1.10 (m, 2H). | 468 | 0.97 | A |
| 12 | (DMSO) δ (ppm): 8.10 (dd, 2H); 8.0 (d, 1H); 7.80 (s, 1H); 7.60-7.40 (m, 5H); 7.25 (d, 1H); 5.30 (s, 2H); 4.50 (broad d, 2H); 3.10 (m, 2H); 2.85 (broad t, 2H); 1.80 (broad d, 2H); 1.60 (m, 1H); 1.40 (m, 2H); 1.15 (m, 2H). | 510 | 0.97 | A |
| 13 | (DMSO) δ (ppm): 8.05 (m, 3H); 7.80 (d, 1H); 7.70 (d, 2H); 7.65-7.45 (m, 3H); 7.25 (d, 1H); 5.30 (s, 2H); 4.50 (broad d, 2H); 3.10 (m, 2H); 2.85 (broad t, 2H); 1.75 (broad d, 2H); 1.60 (m, 1H); 1.40 (m, 2H); 1.15 (m, 2H). | 526 | 1.02 | A |
| 14 | (DMSO) δ (ppm): 8.0 (d, 1H); 7.95 (d, 2H); 7.80 (s, 1H); 7.55 (broad t, 1H); 7.50 (q, 2H); 7.30 (d, 1H); 7.15 (d, 2H); 5.30 (s, 2H); 4.50 (broad d, 2H); 3.85 (s, 3H); 3.10 (m, 2H); 2.85 (broad t, 2H); 1.80 (broad d, 2H); 1.60 (m, 1H); 1.40 (m, 2H); 1.15 (m, 2H). | 522 | 0.95 | A |
| 15 | (DMSO) δ (ppm): 8.15 (dd, 2H); 7.95 (d, 1H); 7.75 (s, 1H); 7.65 (broad t, 1H); 7.50 (q, 2H); 7.4 (t, 2H); 7.25 (d, 1H); 5.40 (s, 2H); 4.50 (broad d, 2H); 3.10 (m, 2H); 2.85 (broad t, 2H); 1.75 (broad d, 2H); 1.60 (m, 1H); 1.40 (m, 2H); 1.15 (m, 2H). | 510 | 1.06 | A |
| 16 | (DMSO) δ (ppm): 8.0 (d, 1H); 7.85 (d, 1H); 7.80 (s, 1H); 7.75 (dd, 1H); 7.65 (m, 2H); 7.50 (q, 2H); 7.45 (m, 1H); 7.25 (d, 1H); 5.40 (s, 2H); 4.50 (broad d, 2H); 3.10 (m, 2H); 2.85 (broad t, 2H); 1.80 (broad d, 2H); 1.60 (m, 1H); 1.40 (m, 2H); 1.15 (m, 2H). | 510 | 1.06 | A |
| 17 | (DMSO) δ (ppm): 8.05 (d, 2H); 8.0 (d, 1H); 7.80 (s, 1H); 7.65 (d, 2H); 7.50 (q, 2H); 7.45 (broad t, 1H); 7.25 (d, 1H); 5.30 (s, 2H); 4.50 (broad d, 2H); 3.15 (m, 2H); 2.85 (broad t, 2H); 1.80 (broad d, 2H); 1.60 (m, 1H); 1.40 (m, 2H); 1.15 (m, 2H). | 542 | 1.12 | A |
| 18 | (DMSO) δ (ppm): 9.15 (s, 1H); 8.0 (d, 1H); 7.75 (s, 1H); 7.50 (q, 2H); 7.35 (broad t, 1H); 7.25 (d, 1H); 5.50 (s, 2H); 4.50 (broad d, 2H); 3.10 (m, 2H); 2.90 (broad t, 2H); 1.80 (broad d, 2H); 1.60 (m, 1H); 1.40 (m, 2H); 1.15 (m, 2H). | 432 | 0.84 | A |
| 19 | (DMSO) δ (ppm): 8.45 (s, 1H); 8.15 (broad s, 1H); 7.85 (m, 2H); 7.70 (dd, 2H); 7.45 (broad t, 1H); 7.30 (t, 2H); 6.90 (d, 1H); 6.8 (s, 1H); 5.20 (s, 2H); 4.40 (broad d, 2H); 3.10 (m, 2H); 2.85 (broad t, 2H); 1.80 (broad d, 2H); 1.60 (m, 1H); 1.40 (m, 2H); 1.15 (m, 2H). | 468 | 0.82 | A |
| 20 | (DMSO) δ (ppm): 8.70 (broad s, 1H); 8.0 (d, 1H); 7.80 (s, 1H); 7.55 (q, 2H); 7.45 (broad t, 1H); 7.30 (d, 1H); 6.80 (s, 1H); 5.20 (s, 2H); 4.50 (broad d, 2H); 3.10 (m, 2H); 2.90 (broad t, 2H); 2.80 (d, 3H); 1.80 (broad d, 2H); 1.60 (m, 1H); 1.40 (m, 2H); 1.15 (m, 2H). | 472 | 0.82 | A |
| 21 | (DMSO) δ (ppm): 8.80 (s, 1H); 8.40 (s, 1H); 7.80 (dd, 1H); 7.65 (m, 3H); 7.45 (m, 2H); 7.25 (t, 2H); 6.85 (d, 1H); 5.10 (s, 2H); 4.30 (broad d, 2H); 3.10 (m, 2H); 2.75 (broad t, 2H); 1.75 (broad d, 2H); 1.55 (m, 1H); 1.35 (m, 2H); 1.10 (m, 2H). | 468 | 0.8 | A |
| 22 | (DMSO) δ (ppm): 8.70 (broad s, 1H); 8.05 (dd, 2H); 7.60 (dd, 1H); 7.45 (broad t, 1H); 7.30 (t, 2H); 7.15 (d, 1H); 6.80 (s, 1H); 6.75 (s, 1H); 5.20 (s, 2H); 4.40 (broad d, 2H); 3.10 (m, 2H); 2.85 (broad t, 2H); 2.80 (d, 3H); 1.75 (broad d, 2H); 1.60 (m, 1H); 1.40 (m, 2H); 1.15 (m, 2H). | 482 | 0.95 | A |
| 23 | (DMSO) δ (ppm): 8.15 (broad s, 1H); 8.05 (d, 1H); 7.80 (broad s, 1H); 7.55 (dd, 1H); 7.50 (dd, 1H); 7.40 (m, 2H); | 442 | 0.73 | A |

TABLE 2-continued

| No. | ¹H NMR | LC-MS M + H | RT | Method |
|---|---|---|---|---|
|  | 7.30 (d, 1H); 6.75 (s, 1H); 5.20 (s, 2H); 4.50 (broad d, 2H); 3.10 (m, 2H); 2.90 (broad t, 2H); 1.75 (broad d, 2H); 1.60 (m, 1H); 1.40 (m, 2H); 1.15 (m, 2H). | | | |
| 24 | (DMSO) δ (ppm): 8.10 (broad s, 1H); 8.05 (dd, 2H); 7.80 (broad s, 1H); 7.60 (dd, 1H); 7.45 (broad t, 1H); 7.30 (dd, 2H); 7.15 (d, 1H); 6.80 (s, 1H); 6.75 (s, 1H); 5.20 (s, 2H); 4.40 (broad d, 2H); 3.15 (m, 2H); 2.85 (broad t, 2H); 1.80 (broad d, 2H); 1.60 (m, 1H); 1.40 (m, 2H); 1.15 (m, 2H). | 468 | 0.92 | A |
| 25 | (DMSO) δ (ppm): 8.70 (broad s, 1H); 8.0 (d, 1H); 7.55 (dd, 1H); 7.50 (dd, 1H); 7.40 (m, 2H); 7.30 (d, 1H); 6.80 (s, 1H); 5.20 (s, 2H); 4.50 (broad d, 2H); 3.10 (m, 2H); 2.85 (broad t, 2H); 2.75 (d, 3H); 1.75 (broad d, 2H); 1.60 (m, 1H); 1.40 (m, 2H); 1.15 (m, 2H). | 456 | 0.75 | A |
| 26 | (DMSO) δ (ppm): 8.75 (broad s, 1H); 8.40 (s, 1H); 7.80 (d, 1H); 7.65 (dd, 2H); 7.45 (broad t, 1H); 7.25 (t, 2H); 6.90 (d, 1H); 6.80 (s, 1H); 5.20 (s, 2H); 4.40 (broad d, 2H); 3.10 (m, 2H); 2.80 (broad t, 2H); 2.75 (d, 3H); 1.75 (broad d, 2H); 1.60 (m, 1H); 1.40 (m, 2H); 1.15 (m, 2H). | 482 | 0.85 | A |
| 27 | (DMSO) δ (ppm): 8.10 (dd, 2H); 7.60 (dd, 1H); 7.45 (broad t, 1H); 7.30 (dd, 2H); 7.15 (d, 1H); 6.80 (d, 1H); 6.70 (s, 1H); 5.20 (s, 2H); 4.40 (broad d, 2H); 3.10 (m, 2H); 3.05 (s, 3H); 3.0 (s, 3H); 2.80 (broad t, 2H); 1.80 (broad d, 2H); 1.60 (m, 1H); 1.40 (m, 2H); 1.15 (m, 2H). | 496 | 0.99 | A |
| 28 | (DMSO) δ (ppm): 8.50 (s, 1H); 8.15 (broad s, 1H); 7.90 (dd, 1H); 7.80 (broad s, 1H); 7.70-7.40 (m, 4H); 7.15 (m, 1H); 6.90 (d, 1H); 6.80 (s, 1H); 5.20 (s, 2H); 4.35 (broad d, 2H); 3.10 (m, 2H); 2.85 (broad t, 2H); 1.80 (broad d, 2H); 1.60 (m, 1H); 1.40 (m, 2H); 1.15 (m, 2H). | 468 | 0.82 | A |
| 29 | (DMSO) δ (ppm): 8.70 (s, 1H); 7.60 (dd, 2H); 7.50 (d, 2H); 7.40 (broad t, 1H); 7.25 (t, 2H); 7.0 (d, 2H); 6.90 (s, 1H); 5.20 (s, 2H); 3.75 (broad d, 2H); 3.10 (m, 2H); 2.75 (d, 3H); 2.65 (broad t, 2H); 1.75 (broad d, 2H); 1.45 (m, 3H); 1.15 (m, 2H). | 481 | 0.91 | A |
| 30 | (DMSO) δ (ppm): 8.40 (s, 1H); 7.80 (d, 1H); 7.65 (dd, 2H); 7.45 (broad t, 1H); 7.30 (t, 2H); 6.90 (d, 1H); 6.70 (s, 1H); 5.20 (s, 2H); 4.30 (broad d, 2H); 3.15 (m, 2H); 3.10 (s, 3H); 3.05 (s, 3H); 2.80 (broad t, 2H); 1.75 (broad d, 2H); 1.60 (m, 1H); 1.40 (m, 2H); 1.15 (m, 2H). | 496 | 0.89 | A |
| 31 | (DMSO) δ (ppm): 8.0 (d, 1H); 7.80 (s, 1H); 7.50 (q, 2H); 7.45 (broad t, 1H); 7.30 (d, 1H); 6.70 (s, 1H); 5.20 (s, 2H); 4.55 (broad d, 2H); 3.15 (m, 2H); 3.10 (s, 3H); 3.05 (s, 3H); 2.90 (broad t, 2H); 1.80 (broad d, 2H); 1.60 (m, 1H); 1.40 (m, 2H); 1.15 (m, 2H). | 486 | 0.86 | A |
| 32 | (DMSO) δ (ppm): 8.70 (broad s, 1H); 8.4 (s, 1H); 8.3 (s, 1H); 8.150 (dd, 2H); 7.45 (broad t, 1H); 7.35 (t, 2H); 6.80 (s, 1H); 5.20 (s, 2H); 4.45 (broad d, 2H); 3.10 (m, 2H); 2.90 (broad t, 2H); 2.75 (d, 3H); 1.80 (broad d, 2H); 1.60 (m, 1H); 1.40 (m, 2H); 1.15 (m, 2H). | 483 | 1.09 | A |
| 33 | (DMSO) δ (ppm): 8.40 (s, 1H); 8.30 (s, 1H); 8.15 (m, 3H); 7.85 (m, 1H); 7.45 (m, 1H); 7.35 (m, 2H); 6.80 (s, 1H); 5.25 (m, 2H); 4.45 (m, 2H); 3.10 (m, 2H); 2.80 (m, 2H); 1.80 (m, 2H); 1.60 (m, 1H); 1.40 (m, 2H); 1.20 (m, 2H). | 469 | 1.06 | A |
| 34 | (DMSO) δ (ppm): 8.40 (s, 1H); 8.30 (s, 1H); 8.15 (m, 2H); 7.45 (m, 1H); 7.35 (m, 2H); 6.70 (s, 1H); 5.25 (m, 2H); 4.45 (m, 2H); 3.15-3.00 (m, 8H); 2.90 (m, 2H); 1.80 (m, 2H); 1.60 (m, 1H); 1.40 (m, 2H); 1.20 (m, 2H). | 497 | 1.13 | A |
| 35 | (DMSO) δ (ppm): 8.75-8.60 (m, 3H); 7.70 (m, 2H); 7.45 (m, 1H); 7.30 (t, 2H); 6.80 (s, 1H); 5.20 (m, 2H); 4.70 (m, 2H); 3.10 (m, 2H); 3.90 (m, 2H); 2.90 (m, 3H); 1.75 (m, 2H); 1.60 (m, 1H); 1.4 (m, 2H); 1.10 (m, 2H). | 483 | 1.13 | A |
| 36 | (DMSO) δ (ppm): 8.70 (m, 2H); 7.70 (m, 2H); 7.45 (m, 1H); 7.30 (m, 2H); 6.70 (s, 1H); 5.20 (m, 2H); 4.70 (m, 2H); 3.15-3.00 (m, 8H); 3.00-2.80 (m, 2H); 1.75 (m, 2H); 1.65 (m, 1H); 1.40 (m, 2H); 1.10 (m, 2H). | 497 | 1.16 | A |
| 37 | (DMSO) δ (ppm): 8.80-8.60 (m, 2H); 7.45 (m, 1H); 7.00 (m, 1H); 6.80 (s, 1H); 5.20 (m, 2H); 4.65 (m, 2H); 3.10 (m, 2H); 2.95 (m, 2H); 2.80 (m, 3H); 1.80 (m, 2H); 1.60 (m, 1H); 1.40 (m, 2H); 1.10 (m, 2H). | 457 | 1.44 | A |
| 38 | (DMSO) δ (ppm): 8.65 (m, 1H); 8.15 (m, 1H); 7.85 (m, 1H); 7.45 (m, 1H); 6.95 (m, 1H); 6.80 (s, 1H); 5.20 (m, 2H); 4.65 (m, 2H); 3.10 (m, 2H); 2.95 (m, 2H); 1.80 (m, 2H); 1.60 (m, 1H); 1.40 (m, 2H); 1.10 (m, 2H). | 443 | 1.39 | A |
| 39 | (DMSO) δ (ppm): 8.70 (s, 2H); 8.15 (m, 1H); 7.85 (m, 1H); 7.70 (m, 2H); 7.45 (m, 1H); 7.30 (m, 2H); 6.75 (s, 1H); 5.20 (m, 2H); 4.70 (m, 2H); 3.10 (m, 2H); 2.90 (m, 2H); 1.75 (m, 2H); 1.60 (m, 1H); 1.40 (m, 2H); 1.10 (m, 2H). | 469 | 1.33 | A |

TABLE 2-continued

| No. | ¹H NMR | M + H | RT | Method |
|---|---|---|---|---|
| | | LC-MS | | |
| 40 | (DMSO) δ (ppm): 8.65 (m, 1H); 7.45 (m, 1H); 6.95 (m, 1H); 6.70 (s, 1H); 5.20 (m, 2H); 4.65 (m, 2H); 3.20 (m, 5H); 3.05 (s, 3H); 2.90 (m, 2H); 1.80 (m, 2H); 1.60 (m, 1H); 1.40 (m, 2H); 1.10 (m, 2H). | 471 | 1.4 | A |
| 41 | (DMSO) δ (ppm): 8.25-8.00 (m, 3H); 7.90 (m, 1H); 7.85 (m, 1H); 7.55-7.25 (m, 4H); 6.80 (s, 1H); 5.25 (m, 2H); 4.45 (m, 2H); 3.10 (m, 2H); 2.95 (m, 2H); 1.80 (m, 2H); 1.65 (m, 1H); 1.40 (m, 2H); 1.20 (m, 2H). | 469 | 0.84 | A |
| 42 | (DMSO) δ (ppm): 8.60 (m, 1H); 8.40 (s, 1H); 7.80 (m, 1H); 7.65 (m, 2H); 7.45 (m, 1H); 7.30 (m, 2H); 6.90 (m, 1H); 6.80 (s, 1H); 5.20 (m, 2H); 4.35 (m, 2H); 3.30 (m, 2H); 3.10 (m, 2H); 2.80 (m, 2H); 2.40 (m, 2H); 2.10 (s, 6H); 1.75 (m, 2H); 1.60 (m, 1H); 1.40 (m, 2H); 1.15 (m, 2H). | 539 | 0.81 | A |
| 43 | (DMSO) δ (ppm): 8.10 (m, 1H); 7.95-7.75 (m, 2H); 7.50-7.25 (m, 2H); 6.75 (m, 2H); 5.20 (m, 2H); 4.20 (m, 2H); 3.10 (m, 2H); 2.70 (m, 2H); 2.30 (d, 2H); 1.85-1.65 (m, 3H); 1.60-1.30 (m, 3H); 1.10 (m, 2H); 0.85 (m, 6H). | 430 | 0.9 | A |
| 44 | (DMSO) δ (ppm): 8.00 (m, 1H); 7.90-7.80 (m, 2H); 7.45 (m, 1H); 7.30 (m, 1H); 6.75 (m, 2H); 5.20 (m, 2H); 4.20 (m, 2H); 3.10 (m, 2H); 2.70 (m, 2H); 2.35 (s, 2H); 1.75 (m, 2H); 1.60-1.30 (m, 3H); 1.10 (m, 2H; 0.85 (s, 9H). | 444 | 0.95 | A |
| 45 | (DMSO) δ (ppm): 8.40 (s, 1H); 8.15 (broad s, 1H); 7.80 (m, 2H); 7.40 (m, 2H); 7.30 (t, 1H); 7.10 (d, 1H); 6.90 (d, 1H); 6.75 (s, 1H); 5.20 (s, 2H); 4.30 (d, 2H); 3.10 (t, 2H); 2.80 (t, 2H); 2.35 (s, 3H); 1.75 (d, 2H); 1.60 (m, 1H); 1.40 (q, 2H); 1.10 (q, 2H). | 464 | 0.8 | A |
| 46 | (DMSO) δ (ppm): 8.25 (s, 1H); 8.10 (broad d, 1H); 7.70 (m, 2H); 7.40-7.30 (m, 3H); 6.80 (s, 1H); 5.25 (s, 2H); 4.30 (m, 2H); 3.85-3.35 (m, 8H); 3.20-2.90 (m, 4H); 2.85 (s, 3H); 1.80 (d, 2H); 1.65 (m, 1H); 1.40 (m, 2H); 1.30-1.10 (m, 2H). | 551 | 0.82 | A |
| 47 | (DMSO) δ (ppm): 8.50 (s, 1H); 8.15 (broad s, 1H); 7.90 (d, 1H); 7.85 (broad s, 1H); 7.70 (d, 1H); 7.60 (m, 2H); 7.55 (m, 1H); 7.30 (d, 1H); 6.95 (d, 1H); 6.80 (s, 1H); 5.20 (s, 2H); 4.35 (d, 2H); 3.10 (m, 2H); 2.85 (t, 2H); 1.75 (d, 2H); 1.60 (m, 1H); 1.40 (m, 2H); 1.15 (m, 2H). | 534 | 1.03 | A |
| 48 | (DMSO) δ (ppm): 8.40 (s, 1H); 8.15 (s, 1H); 7.85 (m, 2H); 7.70 (s, 1H); 7.60 (m, 1H); 7.50-7.20 (m, 3H); 6.85 (d, 1H); 6.75 (s, 1H); 5.20 (s, 2H); 4.30 (d, 2H); 3.05 (m, 2H); 2.80 (m, 2H); 1.70 (d, 2H); 1.55 (m, 1H); 1.35 (m, 2H); 1.10 (m, 2H). | 484 | 0.96 | A |
| 49 | (DMSO) δ (ppm): 8.45 (s, 1H); 8.15 (broad s, 1H); 7.85 (m, 2H); 7.45 (m, 1H); 7.05 (m, 2H); 6.90 (d, 1H); 6.75 (m, 2H); 5.20 (s, 2H); 4.35 (m, 2H); 3.85 (s, 3H); 3.10 (m, 2H); 2.85 (m, 2H); 1.75 (m, 2H); 1.60 (m, 1H); 1.40 (m, 2H); 1.10 (q, 2H). | 498 | 0.93 | A |
| 50 | (DMSO) δ (ppm): 8.35 (s, 1H); 8.15 (broad s, 1H); 7.80 (broad s, 1H); 7.75 (d, 1H); 7.45 (t, 1H); 7.20 (s, 1H); 7.10 (d, 1H); 7.00 (d, 1H); 6.90 (d, 1H); 6.80 (s, 1H); 6.05 (s, 2H); 5.20 (s, 2H); 4.30 (d, 2H); 3.10 (m, 2H); 2.80 (t, 2H); 1.75 (d, 2H); 1.55 (m, 1H); 1.40 (m, 2H); 1.15 (m, 2H). | 494 | 0.88 | A |
| 51 | (DMSO) δ (ppm): 8.70 (m, 1H); 7.75 (m, 1H); 7.00 (m, 1H); 6.90 (s, 1H); 5.25 (m, 2H); 4.50-4.30 (m, 4H); 3.40-3.15 (m, 4H); 1.90-1.50 (m, 4H); 1.35 (m, 3H). | 476 | 1.36 | A |
| 52 | (DMSO) δ (ppm): 8.65 (d, 1H); 7.60 (d, 1H); 7.15 (m, 1H); 6.95 (d, 1H); 6.20 (d, 1H); 4.90 (m, 2H); 4.60 (m, 2H); 3.80 (s, 3H); 3.05-2.80 (m, 4H); 1.80-1.65 (m, 2H); 1.60-1.35 (m, 3H); 1.20 (m, 2H); 1.05 (m, 3H). | 427 | 1.33 | A |
| 53 | (DMSO) δ (ppm): 8.40 (broad s, 1H); 8.00 (broad s, 2H); 7.85 (broad s, 1H); 7.75 (d, 1H); 7.55 (d, 1H); 6.85 (s, 1H); 5.20 (s, 2H); 4.50 (broad d, 2H); 3.55 (m, 2H); 3.10 (m, 2H); 1.90 (m, 2H); 1.70 (m, 1H); 1.40 (m, 2H); 1.25 (m, 2H). | 459 | 0.84 | A |
| 54 | (DMSO) δ (ppm): 8.90 (s, 1H); 7.90 (s, 1H); 7.65-7.50 (m, 3H); 5.65 (m, 2H); 4.60 (m, 2H); 3.30 (m, 1H); 3.10-2.90 (m, 4H); 1.85-1.70 (m, 3H); 1.35 (d, 6H); 1.20 (m, 2H). | 445 | 1.31 | A |
| 55 | (DMSO) δ (ppm): 8.70 (m, 1H); 7.55 (m, 1H); 7.00 (m, 1H); 5.15 (m, 2H); 4.65 (m, 2H); 3.30 (m, 1H); 3.00-2.90 (m, 4H); 1.80-1.80 (m, 3H); 1.35 (m, 6H); 1.10 (m, 2H). | 429 | 1.37 | A |
| 56 | (DMSO) δ (ppm): 8.05 (d, 1H); 7.90-7.70 (m, 2H); 7.60-7.50 (m, 2H); 7.35 (d, 1H); 8.90 (s, 1H); 5.25 (m, 2H); 4.45-4.30 (m, 4H); 3.40-3.20 (m, 4H); 1.90-1.60 (m, 4H); 1.35 (t, 3H). | 491 | 1.00 | A |
| 57 | (DMSO) δ (ppm): 8.70 (m, 2H); 7.75 (m, 1H); 7.00 (m, 1H); 6.80 (s, 1H); 5.20 (m, 2H); 4.45 (m, 2H); 3.40-3.20 (m, 4H); 2.80 (m, 3H); 1.90-1.55 (m, 4H). | 461 | 1.19 | A |
| 58 | (DMSO) δ (ppm): 8.40 (m, 2H); 7.60-7.50 (m, 2H); 5.15 (m, 2H); 3.40-3.25 (m, 3H); 3.05-2.80 (m, 4H); 1.80 (m, 2H); 1.65 (m, 1H); 1.40-1.20 (m, 8H). | 472 | 1.44 | A |

TABLE 2-continued

| No. | ¹H NMR | LC-MS M + H | RT | Method |
|---|---|---|---|---|
| 59 | (DMSO) δ (ppm): 8.20 (m, 1H); 8.00-8.20 (m, 3H); 7.60 (t, 1H); 5.15 (s, 2H); 3.85 (d, 2H); 3.30 (m, 1H); 3.00 (m, 4H); 1.85 (m, 2H); 1.75 (m, 1H); 1.60-1.40 (m, 2H); 1.30 (m, 6H). | 445 | 1.06 | A |
| 60 | (DMSO) δ (ppm): 8.70 (broad s, 2H); 7.45 (t, 1H); 7.10 (m, 1H); 6.80 (s, 1H); 5.20 (s, 2H); 4.10 (d, 2H); 3.80 (d, 2H); 3.10 (m, 2H); 2.80 (s, 3H); 2.20 (s, 6H); 1.90 (m, 2H). | 472 | 0.77 | A |
| 61 | (DMSO) δ (ppm): 8.70 (m, 2H); 7.45 (m, 1H); 7.00 (m, 1H); 6.80 (s, 1H); 5.20 (s, 2H); 3.90-3.60 (m, 4H); 3.10 (m, 2H); 2.80 (m, 3H); 1.50 (m, 6H); 1.40 (m, 6H); 0.80 (m, 3H). | 485 | 1.39 | A |
| 62 | (DMSO) δ (ppm): 8.70 (m, 2H); 7.35 (t, 1H); 6.95 (m, 1H); 6.80 (s, 1H); 5.20 (m, 2H); 4.50 (s, 1H); 4.30 (m, 2H); 3.40 (m, 2H); 3.20 (m, 2H); 2.80 (m, 3H); 1.90 (m, 4H); 1.45 (m, 2H). | 473 | 1.14 | A |
| 63 | (DMSO) δ (ppm): 8.20 (m, 1H); 8.05 (m, 1H); 7.90 (m, 1H); 7.80 (broad s, 1H); 7.20 (m, 1H); 6.90 (s, 1H); 6.40 (m, 1H); 4.40 (broad s, 2H); 4.20 (broad s, 2H); 3.70 (s, 3H); 3.20 (m, 2H); 2.30 (m, 6H); 1.95 (m, 2H). | 512 | 0.74 | A |
| 64 | (DMSO) δ (ppm): 8.80 (s, 1H); 8.70 (m, 1H); 7.90 (s, 1H); 7.60 (s, 2H); 7.40 (m, 1H); 6.80 (s, 1H); 5.20 (s, 2H); 3.90-3.60 (m, 4H); 3.00 (m, 2H); 2.80 (m, 3H); 1.50-1.30 (m, 8H); 0.80 (t, 3H). | 501 | 1.33 | A |
| 65 | (DMSO) δ (ppm): 8.80 (s, 1H); 8.70 (m, 1H); 7.90 (s, 1H); 7.60 (s, 2H); 7.40 (m, 1H); 6.80 (s, 1H); 5.20 (s, 2H); 3.90 (m, 2H); 3.70 (m, 2H); 3.10 (m, 2H); 2.80 (m, 3H); 1.80 (m, 1H); 1.60-1.40 (m, 6H); 1.30 (m, 2H); 0.90 (d, 6H). | 529 | 5.13 | B |
| 66 | (DMSO) δ (ppm): 8.70 (s, 1H); 8.40 (m, 2H); 7.60 (d, 1H); 7.40 (t, 1H); 6.80 (s, 1H); 5.20 (s, 2H); 3.20-3.00 (m, 6H); 2.80 (m, 3H); 1.70 (m, 1H); 1.60-1.40 (m, 6H); 1.30 (m, 2H); 0.90 (d, 6H). | 556 | 1.54 | A |
| 67 | (DMSO) δ (ppm): 8.15 (d, 1H); 8.05 (d, 1H); 7.90 (d, 1H); 7.70 (m, 1H); 7.60 (m, 2H); 7.35 (d, 1H); 5.20 (s, 2H); 3.75 (d, 2H); 3.30 (m, 1H); 3.10 (m, 2H); 2.90 (t, 2H); 1.85 (d, 2H); 1.70 (m, 1H); 1.45 (m, 2H); 1.30 (d, 6H). | 410 | 0.92 | A |
| 68 | (DMSO) δ (ppm): 8.70 (s, 1H); 8.40 (s, 1H); 8.15 (broad s, 1H); 8.00 (m, 2H); 7.80 (broad s, 1H); 7.45 (m, 1H); 7.30 (m, 2H); 6.80 (s, 1H); 5.25 (m, 2H); 4.40 (m, 2H); 3.10 (m, 2H); 2.90 (m, 2H); 1.80 (m, 2H); 1.60 (m, 1H); 1.40 (m, 2H); 1.20 (m, 2H). | 469 | 1.20 | A |
| 69 | (DMSO) δ (ppm): 8.75 (broad s, 1H); 8.70 (s, 1H); 8.40 (s, 1H); 8.00 (m, 2H); 7.45 (broad s, 1H); 7.30 (t, 2H); 6.85 (s, 1H); 5.25 (m, 2H); 4.40 (m, 2H); 3.10 (m, 2H); 2.90 (m, 2H); 2.75 (s, 3H); 1.80 (m, 2H); 1.60 (m, 1H); 1.40 (m, 2H); 1.20 (m, 2H). | 483 | 1.24 | A |
| 70 | (DMSO) δ (ppm): 8.80-8.60 (m, 2H); 7.55 (m, 1H); 7.00 (m, 1H); 6.80 (s, 1H); 5.20 (s, 2H); 4.50 (m, 2H); 3.70 (m, 1H); 3.15 (m, 2H); 2.80 (s, 3H); 1.90 (m, 2H); 1.40 (m, 2H). | 429 | 1.18 | A |
| 71 | (DMSO) δ (ppm): 8.00 (d, 1H); 7.80 (s, 1H); 7.45-7.55 (m, 3H); 7.30 (d, 1H); 6.90 (s, 1H); 5.20 (s, 2H); 4.55 (m, 2H); 4.40 (q, 2H); 3.10 (m, 2H); 2.90 (m, 2H); 1.80 (m, 2H); 1.60 (m, 1H); 1.40 (m, 2H); 1.30 (t, 3H); 1.15 (m, 2H). | 487 | 1.05 | A |
| 72 | (DMSO) δ (ppm): 8.80-8.60 (m, 2H); 7.45 (m, 1H); 6.95 (m, 1H); 6.80 (s, 1H); 5.20 (s, 2H); 3.95 (m, 2H); 3.60 (m, 2H); 3.10 (m, 2H); 2.80 (s, 3H); 1.50 (m, 2H); 1.40 (m, 4H); 1.00 (s, 3H). | 471 | 4.48 | B |
| 73 | (DMSO) δ (ppm): 8.10 (d, 1H); 7.85 (m, 1H); 7.80 (s, 1H); 7.50 (m, 2H); 7.30 (d, 1H); 7.25 (s, 1H); 6.95 (s, 1H); 6.45 (m, 1H); 4.40 (d, 2H); 3.75 (s, 3H); 3.10 (m, 2H); 2.90 (m, 2H); 1.80 (d, 2H); 1.60 (m, 1H); 1.40 (m, 2H); 1.10 (m, 2H). | 496 | 0.77 | A |
| 74 | (DMSO) δ (ppm): 8.70 (s, 1H); 8.10 (broad s, 1H); 7.90 (broad s, 1H); 7.50 (m, 1H); 7.00 (m, 1H); 6.80 (s, 1H); 5.20 (s, 2H); 3.90 (m, 1H); 3.75 (m, 2H); 3.55 (m, 2H); 2.00-185 (m, 2H); 1.80-1.65 (m, 3H); 1.40 (m, 1H). | 429 | 1.1 | A |
| 75 | (DMSO) δ (ppm): 8.70 (m, 1H); 8.20 (m, 1H); 8.10 (m, 3H); 7.65 (m, 1H); 6.80 (s, 1H); 5.25 (s, 2H); 3.80 (m, 2H); 3.60 (m, 1H); 3.15 (m, 2H); 2.80 (s, 3H); 2.00 (m, 2H); 1.75 (m, 2H). | 445 | 3.52 | B |
| 76 | (DMSO) δ (ppm): 8.70 (m, 1H); 8.40 (m, 2H); 7.60 (m, 2H); 6.80 (s, 1H); 5.20 (s, 2H); 3.30 (m, 2H); 3.60 (m, 1H); 3.05 (m, 2H); 2.80 (s, 3H); 1.90 (m, 2H); 1.60 (m, 2H). | 472 | 4.30 | B |
| 77 | (DMSO) δ (ppm): 8.90 (s, 1H); 8.70 (m, 1H); 7.90 (s, 1H); 7.60 (m, 2H); 7.55 (broad d, 1H); 6.80 (s, 1H); 5.20 (s, 2H); 4.50 (m, 2H); 3.70 (s, 1H); 3.20 (m, 2H); 2.80 (s, 3H); 1.90 (m, 2H); 1.50 (m, 2H). | 445 | 4.02 | B |
| 78 | (DMSO) δ (ppm): 8.90 (s, 1H); 8.70 (broad s, 1H); 7.90 (s, 1H); 7.60 (s, 2H); 7.40 (m, 1H); 6.80 (s, 1H); 5.20 (s, 2H); 3.95 (m, 2H); 3.60 (m, 2H); 3.10 (m, 2H); 2.80 (m, 3H); 1.60-1.40 (m, 6H); 1.00 (s, 3H). | 487 | 1.24 | A |

TABLE 2-continued

| No. | ¹H NMR | LC-MS | | |
|---|---|---|---|---|
| | | M + H | RT | Method |
| 79 | (DMSO) δ (ppm): 8.80 (m, 1H); 8.40 (m, 1H); 8.15 (m, 1H); 8.05 (m, 2H); 7.80 (m, 1H); 6.80 (s, 1H); 5.25 (s, 2H); 3.65 (m, 1H); 3.50 (m, 2H); 3.30 (m, 1H); 3.20(m, 2H); 2.80 (m, 4H); 2.05 (m, 1H); 1.70 (m, 1H). | 445 | 0.82 | A |
| 80 | (DMSO) δ (ppm): 8.00 (d, 1H); 7.80 (s, 1H); 7.65 (m, 2H); 7.50 (m, 2H); 7.30 (d, 1H); 7.10 (m, 1H); 6.50 (m, 1H); 5.65 (m, 1H); 4.50 (m, 2H); 3.05 (m, 2H); 2.85 (m, 2H); 1.75 (m, 3H); 1.60 (m, 3H); 1.35 (m, 2H); 1.10 (m, 2H); 0.90 (d, 6H). | 470 | 1.16 | A |
| 81 | (DMSO) δ (ppm): 8.10 (m, 2H); 7.60 (m, 3H); 7.30 (m, 2H); 7.20 (d, 1H); 7.10 (bt, 1H); 6.80 (d, 1H); 6.45 (m, 1H); 5.65 (m, 1H); 4.40 (m, 2H); 3.05 (m, 2H); 2.80 (m, 2H); 1.80 (m, 3H); 1.55 (m, 3H); 1.35 (m, 2H); 1.15 (m, 2H); 0.90 (d, 6H). | 480 | 1.25 | A |
| 82 | (DMSO) δ (ppm): 8.65 (d, 1H); 8.15 (bs, 1H); 7.85 (bs, 1H); 7.50 (bt, 1H); 7.05 (d, 1H); 6.80 (s, 1H); 5.20 (s, 2H); 4.20 (s, 2H); 3.70 (m, 2H); 3.10 (m, 2H); 2.75 (m, 1H); 1.80 (m, 2H). | 415 | 0.94 | A |
| 83 | (DMSO) δ (ppm): 8.70 (bs, 1H); 8.65 (d, 1H); 7.50 (bt, 1H); 7.05 (d, 1H); 6.80 (s, 1H); 5.20 (s, 2H); 4.20 (s, 2H); 3.70 (m, 2H); 3.05 (m, 2H); 2.80 (s, 3H); 2.70 (m, 1H); 1.80 (m, 2H). | 429 | 0.98 | A |
| 84 | (DMSO) δ (ppm): 8.70 (bs, 1H); 8.60 (bs, 1H); 8.05 (m, 1H); 7.00 (m, 1H); 6.80 (s, 1H); 5.25 (s, 2H); 3.45 (m, 2H); 3.30 (m, 3H); 3.10 (m, 1H); 2.50 (m, 1H); 2.80 (m, 3H); 2.00 (m, 1H); 1.70 (m, 1H). | 429 | 1.00 | A |
| 85 | (DMSO) δ (ppm): 8.70 (bs, 1H); 8.60 (bs, 1H); 8.05 (m, 1H); 7.00 (m, 1H); 6.80 (s, 1H); 5.25 (s, 2H); 3.45 (m, 2H); 3.30 (m, 3H); 3.10 (m, 1H); 2.80 (m, 3H); 2.50 (m, 1H); 2.00 (m, 1H); 1.70 (m, 1H). | 429 | 1.01 | A |

The compounds of the invention underwent pharmacological tests to determine their inhibitory effect on the enzyme FAAH (Fatty Acid Amide Hydrolase).

Protocol 1: The inhibitory activity was demonstrated in a radioenzymatic test based on measuring the product of hydrolysis of anandamide [ethanolamine 1-³H] with FAAH (*Life Sciences* (1995), 56, 1999-2005 and *Journal of Biochemical and Biophysical Methods* (2004), 60(2), 171-177). Thus, mouse brains (minus the cerebellum) are removed and stored at −80° C. The membrane homogenates are prepared extemporaneously by homogenizing the tissues using a Precellys® machine in reaction buffer (10 mM Tris-HCl, pH=8, 150 mM NaCl and 1 mM ethylenediaminetetraacetic acid (EDTA)). The enzymatic reaction is performed in 96-well Multiscreen filtration plates in a final volume of 70 μL. Reaction buffer supplemented with fatty acid-free bovine serum albumin (BSA, 1 mg/ml) is used for the enzymatic reaction and the dilution of the compounds and of the anandamide [ethanolamine 1-³H]. The reaction buffer containing BSA (43 μL/well), the diluted test compounds at different concentrations (7 μL/well containing 1% DMSO) and the membrane preparation (10 μL/well, i.e. 200 pg of tissue per test) are successively added to the wells. After preincubation for 20 minutes of the compounds with the enzyme at 25° C., the reaction is started by adding anandamide [ethanolamine 1-³H]. (Specific activity of 15-20 Ci/mmol) diluted with cold anandamide (10 μL/well, final concentration of 10 μM, 0.01 ρCi per test). After incubation for 20 minutes at 25° C., the enzymatic reaction is stopped by adding a 5M solution of active charcoal prepared in 1.5M NaCl buffer and 0.5 M HCl (50 μL/well). The mixture is stirred for 10 minutes and the aqueous phase containing the ethanolamine [1-³H] is then recovered by filtration under vacuum and counted by liquid scintillation.

Protocol 2: The inhibitory activity was demonstrated via a fluorescent technique in an enzymatic test based on measuring the fluorescent product of hydrolysis of arachidonoyl 7-amino-4-methylcoumarin amide (AAMC) with FAAH (Analytical Biochemistry (2005), 343:143-151, J. of Biomolecular Screening (2006), 11(5): 519-527 and J. of Neurosciences Methods (2007), 161: 47-54). Thus, mouse brains (minus the cerebellum) are withdrawn and stored at −80° C. The brain homogenates are prepared extemporaneously by homogenizing the tissues using a Precellys® machine in reaction buffer (10 mM Tris-HCl, pH=8, 150 mM NaCl and 1 mM ethylenediaminetetraacetic acid (EDTA)). The enzymatic reaction is performed in black polystyrene 384-well plates in a final volume of 50 μL. Reaction buffer supplemented with fatty acid-free bovine serum albumin (BSA, 1 mg/ml) is used for the enzymatic reaction, the dilution of the compounds and the dilution of the AAMC. Reaction buffer containing the BSA (25 μL/well), the diluted test compounds at different concentrations (5 μL/well containing 1% DMSO) and the membrane preparation (10 μL/well, i.e. 200 μg of tissue per test) are successively added to the wells. After preincubation for 20 minutes of the compounds with the enzyme at 25° C., the reaction is started by adding 10 μL of substrate per well (AAMC, final concentration of 10 μM). After incubation for 40 minutes, the aminomethyl coumarin (AMC) produced is measured by fluorescent counting (Envision plate reader).

Under these conditions, the compounds of the invention that are the most active have $IC_{50}$ values (concentration that inhibits 50% of the control enzymatic activity of FAAH) of between 0.001 and 1 μM. Certain compounds have $IC_{50}$ values of less than 50 nM and more particularly less than 15 nM. Table 3 gives examples of the $IC_{50}$ values obtained with the compounds of the invention.

TABLE 3

| Compound No. | $IC_{50}$ (nM) | Protocol used |
|---|---|---|
| 1 | 1 | 1 |
| 2 | 40 | 1 |
| 5 | 2 | 1 |

TABLE 3-continued

| Compound No. | IC$_{50}$ (nM) | Protocol used |
|---|---|---|
| 9 | 2 | 1 |
| 12 | 47 | 1 |
| 19 | 1 | 1 |
| 29 | 0.7 | 2 |
| 38 | 2 | 1 |
| 41 | 0.6 | 1 |
| 46 | 16 | 1 |
| 52 | 28 | 1 |
| 64 | 3 | 1 |

It thus appears that the compounds according to the invention have inhibitory activity on the enzyme FAAH.

The in vivo activity of the compounds of the invention was evaluated in a test of analgesia.

Thus, the intraperitoneal (i.p.) administration of PBQ (phenylbenzoquinone, 2 mg/kg in 0.9% sodium chloride solution containing 5% ethanol) to male OF1 mice weighing 25 to 30 g causes abdominal stretching, on average 30 torsions or contractions within a period of 5 to 15 minutes after injection. The test compounds are administered orally (p.o.) or intraperitoneally (i.p.) suspended in Tween 80 at 0.5%, 60 minutes or 120 minutes before the administration of PBQ. Under these conditions, the compounds of the invention that are the most powerful reduce by 30% to 80% the number of stretches induced with PBQ, over a dose range of between 1 and 30 mg/kg.

For example, compounds 1 and 19 of the table reduce, respectively, by 55% and 30% the number of stretches induced with PBQ, at a dose of 30 mg/kg p.o. at 120 minutes.

The enzyme FAAH (Chemistry and Physics of Lipids, (2000), 108, 107-121) catalyses the hydrolysis of the endogenous derivatives of amides and esters of various fatty acids such as N-arachidonoylethanolamine(anandamide), N-palmitoylethanolamine, N-oleoylethanolamine, oleamide or 2-arachidonoylglycerol. These derivatives exert different pharmacological activities by interacting, inter alia, with the cannabinoid and vanilloid receptors.

The compounds of the invention block this degradation pathway and increase the tissue content of these endogenous substances. In this respect, they may be used in the prevention and treatment of pathologies in which the endogenous cannabinoids and/or any other substrate metabolized by the enzyme FAAH are involved. Mention may be made, for example, of the following diseases and complaints: pain, especially acute or chronic pain of neurogenic type: migraine, neuropathic pain including the forms associated with the herpes virus and diabetes and chemotherapy, acute or chronic pain associated with inflammatory diseases: arthritis, rheumatoid arthritis, osteoarthritis, spondylitis, gout, vascularitis, Crohn's disease, irritable bowel syndrome, acute or chronic peripheral pain, vertigo, vomiting, nausea, in particular post-chemotherapy nausea, eating disorders, in particular anorexia and cachexia of diverse nature, neurological and psychiatric pathologies: tremor, dyskinaesia, dystonia, spasticity, compulsive and obsessive behaviour, Tourette's syndrome, all forms of depression and anxiety of any nature or origin, mood disorders, psychoses, acute and chronic neurodegenerative diseases: Parkinson's disease, Alzheimer's disease, senile dementia, Huntington's chorea, lesions associated with cerebral ischaemia and cranial and medullary trauma, epilepsy, sleeping disorders, including sleep apnoea, cardiovascular diseases, in particular hypertension, cardiac arrhythmia, arteriosclerosis, heart attack, cardiac ischaemia, renal ischaemia, cancers: benign skin tumours, papillomas and cerebral tumours, prostate tumours, cerebral tumours (gliobastomas, medullo-epitheliomas, medullo-blastomas, neuroblastomas, tumours of embryonic origin, astrocytomas, astroblastomas, ependyomas, oligodendrogliomas, plexus tumour, neuroepitheliomas, pineal gland tumours, ependymoblastomas, malignant meningiomas, sarcomatoses, malignant melanomas, schwennomas), immune system disorders, especially autoimmune diseases: psoriasis, lupus erythematosus, connective tissue diseases, Sjögrer's syndrome, ankylosing spondylitis, undifferentiated spondylitis, Behcet's disease, haemolytic autoimmune anaemias, multiple sclerosis, amyotrophic lateral sclerosis, amylosis, graft rejection, diseases affecting the plasmocytic line, allergic diseases: immediate or delayed hypersensitivity, allergic rhinitis or allergic conjunctivitis, contact dermatitis, parasitic, viral or bacterial infectious diseases: AIDS, meningitis, inflammatory diseases, especially articular diseases: arthritis, rheumatoid arthritis, osteoarthritis, spondylitis, gout, vascularitis, Crohn's disease, irritable bowel syndrome, osteoporosis, ocular complaints: ocular hypertension, glaucoma, pulmonary complaints: respiratory pathway diseases, bronchospasms, coughing, asthma, chronic bronchitis, chronic obstruction of the respiratory pathways, emphysema, gastrointestinal diseases: irritable bowel syndrome, intestinal inflammatory disorders, ulcers, diarrhoea, urinary incontinence and inflammation of the bladder.

The use of the compounds according to the invention, in the form of the base, or a pharmaceutically acceptable acid-addition salt, hydrate or solvate, for the preparation of a medicinal product for treating the pathologies mentioned above forms an integral part of the invention.

A subject of the invention is also medicinal products comprising a compound of formula (I), or an acid-addition salt, or alternatively a pharmaceutically acceptable hydrate or solvate of the compound of formula (I). These medicinal products find their therapeutic use especially in the treatment of the pathologies mentioned above.

According to another of its aspects, the present invention relates to pharmaceutical compositions containing, as active principal, at least one compound according to the invention. These pharmaceutical compounds contain an effective dose of a compound according to the invention, or a pharmaceutically acceptable acid-addition salt, hydrate or solvate of the said compound, and optionally one or more pharmaceutically acceptable excipients.

The said excipients are chosen, according to the pharmaceutical form and the desired administration form, from the usual excipients known to those skilled in the art.

In the pharmaceutical compositions of the present invention for oral, sublingual, subcutaneous, intramuscular, intravenous, topical, local, intrathecal, intranasal, transdermal, pulmonary, ocular or rectal administration, the active principal of formula (I) above, or the possible acid-addition salt, solvate or hydrate thereof, may be administered in a unit administration form, as a mixture with standard pharmaceutical excipients, to man and animals for the prophylaxis or treatment of the above disorders or diseases.

The appropriate unit administration forms comprise oral forms such as tablets, soft or hard gel capsules, powders, granules, chewing gums and oral solutions or suspensions, sublingual, buccal, intratracheal, intraocular and intranasal administration forms, forms for administration by inhalation, subcutaneous, intramuscular or intravenous administration forms and rectal or vaginal administration forms. For topical administration, the compounds according to the invention may be used in creams, ointments or lotions.

By way of example, a unit administration form of a compound according to the invention in the form of a tablet may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

The said unit forms are dosed to allow a daily administration of from 0.01 to 20 mg of active principal per kg of body weight, depending on the presentation form.

There may be particular cases in which higher or lower doses are suitable, and such doses also form part of the invention. According to the usual practice, the dose that is suitable for each patient is determined by the doctor according to the mode of administration and the weight and response of the said patient.

According to another of its aspects, the invention also relates to a method for treating the pathologies mentioned above, which comprises the administration of an effective dose of a compound according to the invention, a pharmaceutically acceptable acid-addition salt thereof or a solvate or hydrate of the said compound.

The invention claimed is:

1. A compound corresponding to the general formula (I)

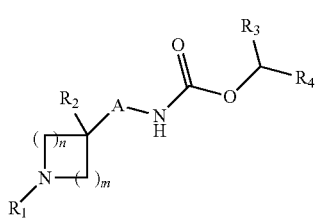

(I)

in which $R_2$ represents a hydrogen or fluorine atom or a hydroxyl, cyano, trifluoromethyl, $C_{1-6}$-alkyl, $C_{1-6}$-alkoxy or $NR_8R_9$ group;

n represents an integer equal to 1, 2 or 3 and m represents an integer equal to 1 or 2;

A represents a covalent bond or a group $C_{1-8}$-alkylene;

$R_1$ represents a group $R_5$ optionally substituted with one or more groups $R_6$ and/or $R_7$;

$R_5$ represents a group chosen from phenyl, pyridyl, pyridazinyl, pyrimidinyl, pyrazinyl, triazinyl, naphthyl, quinolinyl, isoquinolinyl, phthalazinyl, quinazolinyl, quinoxalinyl, cinnolinyl and naphthyridinyl;

$R_6$ represents a halogen atom or a cyano, —$CH_2CN$, nitro, hydroxyl, $C_{1-6}$-alkyl, $C_{1-6}$-alkoxy, $C_{1-6}$-thioalkyl, $C_{1-6}$-haloalkyl, $C_{1-6}$-haloalkoxy, $C_{1-6}$-halothioalkyl, $C_{3-7}$-cycloalkyl, $C_{3-7}$-cycloalkyl-$C_{1-3}$-alkylene, $C_{3-7}$-cycloalkyl-$C_{1-3}$-alkylene-O—, $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $SO_2R_8$, $SO_2NR_8R_9$ or —O—($C_{1-3}$-alkylene)-O— group;

$R_7$ represents a group chosen from furyl, pyrrolyl, thienyl, oxazolyl, isoxazolyl, thiazolyl, isothiazolyl, imidazolyl, pyrazolyl, oxadiazolyl, thiadiazolyl, phenyl, pyridyl, pyridazinyl, pyrimidinyl, pyrazinyl, triazinyl, naphthyl, quinolinyl, isoquinolinyl, phthalazinyl, quinazolinyl, quinoxalinyl, cinnolinyl, naphthyridinyl, imidazopyrimidinyl, thienopyrimidinyl, benzofuryl, benzothienyl, benzimidazolyl, benzoxazolyl, benzisoxazolyl, benzothiazolyl, benzisothiazolyl, indolyl, isoindolyl, indazolyl, pyrrolopyridyl, furopyridyl, thienopyridyl, imidazopyridyl, pyrazolopyridyl, oxazolopyridyl, isoxazolopyridyl, thiazolopyridyl, phenyloxy, benzyloxy and pyrimidinoxy; or the group(s) $R_7$ possibly being substituted with one or more groups $R_6$ that may be identical to or different from each other;

$R_3$ represents a hydrogen or fluorine atom, a group $C_{1-6}$-alkyl or a trifluoromethyl group;

$R_4$ represents a group chosen from furyl, pyrrolyl, thienyl, isothiazolyl, oxazolyl, isoxazolyl, pyrazolyl, oxadiazolyl, thiadiazolyl, imidazolyl, triazolyl and tetrazolyl;

this group being optionally substituted with one or more substituents chosen from a halogen atom, a group $C_{1-6}$-alkyl, $C_{1-6}$-haloalkyl, $C_{3-7}$-cycloalkyl, $C_{3-7}$-cycloalkyl-$C_{1-3}$-alkylene, $C_{1-6}$-haloalkoxy, cyano, $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $CON(R_8)(C_{1-3}$-alkylene-$NR_{10}R_{11})$, $SO_2R_8$, $SO_2NR_8R_9$, —O—($C_{1-3}$-alkylene)—O—, phenyl, phenyloxy, benzyloxy, pyridyl, pyrazinyl, pyridazinyl, triazinyl or pyrimidinyl; the phenyl, phenyloxy, pyridyl, pyrazinyl, pyridazinyl, triazinyl and pyrimidinyl groups possibly being substituted with one or more substituents chosen from a halogen atom and a cyano, nitro, $C_{1-6}$-alkyl, $C_{1-6}$-alkoxy, $C_{1-6}$-thioalkyl, $C_{1-6}$-haloalkyl, $C_{1-6}$-haloalkoxy, $C_{1-6}$-halothioalkyl, $C_{3-7}$-cycloalkyl or $C_{3-7}$-cycloalkyl-$C_{1-3}$-alkylene group;

$R_8$, $R_9$, $R_{10}$ and $R_{11}$ represent, independently of each other, a hydrogen atom or a group $C_{1-6}$-alkyl, or form, with the atom(s) that bear(s) them, in the case of $NR_8R_9$, a ring chosen from azetidine, pyrrolidine, piperidine, morpholine, thiomorpholine, azepine, oxazepine and piperazine rings, this ring being optionally substituted with a group $C_{1-6}$-alkyl or benzyl;

in the case of $NR_8COR_9$, a lactam ring; in the case of $NR_8CO_2R_9$, a oxazolidinone, oxazinone or oxazepinone ring; in the case of $NR_8SO_2R_9$, a sultam ring; in the case of $NR_8SO_2NR_8R_9$, a thiazolidine dioxide or thiadiazinane dioxide ring;

in the form of base or of a pharmaceutically acceptable acid-addition salt.

2. The compound according to claim 1, wherein $R_2$ represents a hydrogen or fluorine atom or a hydroxyl, $C_{1-6}$-alkyl or $NR_8R_9$ group;

in the form of base or of a pharmaceutically acceptable acid-addition salt.

3. The compound according to claim 1, wherein n represents an integer equal to 2 and m represents an integer equal to 2;

in the form of base or of a pharmaceutically acceptable acid-addition salt.

4. The compound according to claim 1, wherein A represents a group $C_{1-8}$-alkylene; in the form of base or of a pharmaceutically acceptable acid-addition salt.

5. The compound according to claim 1, wherein $R_1$ represents a group $R_5$ optionally substituted with one or more groups $R_6$ and/or $R_7$;

$R_5$ represents a phenyl, pyridyl, pyridazinyl, pyrimidinyl, pyrazinyl, quinolinyl, phthalazinyl or quinoxalinyl group;

$R_6$ represents a nitro, $C_{1-6}$-alkyl, $C_{1-6}$-alkoxy, $C_{1-6}$-haloalkyl, $C_{1-6}$-haloalkoxy, —O—($C_{1-3}$-alkylene)-O— or a halogen atom;

$R_7$ represents a phenyl group that may be substituted with one or more groups $R_6$ that may be identical to or different from each other; in the form of base or of a pharmaceutically acceptable acid-addition salt.

6. The compound according to claim 1, wherein $R_3$ represents a trifluoromethyl, a $C_{1-6}$-alkyl or a hydrogen atom; in the form of base or of a pharmaceutically acceptable acid-addition salt.

7. The compound according to claim 1, wherein $R_4$ represents a group chosen from oxazolyl, isoxazolyl, furyl, imidazolyl, pyrazolyl, oxadiazolyl, thiadiazolyl and triazolyl groups; this group optionally substituted with one or more substituents chosen from a group $C_{1-6}$-alkyl, COOR$_8$, CON($R_8$)($C_{1-3}$-alkylene-NR$_{10}$R$_{11}$), CONR$_8$R$_9$, phenyl; the phenyl group possibly being substituted with one or more substituents chosen from a halogen atom and a group $C_{1-6}$-alkoxy;

$R_8$ and $R_9$ represent, independently of each other, a hydrogen atom or a group $C_{1-6}$-alkyl, or form, together with the atom that bears them, a piperazine ring, $R_{10}$ and $R_{11}$ represent, independently of each other, a hydrogen atom or a group $C_{1-6}$-alkyl;

in the form of base or of a pharmaceutically acceptable acid-addition salt.

8. The compound according to claim 1, wherein
$R_1$ represents a group $R_5$ optionally substituted with one or more groups $R_6$ and/or $R_7$;
$R_5$ represents a phenyl, pyridyl, pyrazinyl or quinolinyl group; $R_6$ represents a halogen atom;
$R_7$ represents a phenyl group that may be substituted with one or more groups $R_6$ that may be identical to or different from each other,
$R_2$ and $R_3$ represent a hydrogen atom;
$R_4$ represents a 3-carbamoylisoxazol-5-yl group;
n represents an integer equal to 2 and m represents an integer equal to 2;
A represents an alkylene group;
in the form of base or of a pharmaceutically acceptable acid-addition salt.

9. A process for preparing the compound of claim 1, comprising the step consisting in reacting an amine of general formula (II),

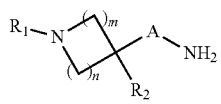

(II)

in which A, $R_1$, $R_2$, m and n are as defined in the general formula (I) according to claim 1, with a carbonate of general formula (III)

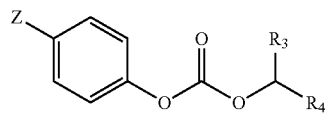

(III)

in which Z represents a hydrogen atom or a nitro group, and $R_3$ and $R_4$ are as defined in the general formula (I) according to claim 1,
in the presence of a base, in a solvent at a temperature between room temperature and the reflux point of the solvent.

10. A process for preparing the compound of claim 1, comprising the step that consists in reacting an amine of general formula (II),

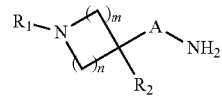

(II)

in which A, $R_1$, $R_2$, m and n are as defined in the general formula (I) according to claim 1, with phenyl or 4-nitrophenyl chloroformate,
in the presence of a base, in a solvent at a temperature between 0° C. and room temperature, to give the carbamate derivative of general formula (IV),

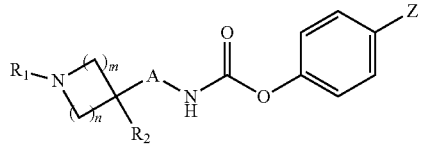

(IV)

in which A, $R_1$, $R_2$, m and n are as defined in the general formula (I) according to claim 1, and Z represents a hydrogen atom or a nitro group;
and then in converting the carbamate derivative of general formula (IV) thus obtained into a compound of general formula (I), via the action of an alcohol of general formula HOCHR$_3$R$_4$ (IIIa), in which $R_3$ and $R_4$ are as defined in the general formula (I) according to claim 1,
in the presence of a base, in a solvent at a temperature between room temperature and the reflux point of the solvent.

11. A pharmaceutical composition comprising the compound of claim 1, in the form of base or of a pharmaceutically acceptable acid-addition salt.

12. The pharmaceutical composition of claim 11, further comprising one or more pharmaceutically acceptable excipients.

* * * * *